US012780831B2

(12) United States Patent
Maccecchini et al.

(10) Patent No.: US 12,780,831 B2
(45) Date of Patent: Nov. 3, 2026

(54) SOLID FORMS OF POSIPHEN D-TARTRATE

(71) Applicant: ANNOVIS BIO, INC., Malvern, PA (US)

(72) Inventors: Maria Maccecchini, Malvern, PA (US); Michael A. Christie, Phoenixville, PA (US); Vinu V. Panikkattu, Lafayette, IN (US); Christopher Scott Seadeek, West Lafayette, IN (US)

(73) Assignee: ANNOVIS BIO, INC., Malvern, PA (US)

( * ) Notice: Subject to any disclaimer, the term of this patent is extended or adjusted under 35 U.S.C. 154(b) by 0 days.

(21) Appl. No.: 19/381,358

(22) Filed: Nov. 6, 2025

(65) Prior Publication Data

US 2026/0062418 A1 Mar. 5, 2026

Related U.S. Application Data

(63) Continuation-in-part of application No. PCT/US2024/034966, filed on Jun. 21, 2024.

(60) Provisional application No. 63/580,011, filed on Sep. 1, 2023, provisional application No. 63/509,356, filed on Jun. 21, 2023.

(51) Int. Cl.
*C07D 487/04* (2006.01)
*A61K 31/407* (2006.01)

(52) U.S. Cl.
CPC .......... *C07D 487/04* (2013.01); *A61K 31/407* (2013.01)

(58) Field of Classification Search
CPC .............................. A61K 31/407; A61P 25/28
See application file for complete search history.

(56) References Cited

U.S. PATENT DOCUMENTS

| | | | |
|---|---|---|---|
| 2004/0024043 | A1 | 2/2004 | Greig et al. |
| 2009/0118347 | A1 | 5/2009 | Bruinsma |
| 2020/0237722 | A1 | 7/2020 | Maccecchini |
| 2020/0375948 | A1 | 12/2020 | Maccecchini |

FOREIGN PATENT DOCUMENTS

| | | | |
|---|---|---|---|
| WO | 2025/017530 | A1 | 1/2025 |

OTHER PUBLICATIONS

Ningrum, 2023, Brain Sciences (Year: 2023).*
Clinical and Medical Case Reports, 2024 (Year: 2024).*
UPMC, 2012 (Year: 2012).*
USP Reference article, 2016, p. 1-11 (Year: 2016).*
Qian-Sheng Yu, et al., Synthesis of the Alzheimer Drug Posiphen into its Primary Metabolic Products (+)-N1-norPosiphen, (+)-N8-norPosiphen and (+)-N1, N8- bisnorPosiphen, their Inhibition of Amyloid Precursor Protein, α-Synuclein Synthesis, Interleukin-1BRelease, and Cholinergic Action, Synthesis of the Alzheimer Drug Posiphen into its Primary Metabol . . . : Ingenta Connect (Aug. 1, 2013) Retrieved from: https://www.ingentaconnect.com/content/ben/aiaamc/2013/00000012/00000002/art00003.
ISR and WO issued Sep. 26, 2024 in International Application No. PCT/US2024/034966.

* cited by examiner

*Primary Examiner* — Umamaheswari Ramachandran
(74) *Attorney, Agent, or Firm* — Duane Morris LLP; Thomas J. Kowalski

(57) ABSTRACT

Solid forms of (3aR)-1, 3a, 8-trimethyl-1, 2, 3, 3a, 8, 8a-hexahydropyrrolo (2, 3-b) indol-5-yl phenyl-carbamate tartrate, including crystalline (3aR)-1, 3a, 8-trimethyl-1, 2, 3, 3a, 8, 8a-hexahydropyrrolo (2, 3-b) indol-5-yl phenyl-carbamate tartrate (posiphen D-tartrate Form A), crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), crystalline (3aR)-1, 3a, 8-trimethyl-1, 2, 3, 3a, 8, 8a-hexahydropyrrolo (2, 3-b) indol-5-yl phenyl-carbamate tartrate Form A having the peak of Pattern C (posiphen D-tartrate Form A+Pattern C), and amorphous (3aR)-1, 3a, 8-trimethyl-1, 2, 3, 3a, 8, 8a-hexahydropyrrolo (2, 3-b) indol-5-yl phenyl-carbamate tartrate, are disclosed. Pharmaceutical compositions comprising posiphen D-tartrate Form A, posiphen D-tartrate Form B, posiphen D-tartrate Form A having the peaks of Pattern C, and amorphous posiphen D-tartrate, and methods of treating various conditions by administering these solid forms, are also disclosed.

11 Claims, 23 Drawing Sheets physostigmine salicylate eseroline posiphen

Posiphen D-tartrate Form A

Posiphen D-tartrate Form A

Posiphen D-tartrate Form B

SOLID FORMS OF POSIPHEN D-TARTRATE

RELATED APPLICATIONS AND INCORPORATION BY REFERENCE

This application is a continuation-in-part of international patent application Serial No. PCT/US2024/034966, filed Jun. 21, 2024, which published as PCT Publication No. WO 2024/263878 A1 on Dec. 26, 2024, which claims benefit of U.S. provisional patent application Ser. No. 63/580,011, filed Sep. 1, 2023, and U.S. provisional patent application Ser. No. 63/509,356, filed Jun. 21, 2023, the contents of which are hereby incorporated by reference in their entirety. Reference is also made to U.S. patent application Ser. No. 10/042,586, filed Jan. 9, 2002, now U.S. Pat. No. 6,495,700, Ser. No. 10/415,765, filed Feb. 6, 2004, now U.S. Pat. No. 7,153,882, Ser. No. 10/593,179, filed Oct. 9, 2005, now U.S. Pat. No. 7,625,942, Ser. No. 12/357,115, filed Jan. 21, 2009, now U.S. Pat. No. 7,786,162, Ser. No. 12/841,888, filed Jul. 22, 2010, now U.S. Pat. No. 8,258,172, Ser. No. 13/041,211, filed Mar. 4, 2011, now abandoned, Ser. No. 15/751,337, filed Feb. 8, 2018, which is pending, Ser. No. 15/450,937, filed Mar. 6, 2017, now U.S. Pat. No. 10,383,851, Ser. No. 16/994,881, filed Aug. 17, 2020, now U.S. Pat. No. 11,400, 075, Ser. No. 16/994,881, filed Aug. 17, 2020, now U.S. Pat. No. 11,382,893, Ser. No. 16/994,921, filed Aug. 17, 2020, now U.S. Pat. No. 11,376,238, Ser. No. 16/827,194, filed Mar. 23, 2020, now U.S. Pat. No. 11,596,621.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to solid forms of posiphen, in particular, posiphen D-tartrate, pharmaceutical compositions comprising the novel solid forms, and methods of treating and/or preventing various conditions by administering the novel solid forms.

BACKGROUND OF THE INVENTION

The solid form (i.e., the crystalline or amorphous form) of a pharmaceutical compound can be important relative to its pharmacological properties and development as a viable active pharmaceutical ingredient ("API").

Pharmaceutical products are often formulated from crystalline compounds because crystalline materials may provide higher levels of purity and resistance to physical and chemical instabilities under ambient conditions, relative to amorphous forms. Crystalline forms of a compound may in some cases, offer advantages over amorphous forms, such as improved solubility, stability, processing improvements, etc., and different crystalline forms (e.g. polymorphs of the compound) may offer greater or lesser advantages over one another. However, crystalline forms of a compound are not predictable, and in fact, are not always possible. It is a well-accepted principle that the formation of a new polymorphic or crystalline form (e.g. a new crystalline salt form) of a compound is totally unpredictable, and until a particular polymorph is prepared, there is no way to know whether it might exist, how to prepare it, or what its properties might be. Bernstein, J. Polymorphism in Molecular Crystals. New York: Oxford University Press, 9 (2002).

Unlike a crystalline solid, which has an orderly array of unit cells in three dimensions, amorphous forms lack long-range order because molecular packing is more random. As a result, amorphous organic compounds tend to have different properties than their crystalline counterparts. For example, amorphous compounds often have greater solubility than crystalline forms of the same compound. Thus, by way of example only, in pharmaceutical formulations whose crystalline forms are poorly soluble, amorphous forms may present attractive formulation options. As such, amorphous APIs may be used to improve physical and chemical properties of drugs, such as, for example, dissolution and bioavailability.

Solid forms of a compound, including both crystalline and amorphous forms, are of particular interest to the pharmaceutical industry, for example to those involved in the development of suitable dosage forms, if the solid form of the API (e.g. the crystalline polymorphic form or amorphous form) is not held constant during clinical or stability studies, the exact dosage form used or studied may not be comparable from one lot to another. In addition, regulatory agencies require solid form characterization and control of the API for approval.

Posiphen D-tartrate, (3aR)-1, 3a, 8-trimethyl-1, 2, 3, 3a, 8, 8a-hexahydropyrrolo (2, 3-b) indol-5-yl phenyl-carbamate tartrate, the D-tartaric acid salt of posiphen, has the following structure shown below. Posiphen is useful for treating and/or preventing a variety of conditions, such as, for example, combating neurodegenerative diseases such as Alzheimer's disease and disorders associated with abnormal production of amyloid precursor protein such as dementia. Examples of neurotoxic aggregating proteins include, but are not limited to, amyloid precursor protein (APP/Aβ), super oxide dismutase (SOD1), alpha-synuclein (SNCA), NAC, prion protein (PrP), huntingtin (HTT), microtubule associated protein (MAPT/Tau), TDP43, and C9orf72.

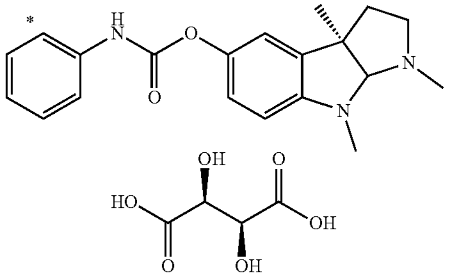

Accordingly, there is a need in the art to identify novel solid forms of posiphen D-tartrate, particularly those having advantageous chemical and/or physical properties. This invention answers those needs by providing novel solid forms of posiphen D-tartrate, including forms having improved properties.

SUMMARY OF THE INVENTION

In accordance with various embodiments of the invention and after extensive experimentation, this disclosure provides novel and nonobvious crystalline forms of posiphen, including the two forms referred to herein as Forms A and B.

The invention in various embodiments also relates to pharmaceutical compositions and formulations comprising the novel crystalline forms, and methods of treating and/or preventing various conditions by administering the novel crystalline forms.

According to one aspect of the present invention, the present invention provides a solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B).

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) has characteristics consistent with those described in Table 4 and/or Table 7 and/or FIG. 10 and/or FIG. 11 and/or FIG. 12 and/or FIG. 13 and/or FIG. 21 and/or FIG. 27 and/or as prepared according to a method as herein described and/or claimed and/or according to Example 3 and/or Example 8.

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) is characterized by an X-ray powder diffraction pattern having characteristic peaks at 5.16, 8.56, 10.3, 11.24, 13.14, 13.48, 14.66, 15.24, 15.44, 15.76, 16.18, 16.54, 17.48, 17.94, 18.08, 19.72, 20.62, 20.76, 21.22, 21.5, 22.2, 22.54, 23.46, 24.4, 24.72, 26.4, 26.86, 27.14, 27.48, 27.7, 28.52, 28.74, 29.14, 29.96, 30.68, 31.14, 32.3, 33.26, 35.44, 37.24, and 37.74 in 2θ.

According to another aspect of the present invention, the present invention provides substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate, or posiphen D-tartrate Form B that has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC).

According to another aspect of the present invention, the present invention provides a method of preparing a solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate comprising preparing crystalline (3aR)-1, 3a, 8-trimethyl-1, 2, 3, 3a, 8, 8a-hexahydropyrrolo (2, 3-b) indol-5-yl phenyl-carbamate tartrate (posiphen D-tartrate Form A) and converting the posiphen D-tartrate Form A to crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B).

In one embodiment, the present invention provides a pharmaceutical formulation comprising the solid form of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), the substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate, or posiphen D-tartrate Form B that has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC), or crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) having been prepared by the methods disclosed herein, and a pharmaceutically acceptable carrier.

According to another aspect of the present invention, the present invention provides a method of treating a neurological disorder in a subject in need thereof, comprising administering to the subject an effective amount of a pharmaceutical composition comprising crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), the substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate, or posiphen D-tartrate Form B that has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC), or crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) having been prepared by the methods disclosed herein, and a pharmaceutically acceptable carrier;

wherein the neurological disorder comprises:

a chronic neurodegeneration, wherein the chronic neurodegeneration comprises Alzheimer's disease, frontotemporal dementia, chronic traumatic encephalopathy, tauopathies, Parkinson's and alpha-synucleopathies, prion disease, transmissible spongiform encephalopathies (TSE), Down Syndrome, Huntington's disease, amyotrophic lateral sclerosis, multiple sclerosis, or other dementias and neurodegenerative disorders which present as misfolding, aggregation and accumulation of proteins in the brain, resulting in axonal transport impairment, inflammation, and eventual cell death; or an acute neurodegeneration, wherein the acute neurodegeneration comprises traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma; or a neuropsychiatric indication, wherein the neuropsychiatric indication comprises depression, schizophrenia, dementia, Alzheimer's disease, anxiety, or substance abuse disorder; or a mental illness, wherein the mental illness comprises autism, attention deficit-hyperactivity disorder, bipolar disorder, depression and major depressive disorder, behavioral problems, posttraumatic stress disorder or schizophrenia.

In one embodiment, the neurological disorder is a chronic neurodegeneration.

In another embodiment, the chronic neurodegeneration comprises Alzheimer's disease, frontotemporal dementia, chronic traumatic encephalopathy, tauopathies, Parkinson's and alpha-synucleopathies, prion disease, transmissible spongiform encephalopathies (TSE), Down Syndrome, Huntington's disease, amyotrophic lateral sclerosis, multiple sclerosis, or other dementias and neurodegenerative disorders which present as misfolding, aggregation and accumulation of proteins in the brain, resulting in axonal transport impairment, inflammation, and eventual cell death.

In another embodiment, the neurological disorder is an acute neurodegeneration.

In another embodiment, the acute neurodegeneration comprises traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma.

In another embodiment, the neurological disorder is a neuropsychiatric indication.

In another embodiment, the wherein the neuropsychiatric indication comprises depression, schizophrenia, dementia, Alzheimer's disease, anxiety, or substance abuse disorder.

In another embodiment, the neurological disorder is a mental illness.

In another embodiment, the mental illness is wherein the mental illness comprises autism, attention deficit-hyperactivity disorder, bipolar disorder, depression and major depressive disorder, behavioral problems, posttraumatic stress disorder or schizophrenia.

In one embodiment, the method for treating the neurological disorder provides for a dosage of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) from about 0.1 mg/kg to about 100 mg/kg of body weight.

In another embodiment, the method for treating neurological disorder provides for a dosage of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) from about 1 mg/kg to about 20 mg/kg of body weight.

In one embodiment, the method provides for daily administration to the subject.

In another embodiment, the method provides for a single daily administration to the subject.

In another embodiment, the subject is human.

In another embodiment, the administering is oral administration.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112(a)) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Figure 1:
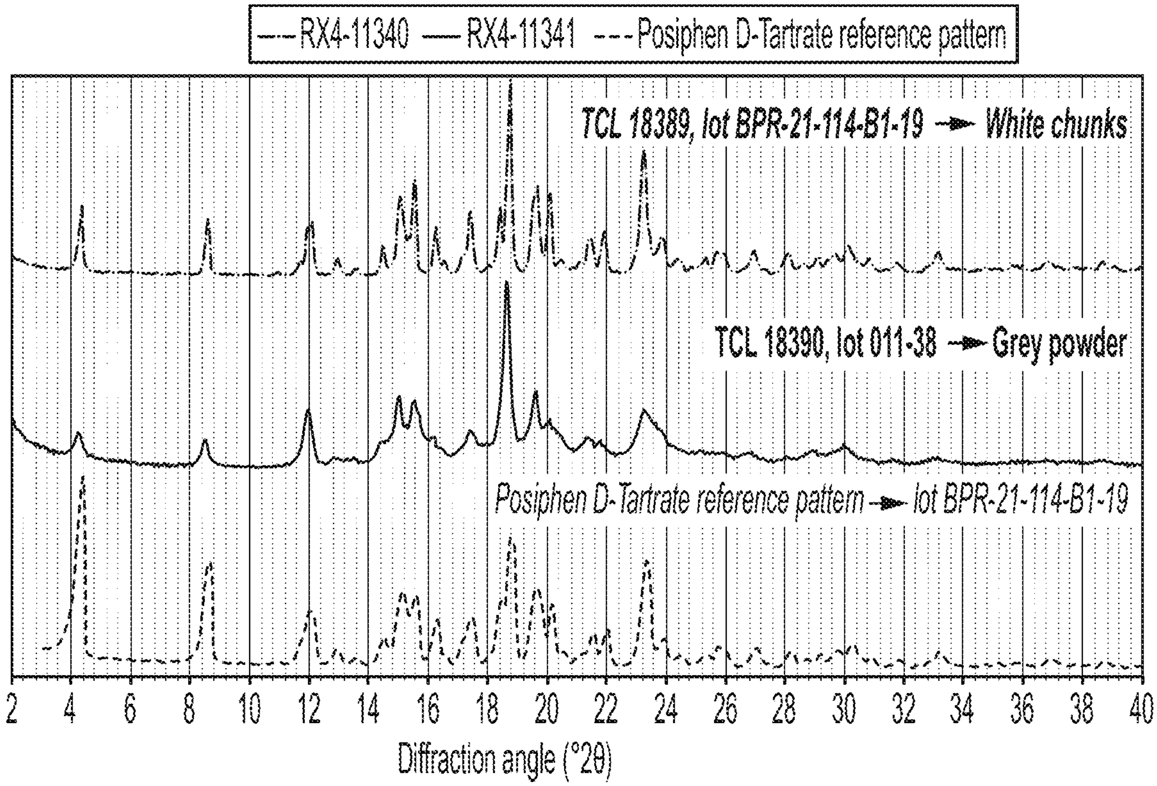
FIG. 1 shows a PXRD pattern of different forms of posiphen D-tartrate. The posiphen D-tartrate from lot BPR-21-114-B1-19 had an appearance as a white solid. The posiphen D-tartrate from lot 011-38 had an appearance of a grey powder. The bottom trace is a reference trace. These forms of posiphen D-tartrate are designated as Form A.

The following detailed description, given by way of example, but not intended to limit the invention solely to the specific embodiments described, may best be understood in conjunction with the accompanying drawings.

DETAILED DESCRIPTION OF THE INVENTION

In various embodiments, the invention relates to novel and nonobvious crystalline Forms A and B of posiphen D-tartrate, as well as a metastable form of posiphen D-tartrate formed in a mixture with Form A. This metastable form of posiphen D-tartrate exhibited the peaks of Pattern C in the XRPD trace. Exemplary methods of preparing these solid forms are found in the examples below.

Posiphen D-tartrate Form B is a dihydrate whereas posiphen D-tartrate Form A is an anhydrate. As shown in the below characterization of posiphen D-tartrate Form A and posiphen D-tartrate Form B, the anhydrate posiphen D-tartrate Form A does not take up water in the solid state and form the corresponding dihydrate of posiphen D-tartrate Form B. On the other hand, posiphen D-tartrate Form B does not lose water when dried at typical manufacturing conditions. Therefore, posiphen D-tartrate Form A and posiphen D-tartrate Form B do not readily interconvert from anhydrate to dihydrate and are distinct and separate compounds that have separate and distinct crystalline phases.

Posiphen D-tartrate Form B, a polymorph of posiphen D-tartrate Form A, as shown in pharmacokinetic experiments measuring the concentrations of the compound in plasma, the brain, and in cerebrospinal fluid over time following administration, is initially present at higher concentrations following administration of the compound and is retained for longer periods in the blood, brain, and cerebrospinal fluid as compared to Form A. Thus, Form B possesses the advantages of a faster delivery and a longer half-life than Form A. These advantages enable higher, initial effective dosages of the drug when utilizing the same amounts and concentrations during administration, wherein the drug persists and retains its efficiency over longer periods of time.

Posiphen D-tartrate Form B has the CAS Number 3032752-92-1. Thus, Form B is recognized as distinct from Form A (CAS Number 2763279-48-5) including as shown by the distinct CAS number assigned to Form B.

Posiphen inhibits the synthesis of neurotoxic aggregating proteins, which have been implicated in mental illness and neurodegenerative and neurological diseases and disorders. Neurotoxic aggregating proteins, which, due to misfolding, aggregation and accumulation, impair axonal transport, cause inflammation, and kill nerve cells. Examples of neurotoxic aggregating proteins include, but are not limited to, amyloid precursor protein (APP/Aβ), super oxide dismutase (SOD1), alpha-synuclein (SNCA), NAC, prion protein (PrP), huntingtin (HTT), microtubule associated protein (MAPT/Tau), TDP43, and C9orf72.

Neurological disorders can include chronic neurodegeneration. Examples of chronic neurodegeneration include, but are not limited to Alzheimer's disease, frontotemporal dementia, chronic traumatic encephalopathy, tauopathies, Parkinson's and alpha-synucleopathies, prion disease, Down Syndrome, Huntington's disease, amyotrophic lateral sclerosis, multiple sclerosis and other dementias and neurodegenerative disorders which present as misfolding, aggregation and accumulation of proteins in the brain, resulting in axonal transport impairment, inflammation, and eventual cell death.

For example, in Alzheimer's disease (AD), a progressive neurodegenerative condition leading to loss of memory, the major pathological hallmarks are characterized by the appearance of senile plaques which are primarily composed of Aβ and neurofibrillary tangle aggregates (Selkoe, 1997; Roberson and Harrell, 1997). Aβ, a 40-42 residue peptide, is derived from a larger protein, βAPP (695-770 amino acids), whose biological functions remain to be fully determined but whose pathological role may be separated on the basis of its final proteolysed form (Checler, 1995; Selkoe, 1997). βAPP derivatives are generated by three enzymatic activities termed α-, β-, and γ-secretases, to produce different protein fragments that are either neuroprotective or amyloidogenic. An aspartyl protease with β-secretase like properties has been identified (Hussaain et al., 1999; Sinha et al., 1999; Vassar et al., 1999; Yan et al., 1999), that may serve as a therapeutic marker. However, its value as a target for drug development is complicated by its location within two membranes (plasma and Golgi apparatus). Furthermore, the role of alternative compensatory activities remains unclear. Indeed, a second enzyme, Thimet oligopeptidase, was found capable of β-secretase activity in transfected COS cells (Koike et al., 1999). A major pharmaceutical industry focus has been to look for agents that reduce amyloidogenic processing using compounds that can manipulate βAPP to produce non-amyloidogenic by-products. However, it is important to note that the role of alternative βAPP fragments in AD is unclear.

Regarding regulatory mechanisms involved in βAPP processing, environmental agents have been demonstrated to accelerate βAPP turnover into its pathological Aβ form (Selkoe, 1997). Furthermore, the cellular surrounding of neurons, particularly astrocytes and microglia, are additional and non-neuronal sources of βAPP (Funato et al., 1998; Akiyama et al., 2000). Thus, amyloid plaque occurrence is often associated with enlarged microglia which produce interleukin-1 (IL-1), a potent mediator of astroglial proliferation and βAPP production (Akiyama et al., 2000). The fact that IL-1 can influence this process suggests that signaling pathways induced by cytokines are interconnected with βAPP metabolism. Another example of receptor-signaling association and βAPP homeostasis is demonstrated through the activation of muscarinic m1 and m3 receptors which modify βAPP synthesis and processing through MAP kinase dependent and independent pathways (Felder et al., 1993; Nitsch et al., 1992 and 1994). Reductions in muscarinic receptors, as in AD, may alter βAPP metabolism and result in subsequent Aβ deposition. Cholinergic system impairment has been reversed with moderate success by the use of anticholinesterases (Greig et al., 1995; Brossi et al., 1996), the only approved drugs for AD treatment.

Anticholinesterases dramatically improves cognitive performance in rodents and is in clinical trials (Greig et al., 1995; Patel et al., 1998). Studies of rats with forebrain cholinergic lesions that are known to dramatically increase βAPP in cholinergic projection areas have shown that anticholinesterases can protect against this and additionally, reduce βAPP production in naive animals (Haroutunian et al., 1997). Both βAPP processing and cholinesterase activity are affected in the AD brain (Bronfman et al., 1996). The anticholinesterase, tacrine, has been shown to decrease βAPP and Aβ in neuronal cells in vitro (Lahiri et al., 1998). Current studies have focused on the molecular changes induced by compounds such as posiphen.

Neurological disorders can also include acute neurodegeneration. Examples of acute neurodegeneration include, but are not limited to traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, and acute angle-closure glaucoma.

Neurological disorders can also include neuropsychiatric indications. Examples of neuropsychiatric indications include, but are not limited to depression, schizophrenia, dementia, Alzheimer's disease, anxiety, and substance abuse disorder.

Neurological disorders can also include mental illness. Impaired neuronal communication, axonal transport, and abnormal levels of neurotoxic aggregating proteins have been implicated in mental illness. Examples of mental illnesses include, but are not limited to autism, attention deficit-hyperactivity disorder, bipolar disorder, depression and major depressive disorder, behavioral problems, post-traumatic stress disorder and schizophrenia.

It is the cholinergic action of anticholinesterases that provides the compounds their ability to improve cognitive performance in both animal models and humans. Likewise, it is the cholinergic action that is also dose limiting for these same compounds (nausea, sweating, GI effects) (Becker et al., 1991). Conversely, the (+)-enantiomers are unable to inhibit either acetylcholinesterase (AChE., EC 3.1.1.7.) or butyrylcholinesterase (BChE., EC 3.1.1.8.), and hence have no cholinergic action. The (+)-enantiomers are also unnatural isomers and thus, need to be synthesized. Synthetic procedures provide a mixture of (+)- and (−)-forms that require early separation into optically pure forms to eventually obtain the final products. The preparation and pharmacologic activity of posiphen D-tartrate are described in, for example, U.S. Pat. Nos. 6,495,700, 7,153,882, 7,625,942, 7,786,162, 8,258,172, 10,383,851, 11,376,238, 11,382,893, 11,400,075, 11,596,621, WO 2003/059909, Yu, et al. *Antiinflamm. Antiallergy Agents Med. Chem.* 2012; 12(2): 117-128, Kuo et al. *Am. J. Neurodegener. Dis.* 2019; 8(1): 1-15, Maccecchini et al., *J. Neurol. Neurosurg. Psychiatry* 2012; 83:894-902, all of which are incorporated herein by reference.

While therapeutic efficacy is a primary concern for a therapeutic agent such as posiphen D-tartrate, as discussed above, the solid form of a pharmaceutical drug candidate is also important. For example, each solid form of a drug candidate can have different solid state (physical and chemical) properties. The differences in physical properties exhibited by a different solid form of an API, such as a polymorph of the original compound, can affect pharmaceutical parameters such as storage stability, compressibility and density, all of which may be important in formulation and product manufacturing, and solubility and dissolution rates, which may be important factors in determining bioavailability. Because these practical physical properties can be influenced by the solid form of the API, they can significantly impact the selection of a compound as an API, the ultimate pharmaceutical dosage form, the optimization of manufacturing processes, and absorption in the body. Moreover, finding the most adequate form for further drug development can reduce the time and the cost of that development. It may also be beneficial to identify and characterize additional crystal forms so that they may be recognized if they appear during drug development and/or manufacturing.

Obtaining pure solid forms, then, can be extremely useful in drug development, as it generally permits better characterization of the drug candidate's chemical and physical properties. Crystalline forms often have more favorable chemical and physical properties than amorphous forms of the same compound. As such, one or more crystalline forms may possess more favorable pharmacology than amorphous forms or be easier to process, or may have better storage stability. Similarly, one crystalline form may possess more favorable pharmacology, may be easier to process, or may have better storage stability than another, or than an amorphous form, or vice versa.

One such physical property is a pharmaceutical compound's dissolution rate in aqueous fluid. The rate of dissolution of an API in a patient's stomach fluid may have therapeutic consequences since the dissolution rate impacts the rate at which an orally administered active ingredient may reach the patient's bloodstream.

Another such physical property is thermodynamic stability. The thermodynamic stability of an active ingredient may have consequences on the manufacturing process and storage stability of the API and/or the formulation.

A crystalline form of a compound generally possesses distinct crystallographic and spectroscopic properties when compared to other crystalline forms having the same chemical composition. Crystallographic and spectroscopic properties of the particular form are typically measured by one or more techniques such as powder x-ray diffraction (PXRD), single crystal x-ray crystallography, solid state NMR spectroscopy, infrared spectroscopy (IR), or Raman spectroscopy, among other techniques. A particular solid form of a compound may often exhibit distinct thermal behavior as well. Thermal behavior is measured in the laboratory by such techniques as capillary melting point, thermogravimetric analysis (TGA), and differential scanning calorimetry (DSC).

Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies. As such, finding the right conditions to obtain a particular solid form of the desired API (e.g., a particular crystalline polymorphic form or an amorphous form), with pharmaceutically acceptable properties, is critical to drug development, but can take significant time, resources, and effort.

In further embodiments, the invention relates to pharmaceutical compositions and formulations comprising the novel solid forms of posiphen D-tartrate, and methods of treating and/or preventing various conditions by administering the solid forms.

The following Table 1 shows the definitions of the abbreviations and acronyms used in the present application.

TABLE 1

Abbreviations and Acronyms

| Category | Abbreviation/ Acronym | Full Name/Description |
|---|---|---|
| Solvents/ Reagents | ACN | Acetonitrile |
| | AE | Acetone |
| | BOH | Butanol |
| | CLF | Chloroform |
| | DCM | Dichloromethane |
| | DMSO | Dimethyl sulfoxide |
| | DOX | Dioxane |
| | EA | Ethyl acetate |
| | EOH | Ethanol |
| | $H_2O$ | Water |
| | HEP | Heptanes |
| | HEX | Hexanes |
| | IPA | Isopropanol |
| | IPE | Isopropyl ether |
| | MEK | Methyl ethyl ketone |
| | MOH | Methanol |
| | MIBK | Methyl isobutyl ketone |
| | THF | Tetrahydrofuran |

TABLE 1-continued

Abbreviations and Acronyms

| Category | Abbreviation/ Acronym | Full Name/Description |
|---|---|---|
| Crystallization Techniques | ASA | Antisolvent Addition |
| | Evap | Evaporation |
| | SE | Slow Evaporation |
| | CL | Cooling |
| | SL | Slurry |
| | ISL | Interconversion Slurry |
| | VD | Vapor Diffusion |
| Analytical Techniques | PXRD/XRPD | X-ray Powder Diffraction |
| | $^1H$ NMR | Proton Nuclear Magnetic Resonance Spectroscopy |
| | TGA | Thermogravimetric Analysis |
| | DSC | Differential Scanning Calorimetry |
| | DVS | Dynamic Vapor Sorption |
| | PLM | Polarized Light Microscopy |
| | FTIR | Fourier Transform Infrared Spectroscopy |
| | Raman | Raman Spectroscopy |
| Miscellaneous | API | Active Pharmaceutical Ingredient |
| | RH | Relative Humidity |
| | ppt | Precipitate |
| | Endo | Endotherm |
| | DI | Deionized |
| | ST | Sub-ambient Temperature |
| | SD | Seeded |
| | RT | Room/Ambient Temperature |
| | ET | Elevated Temperature |
| | LC | Low Crystallinity |
| | VP | Volume Process |
| | WA | Water Activity |

As used herein, the term "polymorph" refers to different crystalline forms of the same compound and other solid state molecular forms, including pseudopolymorphs. The terms "pseudopolymorph" and "pseudomorph" as used herein are interchangeable and are meant to include hydrates (i.e., water present in the crystalline structure) and solvates (i.e., solvents other than water) of the compound, of both a fixed or stoichiometric and variable nature. Different crystalline forms, such as polymorphs, have different crystal structures due to a different packing of the molecules in the lattice. This results in a different crystal symmetry and/or unit cell parameters which directly influences the physical properties of the form, including X-ray characteristics (both single-crystal and XRPD) of crystals or powders. A different polymorph, for example, will in general diffract at a different set of angles and will give different values for the intensities. Therefore, when available, X-ray techniques can be used to identify different polymorphs, or a solid form that comprises more than one polymorph, generally in a reproducible and reliable way, S. Byrn et al., "Pharmaceutical Solids: A Strategic Approach to Regulatory Considerations," *Pharmaceutical Research*, Vol. 12, No. 7, p. 945-954, 1995; J. K. Haleblian and W. McCrone, "Pharmaceutical Applications of Polymorphism," *Journal of Pharmaceutical Sciences*, Vol. 58, No. 8, p. 911-929, 1969.

As used herein, the terms "XRPD" or "PXRD", used interchangeably, refer to x-ray powder diffraction. Unless otherwise noted, XRPD analyses were performed either on a Rigaku Smart Lab X-ray diffraction system.

The Rigaku Smart-Lab X-ray diffraction system was configured for reflection Bragg-Brentano geometry using a line source X-ray beam. The x-ray source was a Cu Long Fine Focus tube operated at 40 kV and 44 ma. That source provides an incident beam profile at the specimen that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the specimen itself acting as the focusing component in the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0° Soller slits in both the incident and diffracted beam paths. Each powder specimen was prepared in a low background Si holder using light manual pressure to keep the sample surface flat and level with the reference surface of the sample holder. The single crystal Si low background holders have a small circular recess (7 mm diameter and about 1 min depth) that holds between 5 and 10 mg of powdered material. The standard measurement range was from 2 to 40° 2θ using a continuous scan of 3 °2θ per minute with an effective step size of 0.02 °2θ.

As used herein, "IR" refers to infrared spectroscopy. Unless otherwise noted, IR spectra were obtained on a Thermo Scientific model iS50 Fourier-transform (FT) IR spectrophotometer equipped with a deuterated triglycine sulfate (DTGS) detector, a potassium bromide (KBr) beam-splitter, and a Polaris™ long-life IR source.

As used herein, the term "DSC" refers to differential scanning calorimetry. Unless otherwise noted, DSC data disclosed herein were obtained using a TA Instruments Q2500 Discovery Series instrument. Samples were prepared in crimped aluminum pans and kept under a flow of nitrogen during analysis. The samples were heated from approximately 25° C. to 300° C. at a rate of 10° C. per minute.

As used herein, the term "$^1$H-NMR" refers to proton nuclear magnetic resonance spectroscopy. Solution $^1$H NMR data disclosed herein were acquired on a Bruker Avance NEO 400 spectrometer (400 MHz $^1$H) spectrometer. Proton chemical shifts are reported in ppm, referenced to the NMR solvent. Unless otherwise indicated, NMR data were collected at 25° C.

As used herein, the term "DVS" refers to dynamic vapor sorption analysis. DVS analysis was carried out using a TA Instruments Q5000 Dynamic Vapor Sorption analyzer. Sample was loaded into a metal-coated quartz pan for analysis. The sample was analyzed at 25° C. after being equilibrated to 5% relative humidity (RH) in 10% RH steps from 5 to 95% RH (adsorption cycle) and from 95 to 5% RH (desorption cycle). The movement from one step to the next occurred either after satisfying the equilibrium criterion of 0.01% weight change in 60 minutes or, if the equilibrium criterion was not met, after 90 minutes.

As used herein with respect to the various analytical techniques described herein and data generated therefrom, the terms "substantially the same as" or "substantially similar to" is meant to convey that a particular set of analytical data is, within acceptable scientific limits, sufficiently similar to that disclosed herein such that one of skill in the art would appreciate that the crystal form of the compound is the same as that of the present invention. One of skill in the art would appreciate that certain analytical techniques, such as, for example, XRPD, $^1$H-NMR, LC/MS, IR, DSC, TGA, and Raman, will not produce exactly the same results every time due to, for example, instrumental variation, sample preparation, scientific error, etc. By way of example only, XRPD results (e.g., peak locations, intensities, and/or presence) may vary slightly from sample to sample, despite the fact that the samples are, within accepted scientific principles, the same crystalline form, and this may be due to, for example, preferred orientation or varying solvent or water content. It is well within the ability of those skilled in the art, looking at the data as a whole, to appreciate whether such differences indicate the same or a different form, and thus determine whether analytical data being compared to those disclosed herein are or are not substantially the same or similar to the solid form it is being compared with.

In this regard, and as is commonly practiced within the scientific community, it is not intended that the exemplary analytical data of the novel polymorphic forms of posiphen D-tartrate disclosed herein be met literally in order to determine whether comparative data represent the same form as those disclosed and claimed herein, such as, for example, whether each and every peak of an exemplary XRPD pattern of the novel polymorphic forms of posiphen D-tartrate disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form than the novel polymorphic forms of posiphen D-tartrate disclosed herein.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

"Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol;

esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

As used herein, the "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glutamine) and procaine. All of these salts may be prepared by conventional means from the corresponding free base compound by reacting, for example, the appropriate acid or base with the corresponding free base.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

A "subject in need thereof", as that term is used herein, indicates that the subject is suffering from a particular disease or disorder and has received a diagnosis or an indication of a particular disease or disorder from a medical practitioner or that the subject is at risk of developing the disease or disorder.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis As used herein, "(3aR)-1, 3a, 8-trimethyl-1, 2, 3, 3a, 8, 8a-hexahydropyrrolo (2, 3-b) indol-5-yl phenyl-carbamate tartrate" refers to "posiphen D-tartrate Form A" or "Form A", and are used interchangeably.

As used herein, "(3aR)-1, 3a, 8-trimethyl-1, 2, 3, 3a, 8, 8a-hexahydropyrrolo (2, 3-b) indol-5-yl phenyl-carbamate tartrate dihydrate" refers to "posiphen D-tartrate Form B" or "Form B", and are used interchangeably.

Crystalline Posiphen D-Tartrate Form A

Crystalline posiphen D-tartrate Form A was obtained in a crystalline solid form that is characterized by a unique XRPD pattern substantially as shown in FIG. 1. The broader nature of the peaks observed in the XRPD trace in FIG. 1 as well as FIG. 8 with respect to Form A indicate a semicrystalline nature. Posiphen D-tartrate Form A was found to be non-hydrated/solvated, as demonstrated by the representative TGA plot in FIG. 2, exhibiting only a 0.84% weight loss at 125° C. prior to decomposition at 153° C. Posiphen D-tartrate Form A exhibits a broad minor endotherm at about 81° C. and a major endotherm at about 146° C. as shown by the representative DSC trace in FIG. 2. This major endotherm is likely attributable to the melt of the material. Posiphen D-tartrate Form A is slightly hygroscopic based on DVS analysis, but no form change was observed following DVS or exposure to 75% relative humidity for 14 and 73 days (FIGS. 62, 63). As shown in FIG. 3, the sorption from exposure to gradually increasing relative humidity (5-95%) resulted in a total of 0.76% weight gain and desorption from exposure to gradually decreasing relative humidity (95-5%) resulted in a 0.81% total weight loss. The net weight change is −0.05%. These results show that Form A, the anhydrate, does not take up water and remains a stable anhydrate. Polarized light optical microscopy as shown in FIG. 4 revealed irregular crystalline blocks.

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate (Form A) is characterized by an X-ray powder diffraction pattern having characteristic peaks at 4.2, 8.5, 11.6, 11.8, 12.0, 12.8, 13.5, 14.4, 14.6, 14.9, 15.0, 15.2, 15.4, 16.2, 16.5, 17.0, 17.3, 17.9, 18.3, 18.6, 19.4, 19.6, 20.0, 20.4, 20.8, 21.0, 21.3, 21.8, 23.1, 23.6, 23.8, 24.2, 24.4, 24.8, 25.0, 25.2, 25.6, 25.8, 26.9, 27.9, 28.0, 28.4, 29.0, 29.5, 30.0, 30.4, 30.7, 31.3, 31.6, 32.3, 32.6, 33.0, 34.6, 35.0, 35.7, 36.8, 37.7, 38.6, in 2θ.

An exemplary listing of representative XRPD peaks and relative intensities of an embodiment of posiphen D-tartrate Form A can be found in Table 2.

TABLE 2

XRPD Peaks, Relative Intensities, and d-spacing Values of Posiphen D-tartrate Form A

| Diffraction angle 2θ | Relative Intensity % | d-spacing Value (Å) |
|---|---|---|
| 4.2 | 100 | 20.84 |
| 8.5 | 76 | 10.43 |
| 11.6 | 14 | 7.63 |
| 11.8 | 26 | 7.47 |
| 12.0 | 29 | 7.38 |

TABLE 2-continued

XRPD Peaks, Relative Intensities, and d-spacing Values of Posiphen D-tartrate Form A

| Diffraction angle 2θ | Relative Intensity % | d-spacing Value (Å) |
|---|---|---|
| 12.8 | 15 | 6.89 |
| 13.5 | 10 | 6.56 |
| 14.4 | 21 | 6.17 |
| 14.6 | 10 | 6.07 |
| 14.9 | 34 | 5.93 |
| 15.0 | 35 | 5.89 |
| 15.2 | 27 | 5.83 |
| 15.4 | 52 | 5.75 |
| 16.2 | 44 | 5.48 |
| 16.5 | 13 | 5.39 |
| 17.0 | 18 | 5.20 |
| 17.3 | 39 | 5.12 |
| 17.9 | 11 | 4.94 |
| 18.3 | 57 | 4.85 |
| 18.6 | 91 | 4.76 |
| 19.4 | 58 | 4.58 |
| 19.6 | 39 | 4.52 |
| 20.0 | 58 | 4.44 |
| 20.4 | 15 | 4.35 |
| 20.8 | 9 | 4.28 |
| 21.0 | 14 | 4.23 |
| 21.3 | 27 | 4.17 |
| 21.8 | 39 | 4.08 |
| 23.1 | 89 | 3.84 |
| 23.6 | 14 | 3.78 |
| 23.8 | 26 | 3.74 |
| 24.2 | 10 | 3.67 |
| 24.4 | 12 | 3.65 |
| 24.8 | 9 | 3.59 |
| 25.0 | 12 | 3.56 |
| 25.2 | 13 | 3.53 |
| 25.6 | 25 | 3.48 |
| 25.8 | 15 | 3.45 |
| 26.9 | 21 | 3.32 |
| 27.9 | 14 | 3.20 |
| 28.0 | 17 | 3.18 |
| 28.4 | 11 | 3.14 |
| 29.0 | 15 | 3.08 |
| 29.5 | 16 | 3.02 |
| 30.0 | 26 | 2.98 |
| 30.4 | 13 | 2.94 |
| 30.7 | 15 | 2.91 |
| 31.3 | 8 | 2.86 |
| 31.6 | 11 | 2.83 |
| 32.3 | 8 | 2.77 |
| 32.6 | 10 | 2.75 |
| 33.0 | 18 | 2.71 |
| 34.6 | 9 | 2.59 |
| 35.0 | 10 | 2.56 |
| 35.7 | 9 | 2.51 |
| 36.8 | 13 | 2.44 |
| 37.7 | 9 | 2.39 |
| 38.6 | 10 | 2.33 |

The solubility of posiphen D-tartrate Form A was determined in several solvents. The experiments were carried out by adding test solvents in aliquots to weighed portions of the respective forms. Whether dissolution had occurred was judged by visual inspection after addition of each solvent aliquot followed by brief sonication.

Solubility numbers were calculated by dividing the weight of the sample by the total volume of solvent used to dissolve the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than" if dissolution occurred on addition of the first solvent aliquot. All solubility measurements were carried out at room temperature.

In general, posiphen D-tartrate Form A displayed extremes of either very high or very low solubility depending on the solvent system. These results are shown in Table 3.

TABLE 3

Estimated Solubility of Posiphen D-tartrate Form A

| Sample ID | Solvent | Sample weight (mg) | Solvent amount (mL) | Solubility (mg/mL) |
|---|---|---|---|---|
| 1293-66-1 | Acetone | 3.0 | 2.000 | 2 |
| 1293-66-2 | Acetonitrile | 3.0 | 1.500 | 2 |
| 1293-66-3 | Dimethylformamide | 3.0 | 0.030 | >100 |
| 1293-66-4 | Ethyl acetate | 2.9 | 3.000 | <1 |
| 1293-66-5 | Heptanes | 3.1 | 3.000 | <1 |
| 1293-66-6 | Isopropyl alcohol | 3.1 | 2.500 | 1 |
| 1293-66-7 | Isopropyl ether | 3.1 | 3.000 | <1 |
| 1293-66-8 | Methanol | 3.2 | 0.030 | >100 |
| 1293-66-9 | Methyl ethyl ketone | 3.0 | 3.000 | <1 |
| 1293-66-10 | Tetrahydrofuran | 3.1 | 1.000 | 3 |
| 1293-66-11 | Water | 3.0 | 0.030 | >100 |
| 1293-66-12 | Chloroform | 3.0 | 3.000 | <1 |

Crystalline Posiphen D-Tartrate Form B

Figure 8:
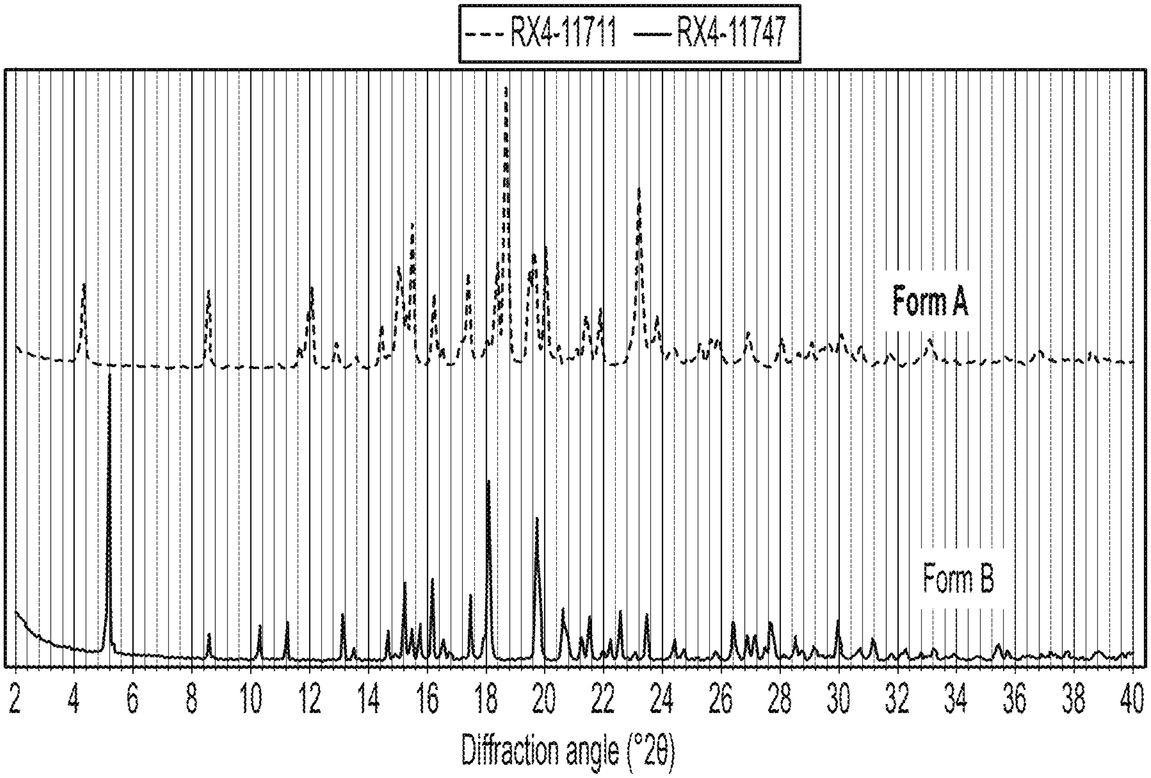
FIG. 8 shows a PXRD overlay of Form A (top trace) and Form B (bottom trace).
Figure 17:
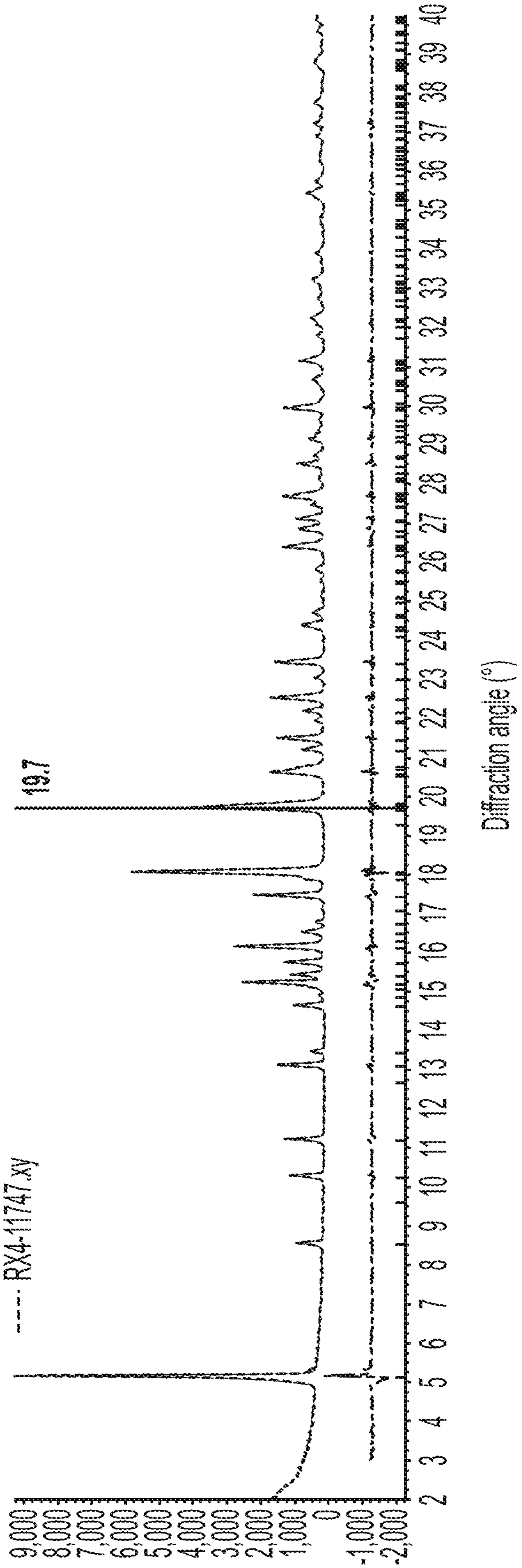
FIG. 17 shows the indexing of Form B. The blue trace is the obtained experimental data, the red trace is the fit, the grey trace is the fit residual, and the blue notches at the bottom show allowed peak positions.
Figure 20:
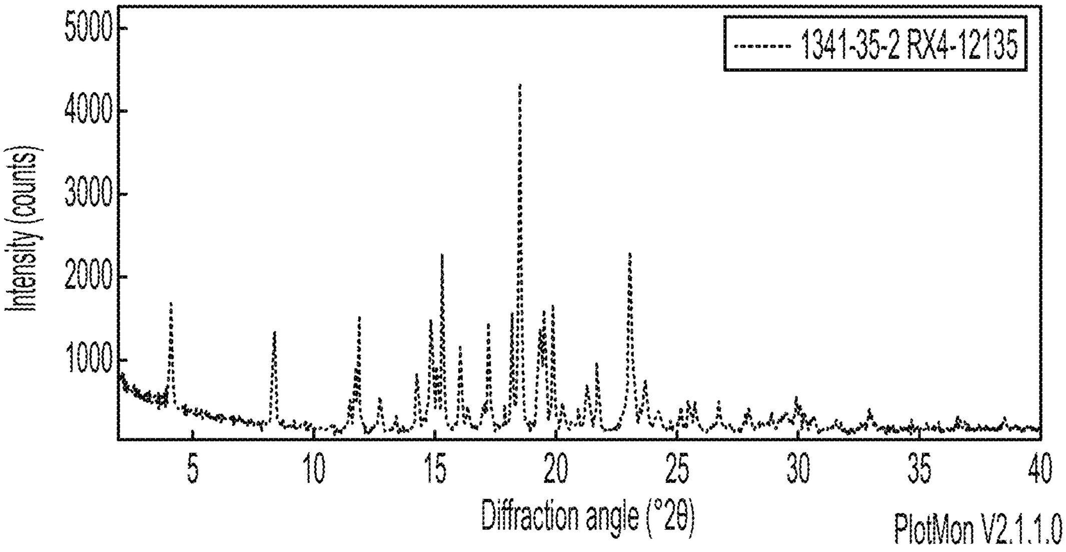
FIG. 20 shows a PXRD trace of Form A following milling with a steel ball for 30 minutes.
Figure 27:
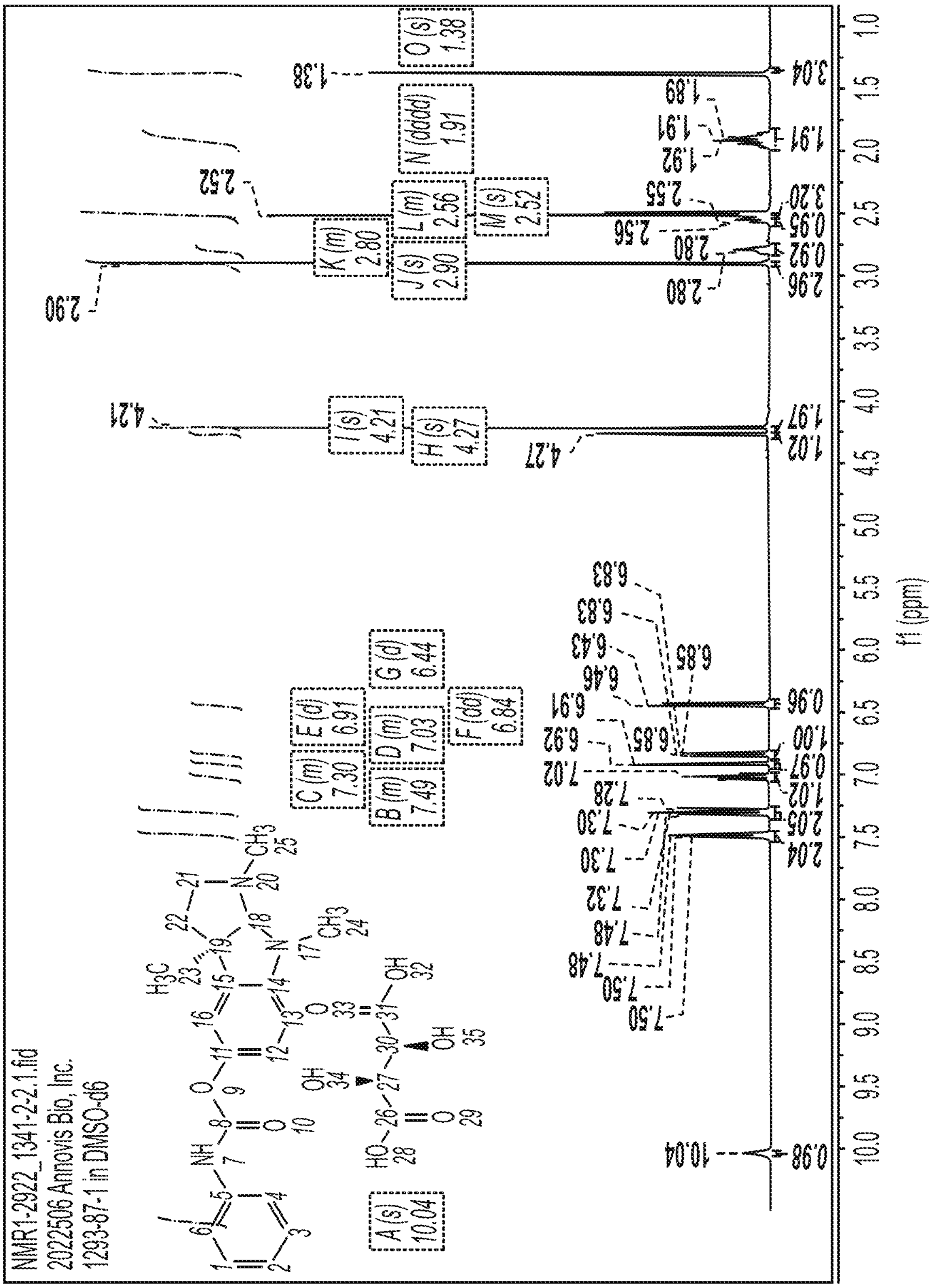
FIG. 27 shows a $^{1}$H-NMR spectrum of Form B recrystallized from water. The spectrum was acquired in DMSO-d6.

Dissolving Form A at a high concentration (~200 mg/mL) in water for an attempted slow evaporation resulted in spontaneous recrystallization of a new form designated Form B (FIG. 8). $^{1}$H NMR analysis of this form was consistent with the molecular structure of posiphen D-tartrate (FIG. 27). In comparing the PXRD traces of Form A and Form B, the peaks in the traces of Form B appeared sharper than that of Form A, indicating the highly crystalline nature of Form B versus the more semicrystalline Form A, indicated pattern was successfully indexed and the unit cell volume was consistent with a 1:1 posiphen D-tartrate salt with sufficient space to accommodate 2-3 moles of water. (FIG. 17). DSC analysis was carried out (FIG. 10), where a 7.1% weight loss starting at 76° C. in its TGA trace coupled with a major endotherm at 93° C. in the DSC trace indicates that the crystalline compound is a dihydrate possessing approximately 2 moles of water per molecule of salt. DVS analysis revealed a slightly hygroscopic nature with a negligible overall net weight gain (0.47% weight gain during sorption, 0.30% weight loss during desorption, 0.17% net weight gain) (FIG. 11). Post DVS PXRD revealed no form change had taken place during the analysis (FIG. 20). FTIR (FIG. 12) and Raman (FIG. 13) spectra were also obtained for Form B for reference.

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate dihydrate (Form B) is characterized by an X-ray powder diffraction pattern having characteristic peaks at 5.16, 8.56, 10.3, 11.24, 13.14, 13.48, 14.66, 15.24, 15.44, 15.76, 16.18, 16.54, 17.48, 17.94, 18.08, 19.72, 20.62, 20.76, 21.22, 21.5, 22.2, 22.54, 23.46, 24.4, 24.72, 26.4, 26.86, 27.14, 27.48, 27.7, 28.52, 28.74, 29.14, 29.96, 30.68, 31.14, 32.3, 33.26, 35.44, 37.24, and 37.74 in 2θ.

An exemplary listing of representative XRPD peaks of an embodiment of posiphen D-tartrate Form B can be found in Table 4.

TABLE 4

XRPD Peaks, Relative Intensities, and d-spacing Values of Posiphen D-tartrate Form B

| Diffraction Angle 2θ | Relative Intensity % | d-spacing Value (Å) |
|---|---|---|
| 5.16 | 100 | 17.13 |
| 8.56 | 10 | 10.33 |
| 10.3 | 13 | 8.59 |
| 11.24 | 14 | 7.87 |
| 13.14 | 17 | 6.74 |
| 13.48 | 6 | 6.57 |
| 14.66 | 11 | 6.04 |
| 15.24 | 28 | 5.81 |
| 15.44 | 12 | 5.74 |
| 15.76 | 14 | 5.62 |
| 16.18 | 29 | 5.48 |
| 16.54 | 9 | 5.36 |
| 17.48 | 24 | 5.07 |
| 17.94 | 9 | 4.94 |
| 18.08 | 63 | 4.91 |
| 19.72 | 51 | 4.50 |
| 20.62 | 19 | 4.31 |
| 20.76 | 9 | 4.28 |
| 21.22 | 9 | 4.19 |
| 21.5 | 17 | 4.13 |
| 22.2 | 8 | 4.00 |
| 22.54 | 19 | 3.94 |
| 23.46 | 17 | 3.79 |
| 24.4 | 9 | 3.65 |
| 24.72 | 5 | 3.60 |
| 26.4 | 15 | 3.38 |
| 26.86 | 10 | 3.32 |
| 27.14 | 10 | 3.29 |
| 27.48 | 6 | 3.25 |
| 27.7 | 15 | 3.22 |
| 28.52 | 10 | 3.13 |
| 28.74 | 5 | 3.11 |
| 29.14 | 6 | 3.06 |
| 29.96 | 14 | 2.98 |
| 30.68 | 6 | 2.91 |
| 31.14 | 9 | 2.87 |
| 32.3 | 5 | 2.77 |
| 33.26 | 5 | 2.69 |
| 35.44 | 7 | 2.53 |
| 37.24 | 5 | 2.41 |
| 37.74 | 5 | 2.38 |

Figure 9:
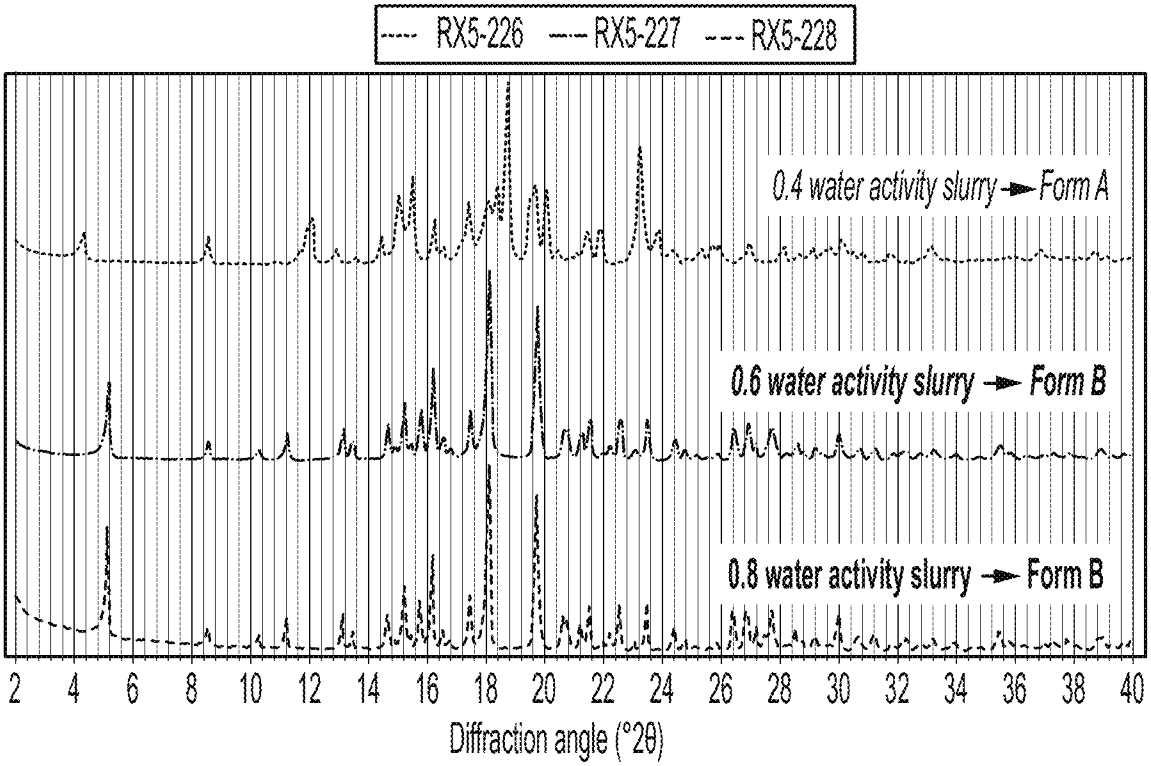
FIG. 9 show a PXRD overlay of Form A produced from a 0.4 water activity slurry (top trace), Form B produced from a 0.6 water activity slurry (middle trace), and Form B produced from a 0.8 water activity slurry (bottom trace).

Having identified a dihydrate, water activity (WA) slurries were setup with Form A to identify the critical water activity required for the conversion of anhydrous Form A to the dihydrate Form B. Acetonitrile was utilized as the solvent system based on the solubility of the API and the accessible range of WA with small amounts of water to keep the solubility reasonable. Slurries were conducted using primarily Form A along with seeds of Form B. While Form A prevailed at 0.4 WA, conversion to Form B was observed at 0.6 and 0.8 WA (FIG. 9). Based on these results, the critical water activity needed for conversion to Form B is between 0.4 to 0.6 at room temperature.

To investigate the robustness of the dihydrate Form B, a sample was dried overnight at 50° C. in a vacuum oven. PXRD analysis revealed an unchanged pattern. Thus, no form change had taken place and that there was no loss of water from the dihydrate. A neat sample of Form B was also milled in a Retsch mill for 30 minutes to assess the impact of mechanical stress, and no change in form or crystallinity was observed, all pointing to Form B being a fairly robust and stable dihydrate as well as stable to mechanical stress.

As such, Form B appears to be a fairly robust dihydrate of posiphen D-tartrate formed at a critical water activity between 0.4 and 0.6 at room temperature. The solubility of Form B was determined in water, and was found to be only a fraction of Form A at 14 mg/mL.

Amorphous Posiphen D-Tartrate

Amorphous posiphen D-tartrate was prepared via lyophilization from water. Modulated-DSC of this sample revealed an endotherm at 69° C., possibly originating from the dehydration of adsorbed moisture as observed by the 2.5% weight loss by 125° C. from its TGA trace. A glass transition temperature ($T_g$) of 86° C. was also identified from the reversible heat flow. Given the 2.5% water adsorbed during ambient storage, amorphous posiphen D-tartrate appears to be hygroscopic in nature, and the dry $T_g$ would likely be higher than what is currently observed.

Figure 24:
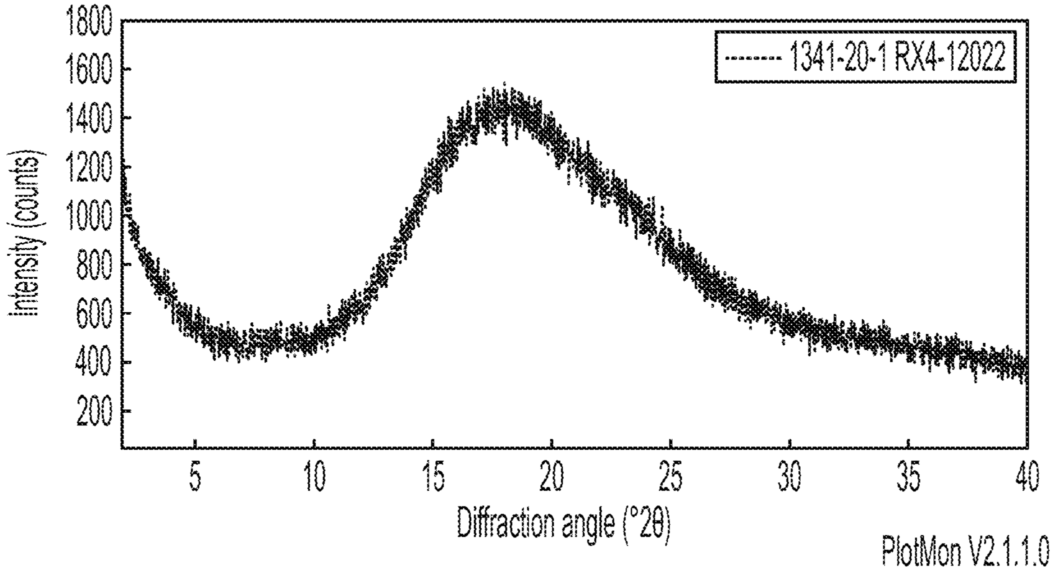
FIG. 24 shows a PXRD trace of amorphous posiphen D-tartrate obtained via lyophilization.

As can be seen from the differences in XRPD patterns in FIG. 8, crystalline posiphen D-tartrate Forms A and B each exhibit unique crystallographic properties, and each represents a distinct crystal form of the compound. As can be seen in FIG. 24, XRPD trace of the amorphous posiphen D-tartrate is a broad, featureless diffraction pattern, as is typical of a non-crystalline form.

The invention in various exemplary embodiments relates to pure or substantially pure crystalline posiphen D-tartrate Form A, crystalline posiphen D-tartrate Form B, or crystalline posiphen D-tartrate Form A having the peaks of metastable Pattern C. By way of example, in one embodiment, the invention may relate to a batch or lot of posiphen D-tartrate which is 50% or more, such as 60% or more, 75% or more, 90% or more, 95% or more, 98% or more, or 99% or more, crystalline posiphen D-tartrate Form A, crystalline posiphen D-tartrate Form B, crystalline posiphen D-tartrate having the peaks of metastable Pattern C, or amorphous posiphen D-tartrate. In further exemplary embodiments, the invention relates to pharmaceutical compositions and/or formulations comprising pure or substantially pure crystalline posiphen D-tartrate Form A, crystalline posiphen D-tartrate Form B, crystalline posiphen D-tartrate having the peaks of metastable Pattern C, or amorphous posiphen D-tartrate.

In further embodiments, the invention relates to crystalline posiphen D-tartrate Form A, crystalline posiphen D-tartrate Form B, crystalline posiphen D-tartrate having the peaks of metastable Pattern C, and/or amorphous posiphen D-tartrate in a mixture, such as a mixture of crystalline posiphen D-tartrate Forms A, B and/or A having the peaks of metastable Pattern C, and/or amorphous posiphen D-tartrate, or in a mixture comprising additional known or as yet unknown solid forms of posiphen D-tartrate. By way of example only, the mixture may comprise one or more of crystalline posiphen D-tartrate Forms A, B, and A having the peaks of metastable Pattern C, and/or amorphous posiphen D-tartrate.

Figure 2:
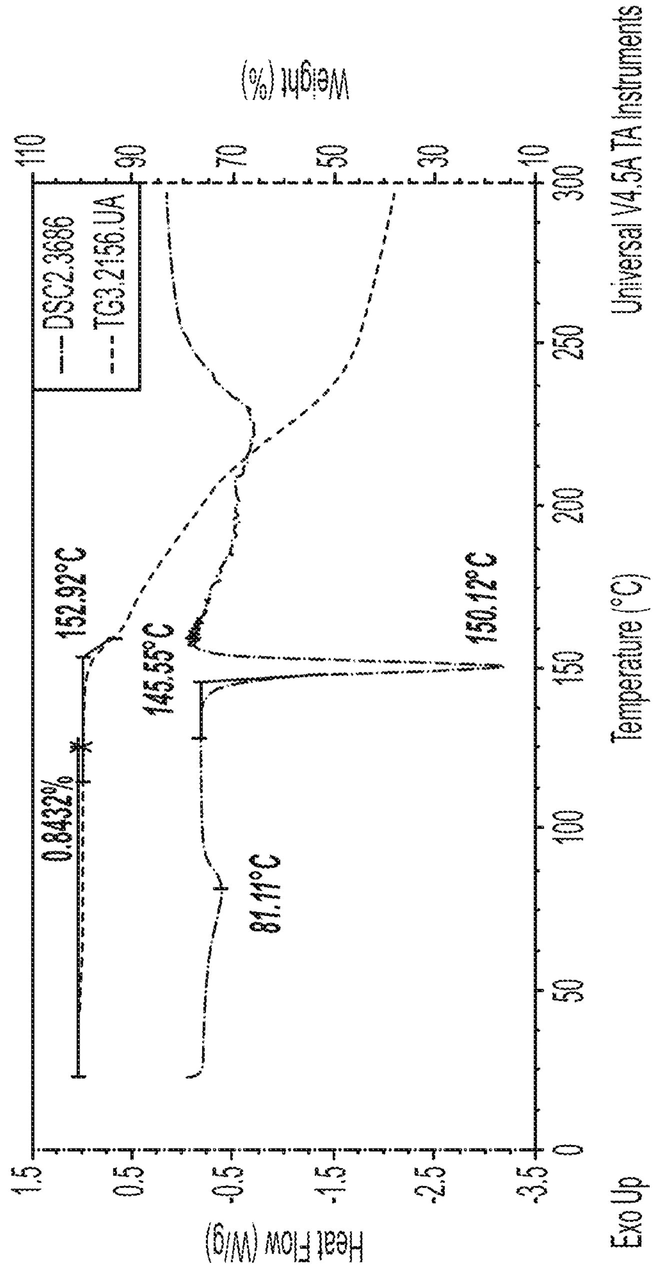
FIG. 2 shows a DSC and TGA trace of posiphen D-tartrate, lot BPR-21-114-B1-19.
Figure 3:
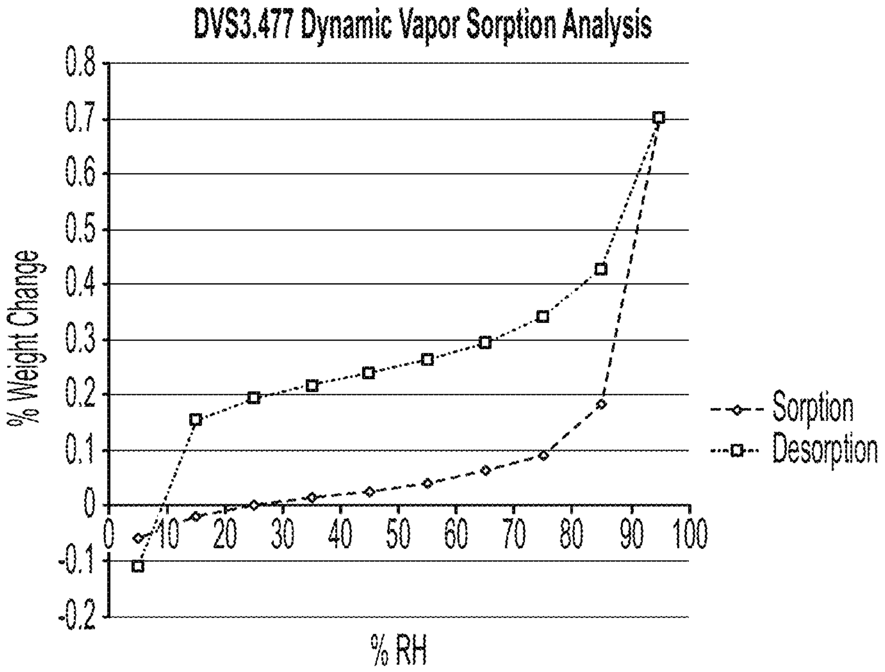
FIG. 3 shows a DVS trace of posiphen D-tartrate.
Figure 4:
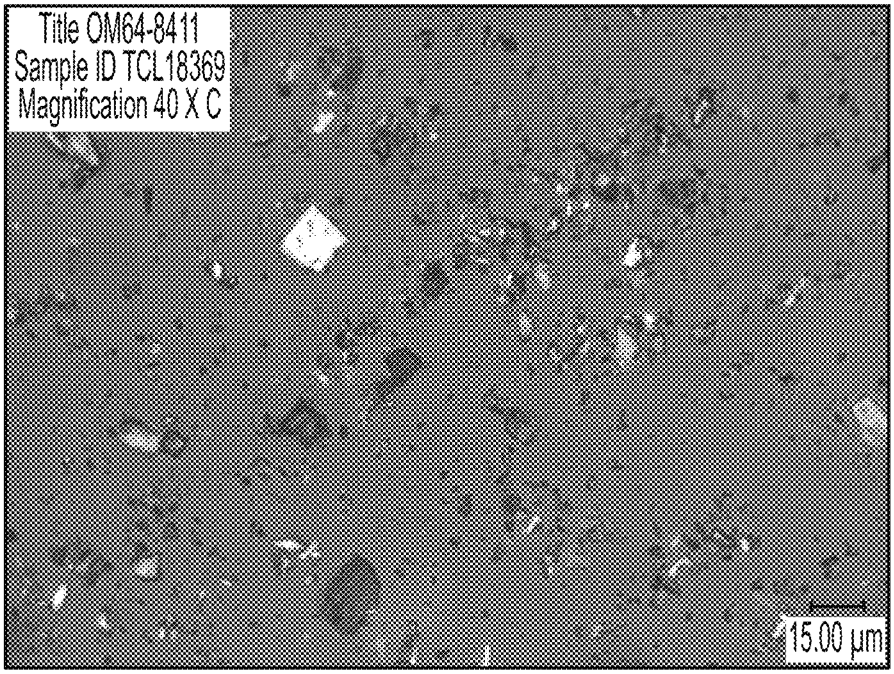
FIG. 4 shows a polarized light microscopy (PLM) image of posiphen D-tartrate, lot BPR-21-114-B1-19.
Figure 5:
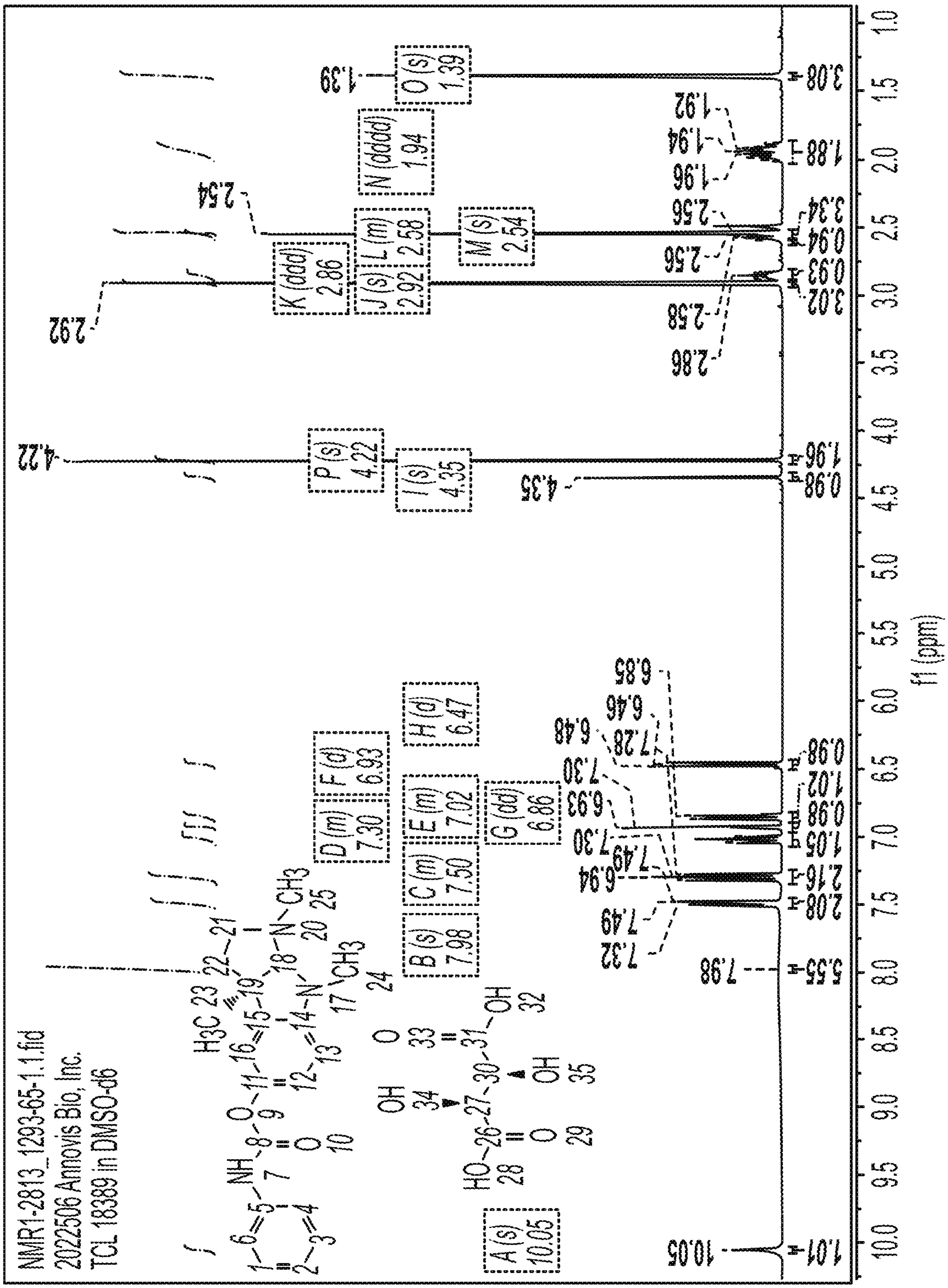
FIG. 5 shows a $^{1}H$-NMR spectrum of posiphen D-tartrate, lot BPR-21-114-B1-19 taken in in DMSO-d6.
Figure 6:
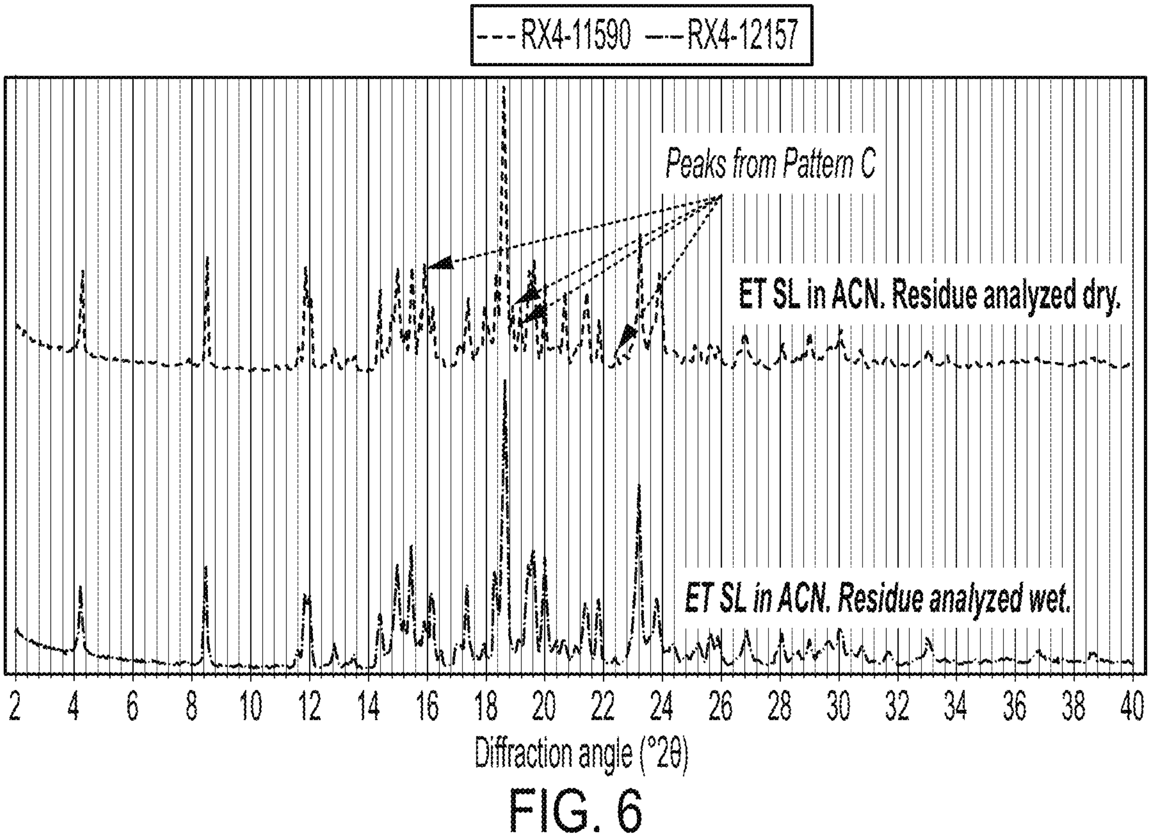
FIG. 6 shows a PXRD overlay of Form A having the peaks of Pattern C produced from an elevated temperature slurry in acetonitrile analyzed wet (bottom trace) compared to the same residue analyzed dry (top trace).
Figure 18A:
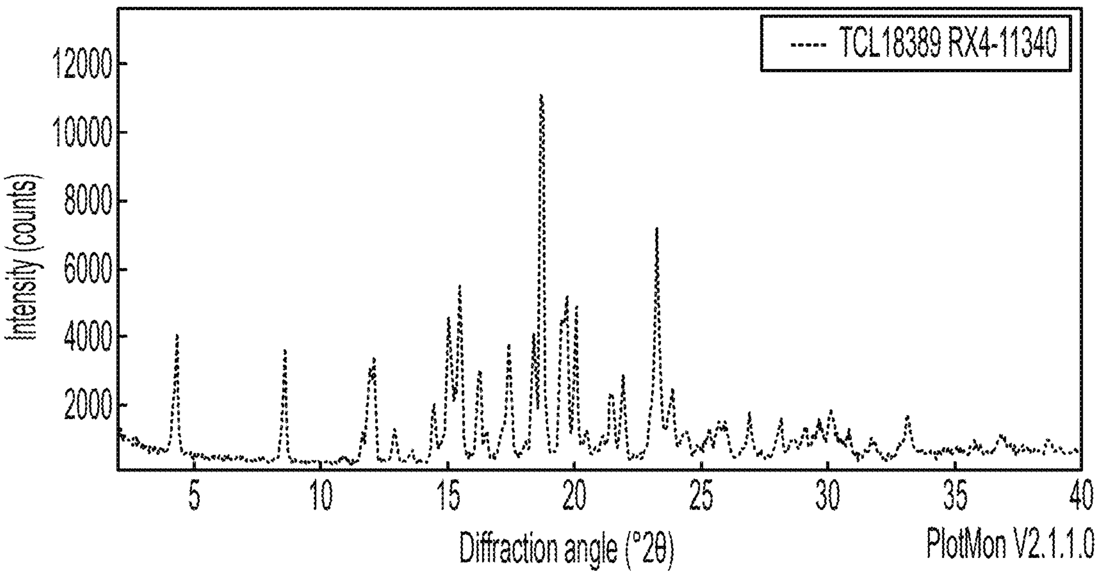
FIG. 18A shows a PXRD trace of crystalline Form A.
Figure 18B:
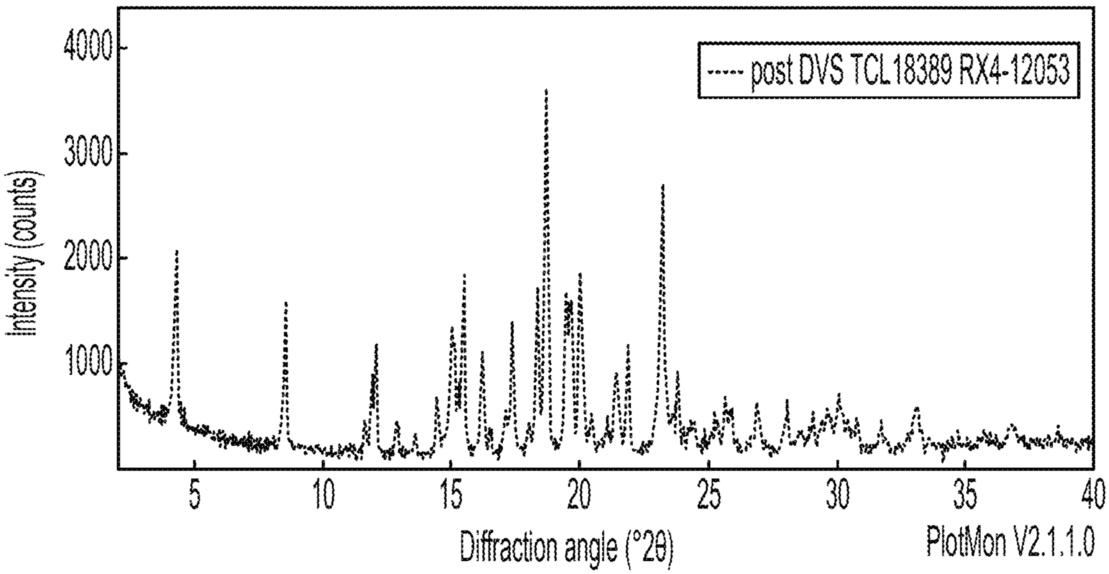
FIG. 18B shows a PXRD trace of crystalline Form A following DVS.
Figure 19:
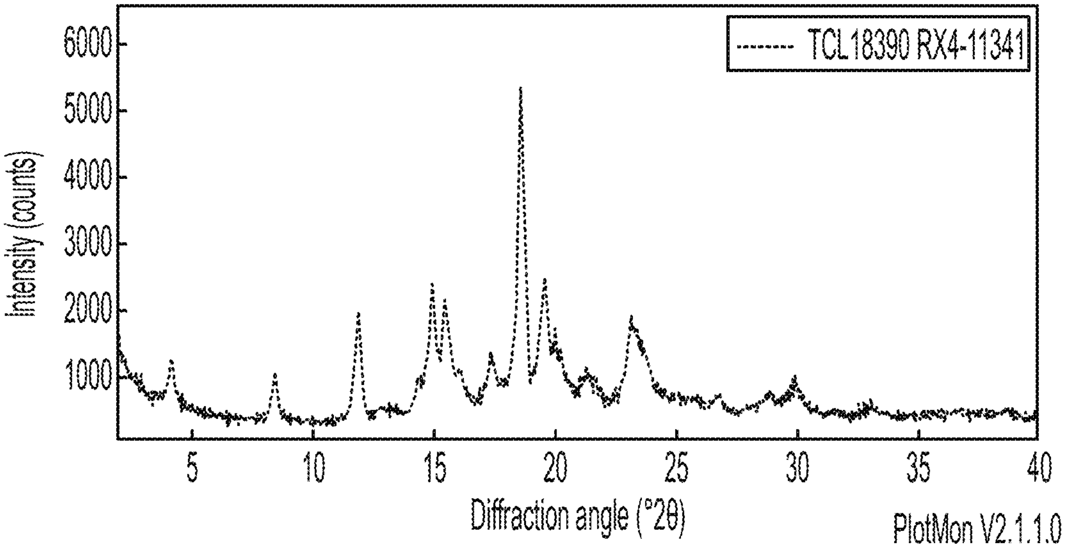
FIG. 19 shows a PXRD trace of Form A that is poorly crystalline.

In one embodiment the crystalline (3aR)-1, 3a, 8-trimethyl-1, 2, 3, 3a, 8, 8a-hexahydropyrrolo (2, 3-b) indol-5-yl phenyl-carbamate tartrate (Form A) has characteristics consistent with those described in Table 2 and/or Table 6 and/or FIG. 2 and/or FIG. 3 and/or FIG. 4 and/or FIG. 5 and/or FIG. 18A and/or FIG. 18B and/or as prepared according to a method as herein described and/or claimed and/or according to Example 2 and/or Example 8.

Figure 10:
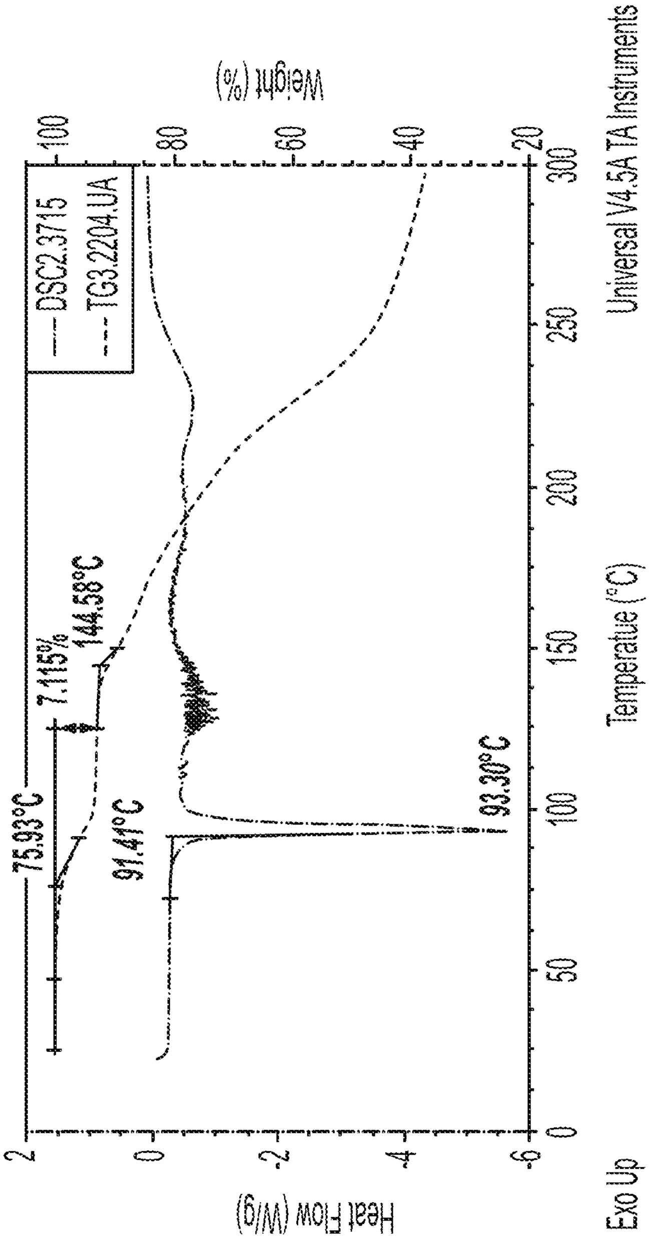
FIG. 10 shows a DSC and TGA trace of Form B.
Figure 11:
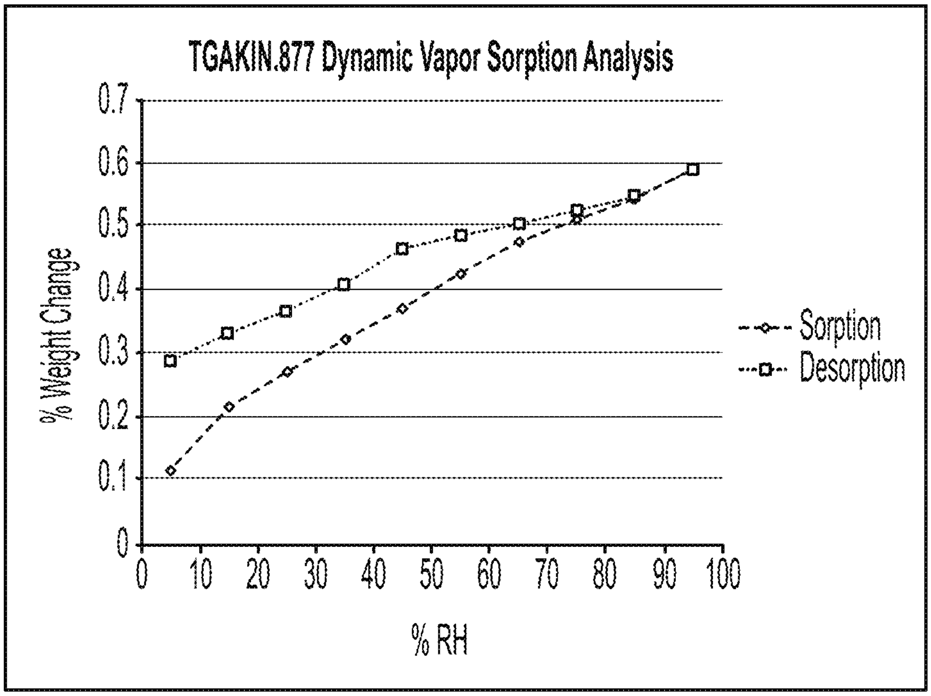
FIG. 11 shows a DVS trace of Form B.
Figure 12:
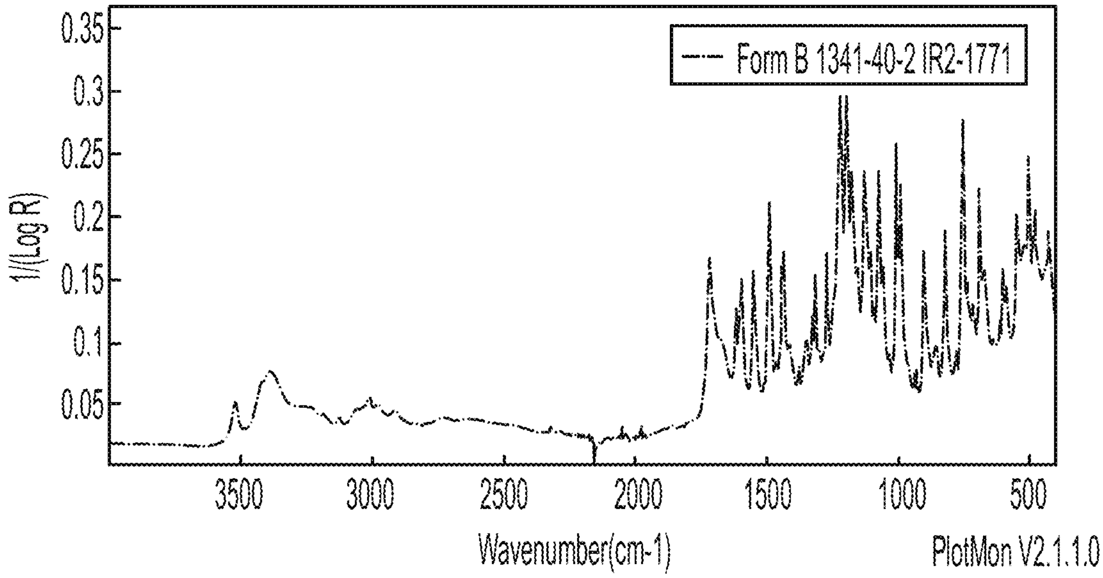
FIG. 12 shows an FTIR spectrum of Form B.
Figure 13:
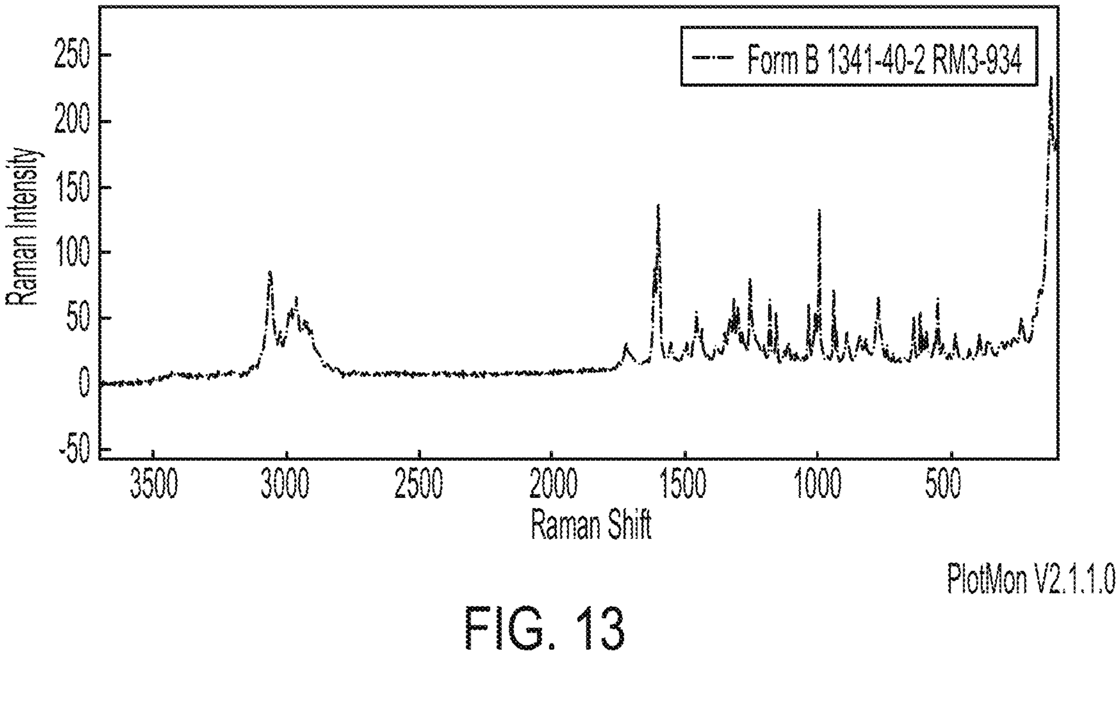
FIG. 13 shows a Raman spectrum of Form B.
Figure 21:
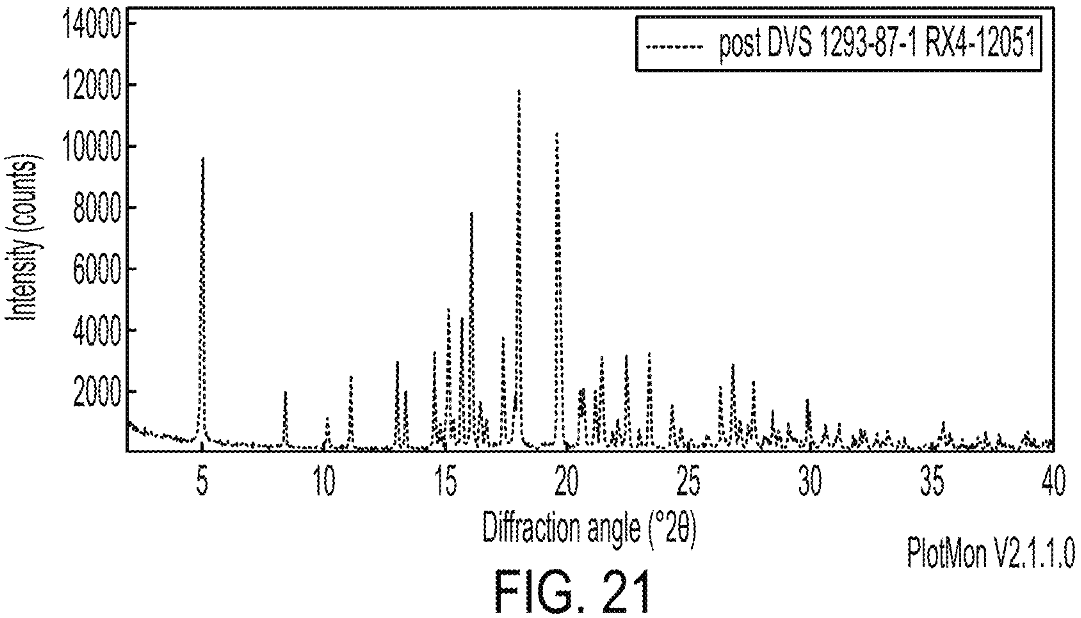
FIG. 21 shows a PXRD trace of Form B.
Figure 22:
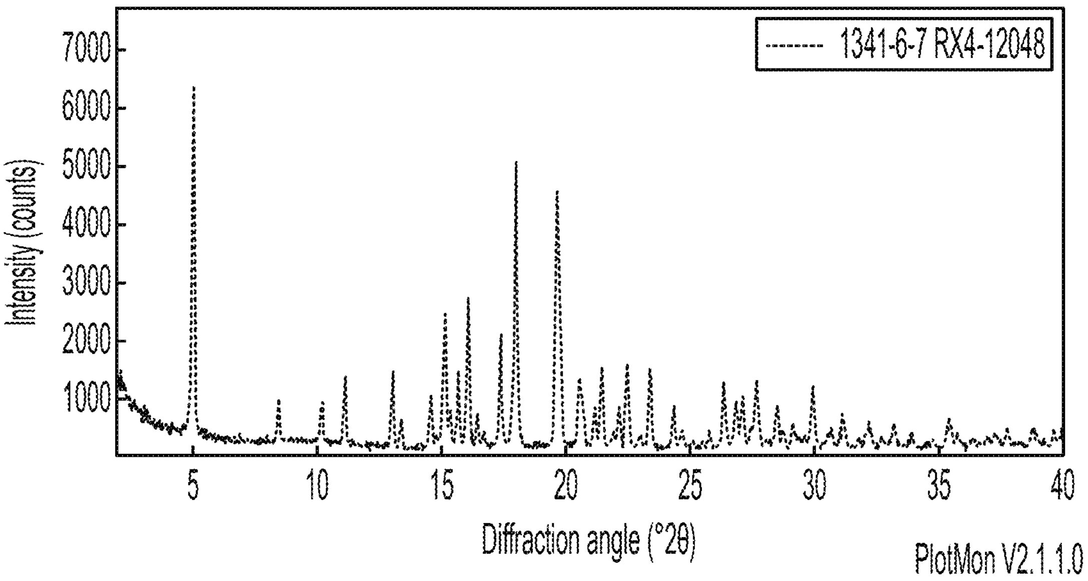
FIG. 22 shows a PXRD trace of Form B that was dried in a vacuum oven at 50° C. uncapped for 18 hours.

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate dihydrate (Form B) has characteristics consistent with those described in Table 4 and/or Table 7 and/or FIG. 10 and/or FIG. 11 and/or FIG. 12 and/or FIG. 13 and/or FIG. 21 and/or FIG. 27 and/or as prepared according to a method as herein described and/or claimed and/or according to Example 3 and/or Example 8.

Figure 14:
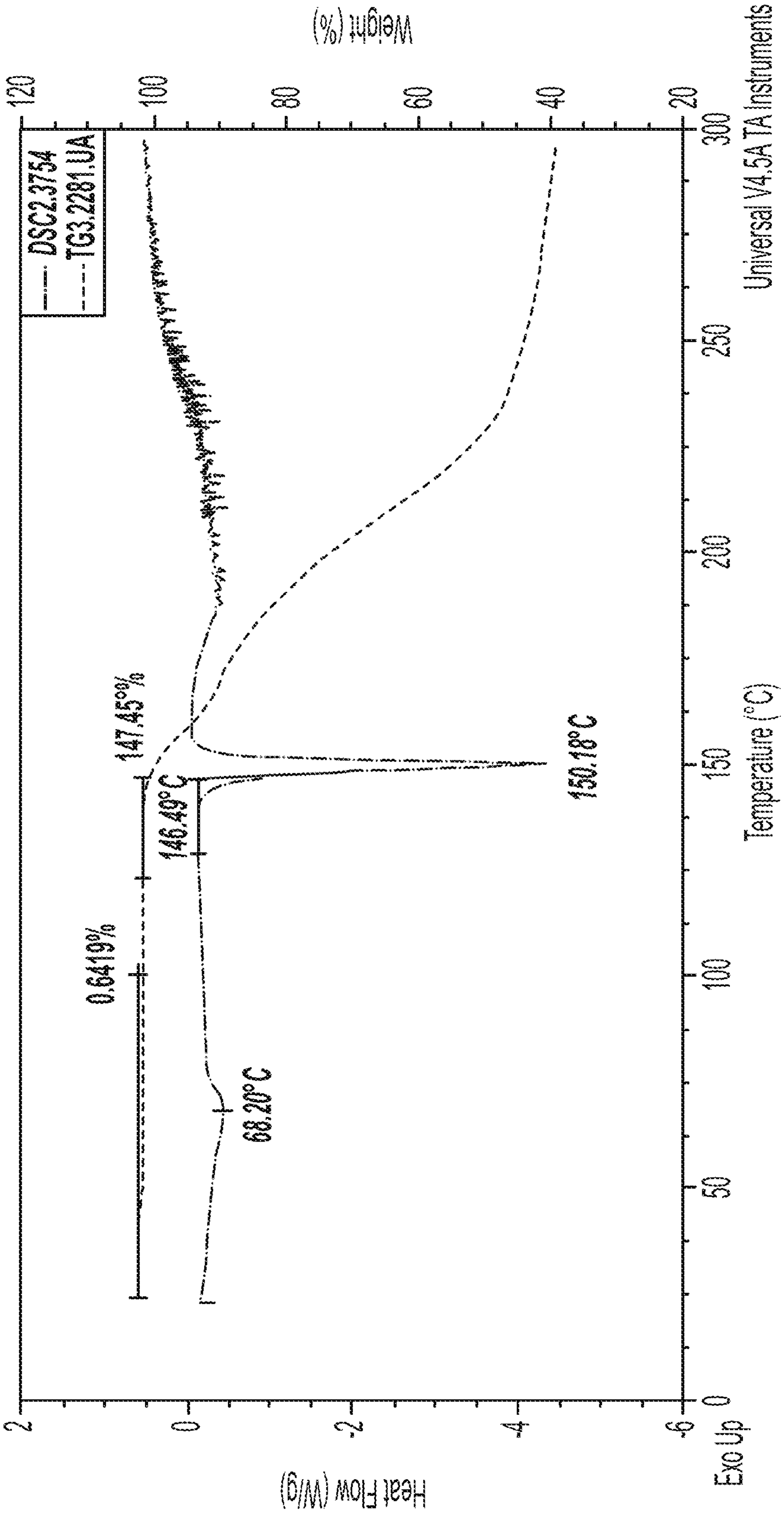
FIG. 14 shows a DSC and TGA trace of Form A having the peaks of Pattern C.

In one embodiment the crystalline (3aR)-1, 3a, 8-trimethyl-1, 2, 3, 3a, 8, 8a-hexahydropyrrolo (2, 3-b) indol-5-yl phenyl-carbamate tartrate (Form A) having the peaks of metastable Pattern C has characteristics consistent with those described in Table 2 and/or FIG. 14 as prepared according to a method as herein described and/or claimed and/or according to Example 8.

In one embodiment, there is provided substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate, or posiphen D-tartrate Form B that has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC).

Any method may be used to analyze and characterize the purity of posiphen D-tartrate. For example, analytical methods for analyzing the purity of the posiphen D-tartrate Form B include, but are not limited to high-performance liquid chromatography (HPLC), chiral HPLC, gas chromatography, and quantitative nuclear magnetic resonance.

HPLC can be used to separate the components of a mixture into its separate components, including any detectable impurities. Briefly, a sample with a mobile phase is introduced into a column packed with particles of a stationary phase wherein the compound and its components each interact with the stationary phase based on the relative affinity of the components for the stationary phase to separate the mixture into its separate components. The components are separated based on the time take to elute from the column wherein the elution time for each component differs based on the relative affinity for and interactions with the stationary phase. Normal phase HPLC utilizes a nonpolar mobile phase and a polar stationary phase whereas reverse phase HPLC utilizes a polar mobile phase and a nonpolar stationary phase. In a mixture involving stereoisomers, chiral HPLC can also be used to determine the chirality and enantiomeric excess of the mixture. Chiral HPLC involves the use of a chiral stationary phase that contains a single enantiomer wherein the stereoisomers contained in the mixture to be separated each interact differently with the chiral stationary phase to accomplish the separation.

Following synthesis of pharmaceutical products such as active pharmaceutical ingredients, there may be residual solvents left over from the manufacturing process. The presence of residual solvents may have an effect on the properties of the pharmaceutical product such as the potential toxicity of the product, solubility, crystallinity, and bioavailability. Gas chromatography, in particular headspace gas chromatography, can be used to analyze and quantify residual solvents in pharmaceutical products. Headspace sampling involves analysis of the gas layer of a dissolved sample in a vial versus direct injection of the dissolved sample itself. The components to be analyzed by headspace gas chromatography are required to be highly volatile. The injected headspace sample passes through a column containing a stationary phase while being carried by a nonreactive or inert gas wherein the various components of the mixture interact differently with the stationary phase of the column based on their affinity and elute at different rates based on these interactions.

Quantitative nuclear magnetic resonance (Q-NMR) is used to determine the purity of small molecules and can be used to obtain the concentration, purity, and mass fraction of the analyte of interest. In Q-NMR, the peak areas of the analyte are compared to the peak areas of a known amount of an internal calibrant. The measured peak area of a particular signal is proportional to the number of nuclei (e.g., protons) present. The purity of the analyte can be determined by comparing the peak areas of the analyte with those of the internal calibrant. The internal calibrant should have at least one peak that does not overlap with the analyte. On occasion, the calculated purity (e.g., mass fraction of analyte) may exceed the theoretical maximum of 100% Potential reasons for >100% purity values may include, but are not limited to differences in residual water content between the internal calibrant and the analyte, or the use of an internal calibrant that is significantly less pure than the target analyte.

In one embodiment, the present invention provides a method of inhibiting production of amyloid precursor protein in a cell, comprising contacting the cell with crystalline posiphen D-tartrate Form A, crystalline posiphen D-tartrate Form B, crystalline posiphen D-tartrate having the peaks of metastable Pattern C, amorphous posiphen D-tartrate and any combination thereof. As used herein, "inhibiting" means decreasing the amount or concentration of amyloid precursor protein. "Inhibition" also refers to halting or reducing the production of amyloid protein precursor, wherein the concentration of amyloid protein precursor is reduced. Thus, the inhibition of production of amyloid precursor protein can be measured, for example, by comparing the amount of amyloid precursor protein produced by cells after contacting the cells with the crystalline posiphen D-tartrate Form A, crystalline posiphen D-tartrate Form B, crystalline posiphen D-tartrate having the peaks of metastable Pattern C, amorphous posiphen D-tartrate and any combination thereof, with the amount of amyloid precursor protein produced by control cells that have not been contacted with the crystalline posiphen D-tartrate Form A, crystalline posiphen D-tartrate Form B, crystalline posiphen D-tartrate having the peaks of metastable Pattern C, amorphous posiphen D-tartrate and any combination thereof. In one embodiment, the cell that is contacted with the compound is in vivo, ex vivo, or in vitro. The cell of this invention can be a mammalian cell, desirably a human cell.

In a desirable embodiment, the compounds inhibit production of amyloid precursor protein, $A\beta_{1-40}$, and/or $A\beta_{1-42}$ in a cell or a mammal by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ in a cell or a mammal by at least 2, 5, 10, 20, or 50-fold compared to a buffer control, as measured using standard assays such as those described herein.

As used herein, "contacting" means exposure of at least one cell to a compound of the present invention. The cell of this invention can be, but is not limited to, a neural cell or supporting cell (e.g., glial or astrocyte). The term "neural cell" is defined as any cell that can be located in the central or peripheral nervous system or is a precursor or derivative thereof, including, for example, but not limited to, neuronal cells, glial cells, neural stem cells, neuronal stem cells and neuroblasts. The cell can be contacted in vitro with the compound, for example, by adding the compound to the culture medium (by continuous infusion, by bolus delivery, or by changing the medium to a medium that contains the compound), or the cell can be contacted with the compound in vivo (e.g., by local delivery, systemic delivery, intravenous injection, bolus delivery, or continuous infusion). In vitro contact may be preferred, for example, for measuring the effect of the compound on a population of cells. In vivo contact would be employed for inhibiting production of amyloid precursor protein in a subject in need of such inhibition, (e.g., a subject) with a neurodegenerative disease or disorder, for example, Alzheimer's disease.

The subject of this invention can be any mammal that produces amyloid precursor protein, such as a primate and more desirably, a human. The subject of this invention can also be domesticated animals, such as cats, dogs, etc., livestock (e.g., cattle, horses, pigs, sheep, goats, etc.), and laboratory animals (e.g., mouse, rabbit, rat, guinea pig, etc.).

The duration of contact with a cell or population of cells is determined by the time the compound is present at physiologically effective levels or at presumed physiologically effective levels in the medium or extracellular fluid bathing the cell or cells. Desirably, the duration of contact is 1-48 hours and, more desirably, for 24 hours, but such time would vary based on the half-life of the compound.

In another embodiment, the present invention also provides a method of inhibiting production of amyloid precursor protein in a subject, comprising administering to the subject an effective amount of the crystalline posiphen D-tartrate Form A, crystalline posiphen D-tartrate Form B, crystalline posiphen D-tartrate having the peaks of metastable Pattern C, amorphous posiphen D-tartrate and any combination thereof in a pharmaceutically acceptable carrier, whereby the compound inhibits production of amyloid precursor protein in the subject.

In a desirable embodiment, the compounds of the invention inhibit production of amyloid precursor protein, $A\beta_{1-40}$, and/or $A\beta_{1-42}$ in the subject or in a sample from the subject by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ in the subject or in a sample from the subject by at least 2, 5, 10, 20, or 50-fold compared to a buffer control, as measured using standard assays such as those described herein.

The compounds of the present invention can be administered in vivo to a subject in need thereof by commonly employed methods for administering compounds in such a way to bring the compound in contact with cells. The compounds of the present invention can be administered orally, parenterally, transdermally, extracorporeally, topically or the like, although oral or parenteral administration is typically desired. Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intra-articular and intratracheal routes. Additionally, the compound can be administered via a slow release or sustained release system such that a constant dosage is maintained. The compounds can also be administered using polymer-based delivery systems, including, for example, microencapsulation, which techniques are well known in the art.

The dosage of the compound varies depending on the weight, age, sex and condition of the subject as well as the method and route of administration. As an example, the dosage of the compound is from about 0.1 mg/kg to about 100 mg/kg of body weight. The lower limit for the dosage can be about 0.1, 0.5, 1, 2, 5, 10, 15, 20, 25, 30, or 40 mg/kg and the upper limit can be about 10, 15, 20, 25, 30, 40, 50, 60, 70, 80, 90, or 100 mg/kg. Any lower limit can be used with any upper limit. More desirably, the compound is administered in vivo in an amount of about 1 to about 20 mg/kg. Therefore, in some embodiments, the compound can be administered in an amount of about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or about 20 mg/kg. The administration of each dosage could be hourly, daily, every other day, weekly, biweekly, or monthly. Thus, an administration regimen could include long-term, daily treatment. By "long-term" is meant at least two weeks and, desirably, several weeks, months, or years of duration. Necessary modifications in this dosage range may be determined by one of ordinary skill in the art using only routine experimentation given the teachings herein. See Remington's Pharmaceutical Sciences (Martin, E. W., ed., latest edition), Mack Publishing Co., Easton, Pa. The dosage can also be adjusted by the individual physician in the event of any complication.

The compounds can be administered conventionally as compositions containing the active compound as a predetermined quantity of active material calculated to produce the desired therapeutic effect in association with the required diluent (i.e., carrier or vehicle). Depending on the intended mode of administration, the compound can be in pharmaceutical compositions in the form of solid, semi-solid or liquid dosage forms, such as, for example, tablets, suppositories, pills, capsules, powders, liquids, suspensions, lotions, creams, gels, or the like, desirably in unit dosage form suitable for single administration of a precise dosage. The compositions will include, as noted above, an effective amount of the selected compound in combination with a pharmaceutically acceptable carrier and, in addition, may include other medicinal compounds, pharmaceutical compounds, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of about 1 ng/kg/day to 100 mg/kg/day. Thus, in some embodiments, the pharmaceutical compositions may be administered to deliver a dose of about 1 ng/kg/day, 2 ng/kg/day, 5 ng/kg/day, 10 ng/kg/day, 20 ng/kg/day, 25 ng/kg/day, 50 ng/kg/day, 100 ng/kg/day, 200 ng/kg/day, 250 ng/kg/day, 500 ng/kg/day, 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9, mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day, 60 mg/kg/day, 65 mg/kg/day, 70 mg/kg/day, 75 mg/kg/day, 80 mg/kg/day, 85 mg/kg/day, 90 mg/kg/day, 95 mg/kg/day, or about 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically based formulations.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a “unit dose” is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington’s Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode or administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, “additional ingredients” include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other “additional ingredients” that may be included in the pharmaceutical compositions of the invention are known in the art and described, for example in Genaro, ed. (1985, Remington’s Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject or used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying compounds, pH buffering compounds and the like, for example, sodium acetate, sorbitan monolaurate, triethanolamine sodium acetate, triethanolamine oleate, etc. Thus, the compositions are administered in a manner compatible with the dosage formulation and in a therapeutically effective amount. As discussed above, precise amounts of active ingredient required to be administered depend on the judgment of the practitioner and are peculiar to each individual.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled or sustained release formulations of a composition of the invention may be made using conventional technology, in addition to the disclosure set forth elsewhere herein. In some cases, the dosage forms to be used can be provided as slow or controlled release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled release formulations known to those of ordinary skill in the art, including those described herein, can be readily selected for use with the compositions of the invention.

Controlled release of an active ingredient can be stimulated by various inducers, for example pH, temperature, enzymes, water, or other physiological conditions or compounds. The term "controlled release component" in the context of the present invention is defined herein as a compound or compounds, including, but not limited to, polymers, polymer matrices, gels, permeable membranes, liposomes, nanoparticles, or microspheres or a combination thereof that facilitates the controlled release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective, to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid, Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 relates to directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way of a dermally acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (e.g., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulfoxides (such as dimethylsulfoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, antioxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (e.g., olive oil/PEG7), biovera oil, wax (e.g., jojoba wax), squalene, myristate (e.g., isopropyl myristate), triglycerides (e.g., caprylic triglyceride), Solulan 98, cocoa butter, shea butter, alcohol (e.g., behenyl alcohol), stearate (e.g., glycerol-monostearate), chelating agents (e.g., EDTA), propylene glycol, SEPIGEL (Seppic, Inc., Fairfield, N.J.), silicone and silicone derivatives (e.g., dimethicone, cyclomethicone), vitamins (e.g., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

In another embodiment, the present invention provides a method of treating a disorder associated with abnormal production of amyloid precursor protein, such as, for example, dementia in a subject, comprising administering to the subject an effective amount of the crystalline posiphen D-tartrate Form A, crystalline posiphen D-tartrate Form B, crystalline posiphen D-tartrate having the peaks of metastable Pattern C, amorphous posiphen D-tartrate and any combination thereof in a pharmaceutically acceptable carrier, whereby the compound treats the disorder in the subject. As used herein, the term "dementia" describes a neurodegenerative disorder that results from an organic brain disease in which a subject experiences usually irreversible deterioration of intellectual faculties with accompanying emotional disturbances. An example of dementia includes, but is not limited to, Alzheimer's disease. An example of another disorder that can be treated by the methods of this invention includes, but is not limited to, cerebral amyloidosis. In a desirable embodiment, a compound used for the treatment of dementia improves a symptom associated with dementia or Alzheimer's, stabilizes a symptom, or delays the worsening of a symptom. In other desirable embodiments, the compound increases the lifespan of a subject compared to the average life-span of corresponding subjects not administered the compound. In yet other desirable embodiments, the compound is used to prevent or delay the onset of dementia or Alzheimer's disease.

In another embodiment, the present invention also provides a method of inhibiting production of the amyloid precursor protein in Down syndrome comprising administering an effective amount of (3aR)-1, 3a, 8-trimethyl-1, 2, 3, 3a, 8, 8a-hexahydropyrrolo (2, 3-b) indol-5-yl phenylcarbamate tartrate dihydrate (Form B) to a subject in need thereof. While not intending to be bound by one theory of the invention, the following may help to explain the relationship between the amyloid precursor protein in Down syndrome and that of Alzheimer's disease. In persons with Alzheimer's disease, amyloid fibrils (aggregates of Aβ protein subunits) are deposited in the brain. A similar process occurs at an earlier age in people with Down Syndrome. Rumble et al. "Amyloid Aβ protein and its precursor in Down's syndrome and Alzheimer's disease," *N. Engl. J. Med.,* 320(22):1446-1452 (Jun. 1, 1989). Thus, the formation of the amyloid fibrils in Down Syndrome can be inhibited in a similar manner as it does in Alzheimer's disease. Further, the cerebrovascular amyloid protein from a case of adult Down syndrome has been isolated and purified. Amino acid sequence analysis showed it to be homologous to that of the beta protein of Alzheimer's disease. Glenner G & Wong C W "Alzheimer's disease and Down's syndrome: sharing of a unique cerebrovascular amyloid fibril protein," *Biochem Biophys Res Commun.,* 122(3):1131-5 (Aug. 16, 1984).

In general, an "effective amount" of a compound is that amount needed to achieve the desired result or results. Thus, for example, administering to a subject (e.g., a human) with Alzheimer's disease an effective amount of a compound of the present invention can result in slowing, stopping, or even possibly reversing the deterioration of the subject's intellectual faculties and other accompanying neurological signs and symptoms. Therefore, the inhibition of the production of amyloid precursor protein, by the methods of the present invention, treats the subject with Alzheimer's disease. The effective amount of the compound needed to treat dementia is from about 0.5 mg to about 200 mg. The lower limit for the effective amount of the compound can be about 0.5, 1, 2, 5, 10, 20, 30, 40, 50, 100, or 150 mg, and the upper limit can be about 50, 60, 70, 80, 90, 100, 110, 120, 130, 140, 150, 160, 170, 180, 190, or 200 mg. Any lower limit can be used with any upper limit. In one embodiment, when the subject is a human, the effective amount of compound to treat dementia is from about 0.5 to about 100 mg. In another embodiment, crystalline posiphen D-tartrate Form A can be used in these amounts to treat dementia. In a desired embodiment, posiphen D-tartrate Form B can be used in these amounts to treat dementia in a subject.

Any form of (3aR)-1, 3a, 8-trimethyl-1, 2, 3, 3a, 8, 8a-hexahydropyrrolo (2, 3-b) indol-5-yl phenyl-carbamate tartrate can be delivered using formulations and doses from, for example, U.S. Pat. No. 7,786,162 (oral formulations and doses), U.S. Pat. No. 8,258,172 (transdermal formulations and doses), U.S. Pat. No. 10,383,851 (formulations and oral dosage in gelatin capsule form), U.S. Pat. No. 11,400,075 (formulations and doses), US 2018/0228771 (intravenous and intraocular administration).

In a further embodiment, the present invention relates to a method of binding an amyloid precursor protein messenger RNA 5' untranslated region (5'UTR) in a cell, comprising contacting the cell with crystalline posiphen D-tartrate Form A, crystalline posiphen D-tartrate Form B, crystalline posiphen D-tartrate having the peaks of metastable Pattern C, amorphous posiphen D-tartrate and any combination thereof, whereby the compound binds the amyloid precursor protein messenger RNA 5' untranslated region in the cell, thereby inhibiting amyloid protein production. The amyloid precursor protein messenger RNA 5'UTR confers translational control of βAPP protein synthesis. In one embodiment, posiphen D-tartrate Form A can be used to bind the amyloid precursor protein with messenger RNA 5' UTR. In a desired embodiment, posiphen D-tartrate Form B can be used to bind to an amyloid precursor protein messenger RNA 5' untranslated region in a cell. In a desirable embodiment, at least 30, 50, 60, 70, 80, 90, 95, or 100% of the amyloid precursor protein mRNA in a cell is bound by the compound.

In a further embodiment, the present invention relates to a method of inhibiting translation of an amyloid precursor protein messenger RNA in a cell, comprising contacting the cell with crystalline posiphen D-tartrate Form A, crystalline posiphen D-tartrate Form B, crystalline posiphen D-tartrate having the peaks of metastable Pattern C, amorphous posiphen D-tartrate and any combination thereof, whereby the compound binds the amyloid precursor protein messenger RNA 5' and/or 3' untranslated region in the cell, or binds a protein that interacts with the amyloid precursor protein messenger RNA 5' and/or 3' untranslated region in the cell, or alters a process, either indirectly or directly, such as glycosylation or phosphorylation that then changes the binding of a specific regulatory protein to amyloid precursor protein messenger RNA 5' and/or 3' untranslated region in the cell, thereby inhibiting amyloid protein production. In one embodiment, posiphen D-tartrate Form A can be used to inhibit the translation of the amyloid precursor protein with messenger RNA. In a desired embodiment, posiphen D-tartrate Form B can be used to inhibit the translation of the amyloid precursor protein messenger RNA by interfering with the post-transcriptional regulation of the amyloid precursor protein RNA in a cell. In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein.

The present invention also provides a method of screening a compound for the ability to inhibit production of amyloid precursor protein, $A\beta_{1-40}$, and/or $A\beta_{1-42}$, comprising (a) contacting the cell with crystalline posiphen D-tartrate Form A, crystalline posiphen D-tartrate Form B, crystalline posiphen D-tartrate having the peaks of metastable Pattern C, amorphous posiphen D-tartrate and any combination thereof, and (b) detecting a decrease in amyloid precursor protein, $A\beta_{1-40}$, and/or $A\beta_{1-42}$ production in a cell contacted with the compound as compared to the amount of amyloid precursor protein, $A\beta_{1-40}$, and/or $A\beta_{1-42}$ production in a control cell not contacted with the compound, whereby decreased production of amyloid precursor protein, $A\beta_{1-40}$, and/or $A\beta_{1-42}$ in the cell identifies the compound as having the ability to inhibit the production of amyloid precursor protein, $A\beta_{1-40}$, and/or $A\beta_{1-42}$ in a cell. As shown in the Examples section below, a person of skill in the art can measure the amount of βAPP, $A\beta_{1-40}$, and/or $A\beta_{1-42}$ production in a control population of cells and compare the production of βAPP, $A\beta_{1-40}$, and/or $A\beta_{1-42}$ in a population of cells contacted with a compound to be screened by the methods of the present invention. A decrease in the production of βAPP, $A\beta_{1-40}$, and/or $A\beta_{1-42}$ in a population of cells contacted with a compound as compared to the production of βAPP, $A\beta_{1-40}$, and/or $A\beta_{1-42}$ in a population of control cells identifies the compound as having the ability to inhibit production of amyloid precursor protein, $A\beta_{1-40}$, and/or $A\beta_{1-42}$. In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein.

The present invention further provides a method of screening a compound for the ability to inhibit amyloid precursor protein production by binding an amyloid precursor protein messenger RNA 5' untranslated region, comprising (a) contacting the messenger RNA with the compound; (b) detecting the binding of the compound to the amyloid precursor protein-messenger RNA 5' untranslated region; and (c) detecting the inhibition of amyloid precursor protein production from an amyloid precursor protein-messenger RNA 5' untranslated region, thereby identifying a compound having the ability to inhibit amyloid precursor protein messenger RNA 5' untranslated region. The binding of the compound to the amyloid precursor protein messenger RNA 5' untranslated region inhibits R amyloid precursor protein (βAPP) from the messenger RNA by directly preventing the binding of the ribosomal translational subunit with the mRNA through steric hindrance. The detection of binding of a compound to the 5' UTR of the amyloid precursor protein messenger RNA can be carried out by methods standard in the art for detecting the binding of substances to nucleic acids such as RNA. The detection of inhibition of amyloid precursor protein production upon contact with the compound can be carried out by the methods provided in the Examples herein, as well as protocols well known in the art. The messenger RNA can be in a cell or in a cell-free environment (e.g., a cell-free translation system). In a desirable embodiment, at least 30, 50, 60, 70, 80, 90, 95, or 100% of the amyloid precursor protein mRNA in a cell is bound by the compound.

The present invention further provides a method of screening a compound for the ability to inhibit amyloid precursor protein, $A\beta_{1-40}$, and/or $A\beta_{1-42}$ production by inhibiting translation of the amyloid precursor protein messenger RNA, comprising (a) contacting the cell with the compound; and (b) detecting the inhibition of amyloid precursor protein, $A\beta_{1-40}$, and/or $A\beta_{1-42}$ production from an amyloid precursor protein RNA, thereby identifying a compound having the ability to inhibit amyloid precursor protein messenger RNA translation. In another embodiment, the screening method further comprises after step (a) detecting the amount of the amyloid precursor protein-messenger RNA. In one embodiment, the amount of amyloid precursor protein mRNA is not inhibited by the compound or is inhibited by less than 80, 80, 50, 40, 30, 20, or 10%. In this case, the compound primarily or only inhibits the translation of amyloid precursor protein. It is also contemplated that in other embodiments a compound may inhibit both transcription and translation of amyloid precursor protein or inhibit only transcription of amyloid precursor protein. While not meant to limit the invention to any particular mechanism of action, the inhibition of translation by the compound can result from the binding of the compound to the amyloid precursor protein messenger RNA 5' and/or 3'-untranslated region(s) inhibiting β amyloid precursor protein (βAPP) from the messenger RNA by directly preventing the binding of the ribosomal translational subunit with the mRNA through steric hindrance or by inhibiting the binding of an important regulatory protein, or the binding of the compound to the regulatory protein or by the compound modifying an important regulatory protein such that it no longer can interact with the amyloid precursor protein RNA. The direct detection of binding of a compound to the 5' and/or 3' UTR(s) of the amyloid precursor protein messenger RNA can be carried out by methods standard in the art for detecting the binding of substances to nucleic acids such as RNA, such as NMR or mass spectroscopy. The detection of inhibition of amyloid precursor protein production upon contact with the compound can be carried out by the methods provided in the Examples herein, as well as protocols well known in the art. The messenger RNA can be in a cell or in a cell-free environment (e.g., a cell-free translation system). In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein. In yet another desirable embodiment, at least 30, 50, 60, 70, 80, 90, 95, or 100% of the amyloid precursor protein mRNA in a cell is bound by the compound. In still another embodiment, at least 30, 50, 60, 70, 80, 90, 95, or 100% of the compound is directly or indirectly bound to an amyloid precursor protein messenger RNA 5' or 3' untranslated region or to an RNA binding protein that interacts with the amyloid precursor protein messenger RNA 5' or 3' untranslated region.

In another embodiment, the invention relates to a method of screening a compound for the ability to inhibit amyloid protein production by eliciting a change in reporter gene expression, comprising:

(a) contacting a cell transfected with a reporter gene containing the 5' and/or 3' UTR(s) of the amyloid precursor protein messenger RNA with the compound, and (b) detecting a decrease in reporter gene expression or activity; thereby identifying a compound having the ability to inhibit amyloid precursor protein messenger RNA translation.

In a desirable embodiment, the compound inhibits reporter gene expression or activity by at least 30, 50, 60, 70, 80, 90, 95, or 100% compared to a buffer control, as measured using standard assays such as those described herein. In another desirable embodiment, the compound inhibits reporter gene expression or activity by at least 2, 5, 10, 20, or 50-fold compared to a buffer control, as measured using standard assays such as those described herein.

The compounds used in the screening methods of this invention can be, but are not limited to, the crystalline posiphen D-tartrate Form A, crystalline posiphen D-tartrate Form B, crystalline posiphen D-tartrate having the peaks of metastable Pattern C, amorphous posiphen D-tartrate and any combination thereof. In various embodiments, the compound is crystalline posiphen D-tartrate Form A, crystalline posiphen D-tartrate Form B, or a mixture thereof. In various embodiments of any of the methods of the invention, the compound is crystalline posiphen D-tartrate Form A, crystalline posiphen D-tartrate Form B, or a mixture thereof.

In a desirable embodiment of any of the aspects of the invention, the compound inhibits cholinesterase activity, such as acetylcholinesterase or butyrylcholinesterase activity, by less than 80, 70, 60, 50, 40, 30, 20, 10, or 5% (in order of increasing preference) relative to a buffer only control. In other desirable embodiments, inhibition of cholinesterase activity, such as acetylcholinesterase or butyrylcholinesterase activity, by the compound is at least 2-, 5-, 10-, 20-, 50-, or 100-fold less than the inhibition of cholinesterase activity by the corresponding amount of crystalline posiphen D-tartrate Form A. In other desirable embodiments, inhibition of cholinesterase activity, such as acetylcholinesterase or butyrylcholinesterase activity, by crystalline posiphen D-tartrate Form A is at least 2-, 5-, 10-, 20-, 50-, or 100-fold less than the inhibition of cholinesterase activity by the corresponding amount of crystalline posiphen D-tartrate Form B. In yet other desirable embodiments, the compound is substantially free of cholinesterase inhibitory activity. Inhibition of cholinesterase activity can be measured using any standard assay. For example, the assay and the in vivo mouse model described in U.S. Pat. No. 4,791,107, which is incorporated by reference in its entirety, or the in vivo mouse model described herein can be used.

In other desirable embodiments of any of the aspects of the invention, the compound results in a less than 20-, 10-, 5-, or 2-fold increase in the amount of released lactate dehydrogenase (a marker of cell viability and integrity) relative to the amount of released lactate dehydrogenase in the absence of the compound or in the presence of a buffer control. In still other desirable embodiments, the amount of compound that is administered to a subject per kg body weight of the subject does not cause tremors or death when administered in the in vivo mouse model described herein. In yet other desirable embodiments, less than 80, 70, 60, 50, 40, 30, 20, 10, or 5% of the neuronal cells contacted with the compound are killed by the compound. In another desirable embodiment, the dose of the compound is equal to or greater than 1 mg/kg of body weight, 5 mg/kg, or 10 mg/kg.

In other desirable embodiments of any of the aspects of the invention, the compound inhibits production of amyloid precursor protein, $A\beta_{1-40}$, and/or $A\beta_{1-42}$ by at least 30, 50, 60, 70, 80, 90, 95, or 100% compared to a buffer control. In another embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, and inhibits cholinesterase activity by less than 80, 70, 60, 50, 40, 30, 20, 10, or 5% relative to a buffer only control. In other desirable embodiments, the compound inhibits intracellular and/or extracellular APP or Aβ production. In yet other desirable embodiments, the compound inhibits production of amyloid precursor protein in a cell or mammal by at least 2-, 5-, 10-, 20-, or 50-fold more than it inhibits cholinesterase activity in the cell or mammal. In still other desirable embodiments, the amount of compound required to inhibit production of amyloid precursor protein in a cell or mammal by 50% ($IC_{50}$ value) is at least 2-, 5-, 10-, 20-, 50-, or 100-fold less than the amount of compound required to inhibit cholinesterase activity by 50% ($IC_{50}$ value) in the cell or mammal, as measured using standard assays.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1—Characterization Techniques

Differential Scanning Calorimetry

Differential scanning calorimetry (DSC) analysis was carried out using a TA Instruments Q2500 Discovery Series instrument. The instrument temperature calibrations were performed using indium. The DSC cell was kept under a nitrogen purge of ~50 mL per minute during the analysis. The sample was placed in a standard, crimped aluminum pan and heated from approximately 25° C. to 300° C. at a rate of 10° C. per minute.

Dynamic Vapor Sorption

Dynamic vapor sorption analysis was carried out using a TA Instruments Q5000 Dynamic Vapor Sorption analyzer. The sample was loaded into a metal-coated quartz pan for analysis. The sample was analyzed at 25° C. after being equilibrated to 5% relative humidity (RH) in 10% RH steps from 5 to 95% RH (adsorption cycle) and from 95 to 5% RH (desorption cycle). The movement from one step to the next occurred either after satisfying the equilibrium criterion of 0.01% weight change in 60 minutes or, if the equilibrium criterion was not met, after 90 minutes. The percent weight change values were calculated using Microsoft Excel®.

$^{1}$H-Nuclear Magnetic Resonance $^{1}$H nuclear magnetic resonance (NMR) spectra were acquired on a Bruker Avance NEO 400 spectrometer. Samples were prepared by dissolving material in the specified deuterated solvent. The solutions were placed into individual 5-mm NMR tubes for subsequent spectral acquisition. The temperature controlled (298K) $^{1}H$ NMR spectra acquired on the Avance NEO 400 utilized a 5-mm cryoprobe operating at an observing frequency of 400.18 MHz. Each spectrum was processed using TopSpin version 4.1.4 and referenced to the chemical shift of the residual solvent peak.

Polarized Light Microscopy

Optical microscope images were acquired using a Leica DM2500P polarizing microscope equipped with a PAXcam3 digital camera controlled by PAX-it! 2 v.1.4.3 software. The performance of the microscope was verified with a certified MRS-3XY standard. Samples were placed on the stage under the 40× objective and illuminated with transmitted light.

Powder X-Ray Diffraction

Powder X-ray diffraction (PXRD) was carried out using a Rigaku SmartLab X-Ray Diffractometer configured in Bragg-Brentano reflection geometry equipped with a beam stop and knife edge to reduce incident beam and air scatter. The PXRD data collection parameters are outline in the following Table 5:

TABLE 5

PXRD Data Collection Parameters

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44/45 | Step Size (°) | 0.02 |
| Detector | D/teX Ultra 250 (XR1/XR3/XR5) HyPix-3000 (XR4) | Scan Speed (°/min) | 6 |
| Monochromator | Ni foil Cu Kβ Filter | Spinning (rpm) | 11 |
| Incident Slit (°) | 1/3 | Sample Holder | Low-background Si |

Thermogravimetric Analysis

Thermogravimetric analysis (TGA) was carried out using a TA Instruments Q5500 Discovery Series instrument. The instrument balance was calibrated using class M weights and the temperature calibration was performed using alumel. The nitrogen purge was ~10 mL per minute at the balance and ~25 mL per minute at the furnace. The sample was placed into a pre-tared platinum pan and heated from approximately 25° C. to 300° C. at a rate of 10° C. per minute.

Raman Spectroscopy

Raman spectroscopic analysis was performed using a Nicolet iS50 Raman module that was equipped with a 1064 nm near-infrared laser. The system was configured with an indium gallium arsenide (InGaAs) detector and a calcium fluoride ($CaF_2$) beamsplitter. Each sample was placed onto the automated XYZ stage and analyzed using a laser power that was adjusted to optimize the signal intensity while avoiding damage to the sample. Raman spectra were collected with 256 signal-averaged scans at a resolution of 2 $cm^{-1}$ over the spectral range from 3700 $cm^{-1}$ to 100 $cm^{-1}$. Data acquisition and processing were performed using OMNIC v9.11 software.

Fourier Transform Infrared Spectroscopy

IR spectroscopic analysis was performed using a Thermo Scientific model iS50 Fourier-transform (FT) IR spectrophotometer equipped with a deuterated triglycine sulfate (DTGS) detector, a potassium bromide (KBr) beamsplitter, and a Polaris™ long-life IR source. A diamond attenuated total reflectance (ATR) sampling accessory having a spectral range of 4000 $cm^{-1}$ to 400 $cm^{-1}$ was used. Each spectrum was the result of 128 co-added scans acquired at 2 $cm^{-1}$ resolution. A single beam background scan of air was acquired before the sample scan, allowing presentation of the spectra in log 1/R units. Wavelength calibration was performed using polystyrene. OMNIC v9.11 software package (Thermo-Nicolet) was used to acquire, process, and evaluate the spectral data.

Example 2—Synthesis of (3aR)-1, 3a, 8-trimethyl-1, 2, 3, 3a, 8, 8a-hexahydropyrrolo (2, 3-b) indol-5-yl phenyl-carbamate Tartrate (Posiphen D-Tartrate Form A)

Figure 32:
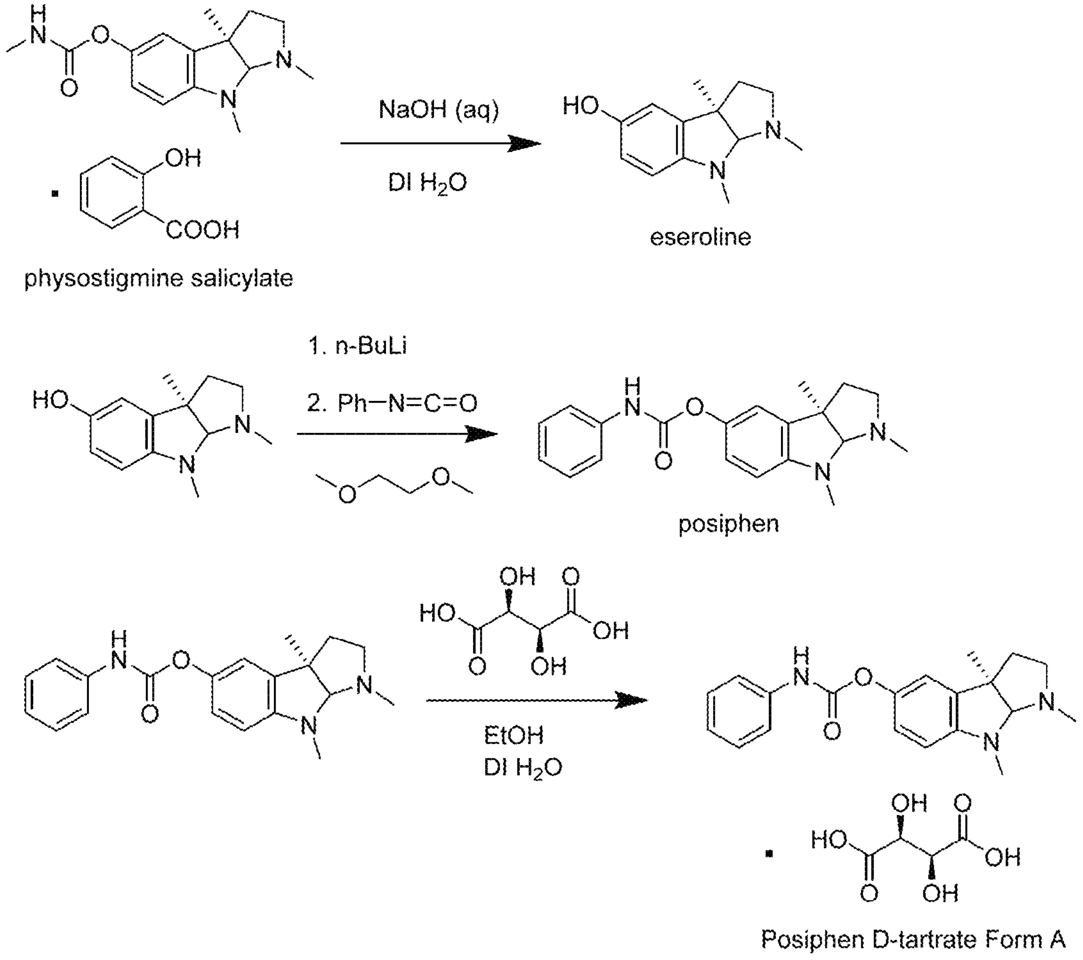
FIG. 32 is a reaction scheme showing the synthesis of Form A.

A reaction scheme is shown in FIG. 32, which shows the conversion of physostigmine salicylate into the corresponding eseroline via hydrolyzing the physostigmine with an alkali metal hydride. The eseroline is subsequently treated with a strong organic base and reacted with an isocyanate (e.g., phenyl isocyanate) to yield posiphen. The corresponding tartaric acid salt is obtained via treatment with an equimolar amount of D-tartaric acid.

Eseroline Base Synthesis

Under an argon atmosphere, a 50 wt % sodium hydroxide solution (67.7 g, 0.8462 mol) was added dropwise to a slurry of physostigmine salicylate (100 g, 0.2418 mol) in degassed DI water (300 mL) at 45° C. During the addition the temperature was kept between 45 and 55° C. After about 3 hours at 45° C., the yellow solution was cooled to 25 to 30° C. and tert-butyl methyl ether (300 mL) was added. The pH of the aqueous phase was adjusted to 9.1 with an aqueous solution of sodium meta bisulfite (54 g, $Na_2S_2O_5$, 250 mL water). The mixture was stirred for 30 minutes, the phases were allowed to settle and then separated. The aqueous phase was extracted twice for 30 minutes each with tert-butyl methyl ether (300 mL each). The organic phases were combined and washed three times with 20 wt % sodium chloride solution (200 mL each), then dried over magnesium sulfate (150 g) overnight. The slurry was filtered through Celite and the filter cake washed with tert-butyl methyl ether. The filtrate was concentrated to 300 mL at 25 to 29 in of vacuum and the residue co-distilled twice with diethoxymethane (300 mL each). The residue was diluted with diethoxymethane (300 mL) and heated to 50° C. The obtained light slurry was cooled to 5° C., stirred for 45 minutes, then concentrated to about 300 mL. Cold heptane (300 mL) was added dropwise, the slurry stirred for 20 minutes and the volume increased by addition of cold heptane (125 mL). After stirring for about 2 hours the slurry was filtered via a Buchner funnel. The collected solid was washed with cold heptane (200 mL) then dried in vacuo overnight. Eseroline base (35.6 g) was obtained as a white solid in 67.4% yield and 98.3% purity.

Posiphen Synthesis

Eseroline base (50 g, 0.229 mol) was dissolved in 400 mL anhydrous dimethoxyethane under an argon atmosphere. Catalytic amounts of 2.5 M n-butyl lithium in hexanes (6.4 mL, 16 mmol) were added within 1 minute and the solution stirred for 10 minutes. Phenyl isocyanate (27.269 g, 0.2286 mmol) was added over 32 minutes keeping the temperature between 20 and 23° C. The reaction solution was stirred at room temperature for 2 hours 20 minutes, then transferred to an addition funnel. The reaction solution was added over 49 minutes to mixture of DI water (630 mL) and dimethoxyethane (42 mL) under vigorous stirring. The obtained slurry was stirred for 30 minutes, then filtered via a Buchner funnel (Whatman #3 filter paper). The solid residue was washed four times with DI water (100 mL each) and once with heptane (100 mL), then dried at 45° C. and >29 inches of vacuum for 9 hours. Posiphen (74.4 g) was obtained as reddish solid in 96.2% yield and 95.1% purity.

Synthesis of Posiphen D-Tartrate Form A

Under an argon atmosphere a solution of D-tartaric acid (17.12 g, 0.114 mol) in a mixture of anhydrous ethanol (131 mL) and DI water (3.3 mL) was added over 32 minutes to a slurry of posiphen (35 g, 0.1037 mol) in a mixture of anhydrous ethanol (126 mL) and DI water (3.1 mL). After about 60 to 75% of the D-tartaric acid solution was added to the reaction solution, the reaction solution was seeded with posiphen D-tartrate Form A (72 mg). The reaction mixture was stirred for 19 hours 15 minutes at room temperature and then a mixture of isopropanol (490 mL) and water (12 mL) was added over 30 minutes. The slurry was stirred for 3.5 hours at room temperature, filtered via Buchner funnel (Whatman #3 filter paper), was washed twice with isopropanol (100 mL), then dried at 45° C. and under vacuum at 29 inHg for 19 hours to give Form A (38.62 g) in 76% yield and 99.4% purity as a white solid.

Initial characterization was carried out using powder X-ray diffraction (PXRD). The synthesized compound was found to be crystalline (FIG. 1) and was designated as Form A.

DSC analysis of this sample revealed a broad minor endotherm at 81° C., followed by a major endotherm at 146° C. likely attributable to the melt of the material (FIG. 2). TGA analysis revealed a weight loss of 0.84% by 125° C., followed by onset of decomposition at 153° C. (FIG. 2). Thermal analysis indicated that Form A was a non-hydrated/solvated form.

DVS analysis revealed a slightly hygroscopic material (FIG. 3), with a 0.8% weight gain and loss during the sorption and desorption cycles respectively. No overall weight gain/loss was observed after the analysis, but some minor hysteresis was noted. PLM revealed that the sample consists of irregular crystalline blocks (FIG. 4). $^{1}$H NMR analysis of the sample (FIG. 5) confirmed the presence of all the expected protons.

Figure 25:
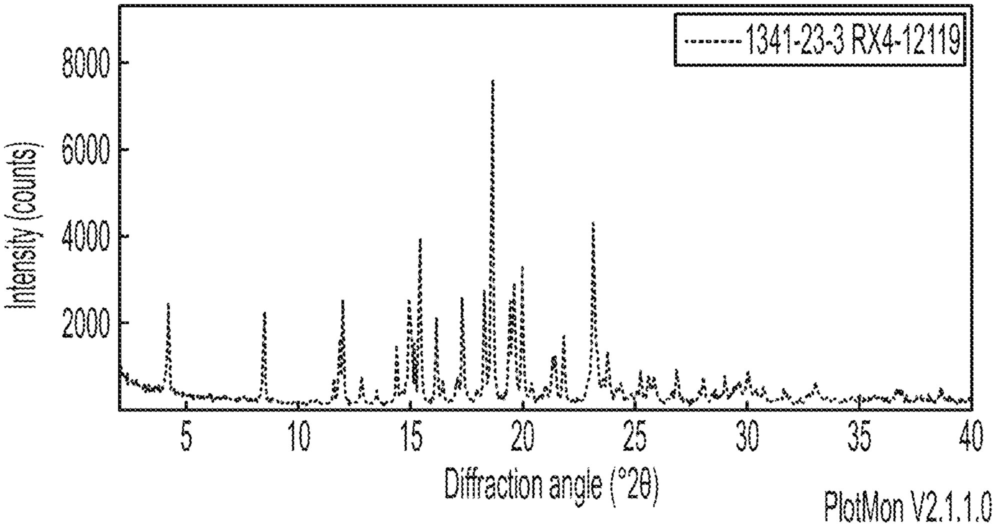
FIG. 25 shows a PXRD trace of Form A following exposure of the compound to 75% relative humidity for 14 days.
Figure 26:
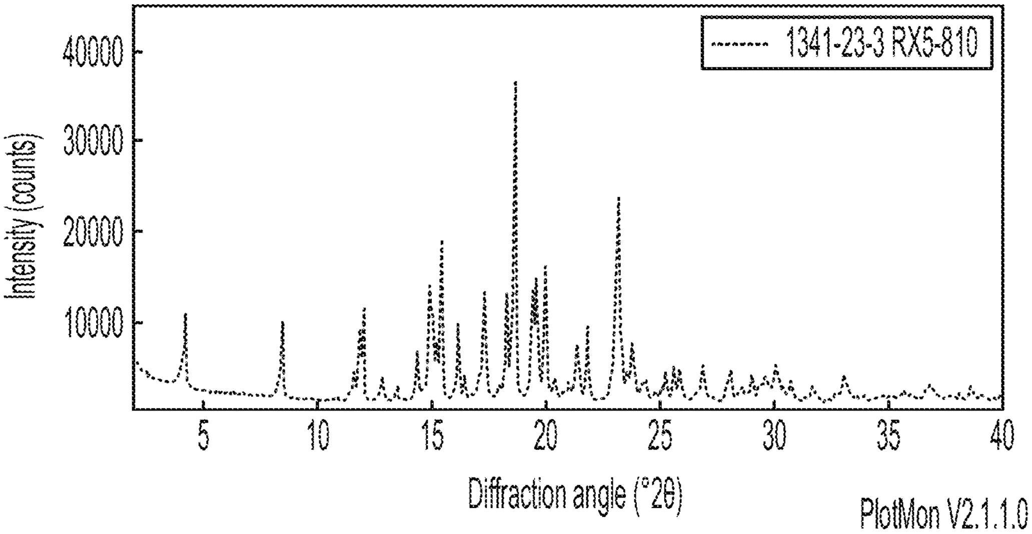
FIG. 26 shows a PXRD trace of Form A following exposure of the compound to 75% relative humidity for 73 days.

A long-term 75% RH stress revealed no form change at 14 and 73 days (FIGS. 25-26). A grinding experiment on Form A also revealed that it was fairly stable to mechanical stress, with no form change observed after the analysis (FIG. 20).

Figure 33:
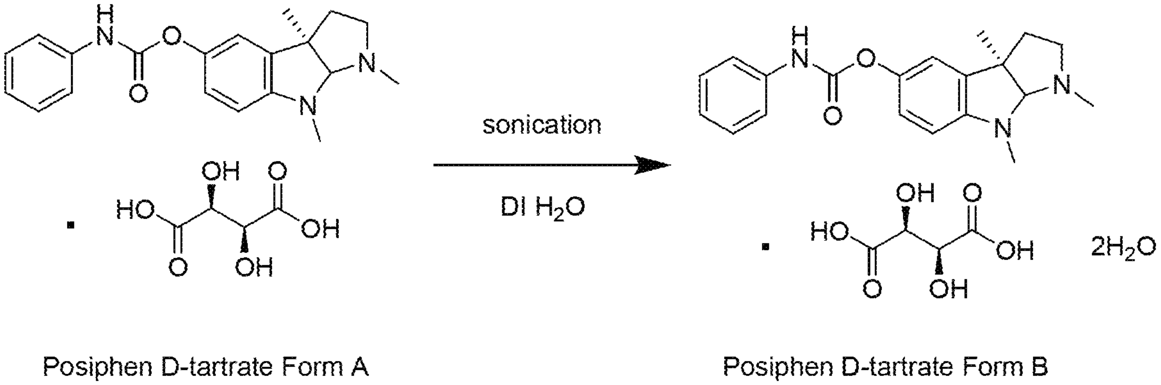
FIG. 33 is a reaction scheme showing the conversion of Form A to Form B.

Example 3—Synthesis of Posiphen D-Tartrate Form B 104.0 mg of posiphen D-tartrate Form A was dissolved in 1 mL of DI water with ~1 minute of sonication. Continued sonication of this clear solution for ~2 more minutes resulted in a white precipitate. This white slurry was then centrifuged, the supernatant pipetted out and the wet residues dried under a flow of air overnight in the fume hood. A reaction scheme is shown in FIG. 33.

$^{1}$H NMR analysis of Form B (FIG. 27) was consistent with the molecular structure of posiphen D-tartrate. The PXRD pattern was successfully indexed (FIG. 17) and the unit cell volume was consistent with a 1:1 posiphen D-tartrate salt with sufficient space to accommodate 2-3 moles of water.

Figure 23:
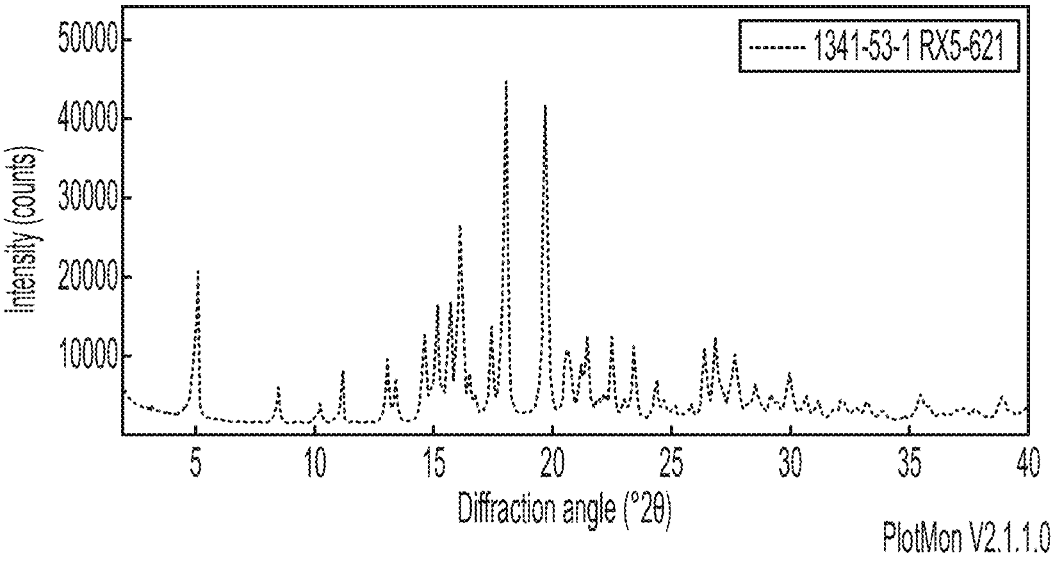
FIG. 23 shows a PXRD trace of Form B following milling with a steel ball for 30 minutes.

Thermal analysis was carried out (FIG. 10), where a 7.1% weight loss starting at 76° C. in its TGA trace coupled with a major endotherm at 93° C. in its DSC trace indicates that it is a dihydrate possessing 2 moles of water per molecule of salt. DVS analysis revealed a slightly hygroscopic nature with a negligible overall net weight gain (FIG. 11). Post DVS PXRD revealed no form change had taken place during the analysis. FTIR (FIG. 12) and Raman (FIG. 13) spectra were also obtained for Form B for reference. Drying a sample of Form B under vacuum overnight at 50° C. did not result in any phase change as indicated in the resulting PXRD (FIG. 23). Milling a neat sample of Form B in a Retsch mill for 30 minutes did not result in any form change as observed in the resulting PRXD (FIG. 24), indicating that it is fairly stable to mechanical stress. As such, Form B appears to be a fairly robust dihydrate of posiphen D-tartrate that is formed at a critical water activity between 0.4 and 0.6 at room temperature. The solubility of Form B was determined in water, and was found to be only a fraction of Form A at 14 mg/mL.

Example 4—Synthesis of Posiphen D-Tartrate Form A+Pattern C 50.0 mg of posiphen D-tartrate was suspended in 0.75 mL of ACN and stirred at 60° C. for 5 days. The slurries were then centrifuged, the supernatant pipetted out and the wet residues dried under a flow of air for a few hours in the fume hood.

Figure 7:
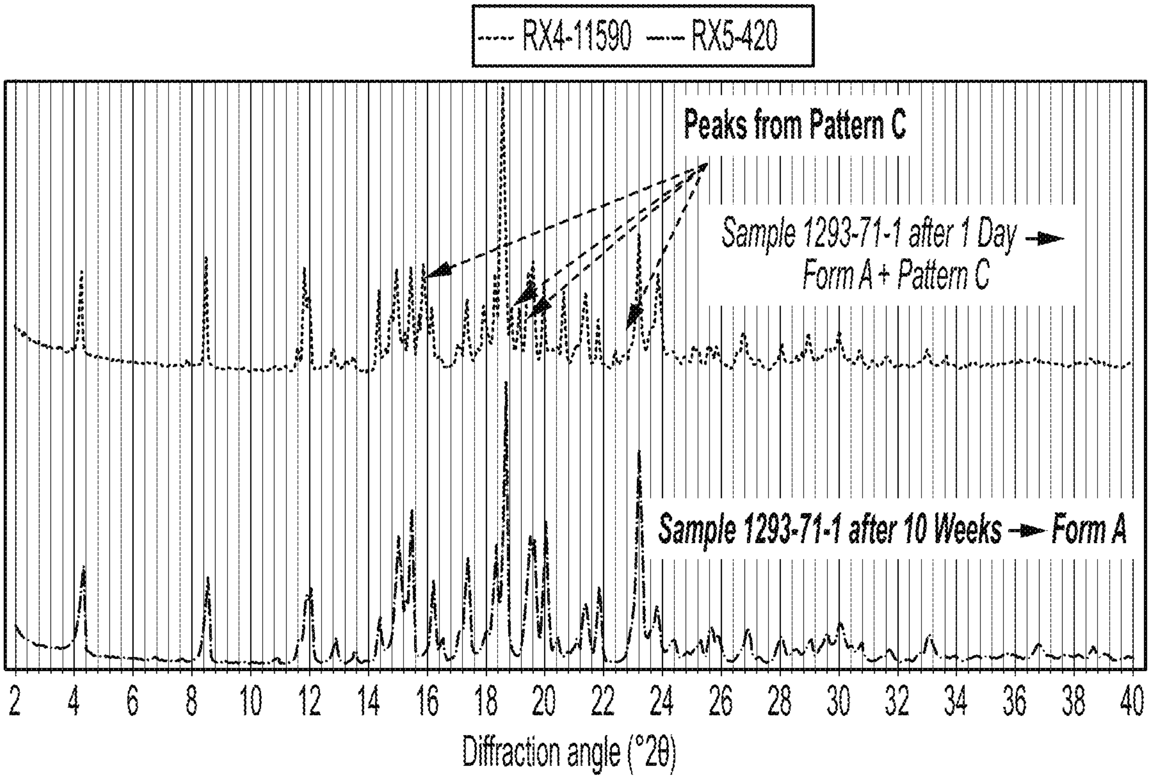
FIG. 7 shows a PXRD overlay of Form A having the peaks of Pattern C analyzed after one day (top trace) and after 10 weeks (bottom trace).
Figure 28:
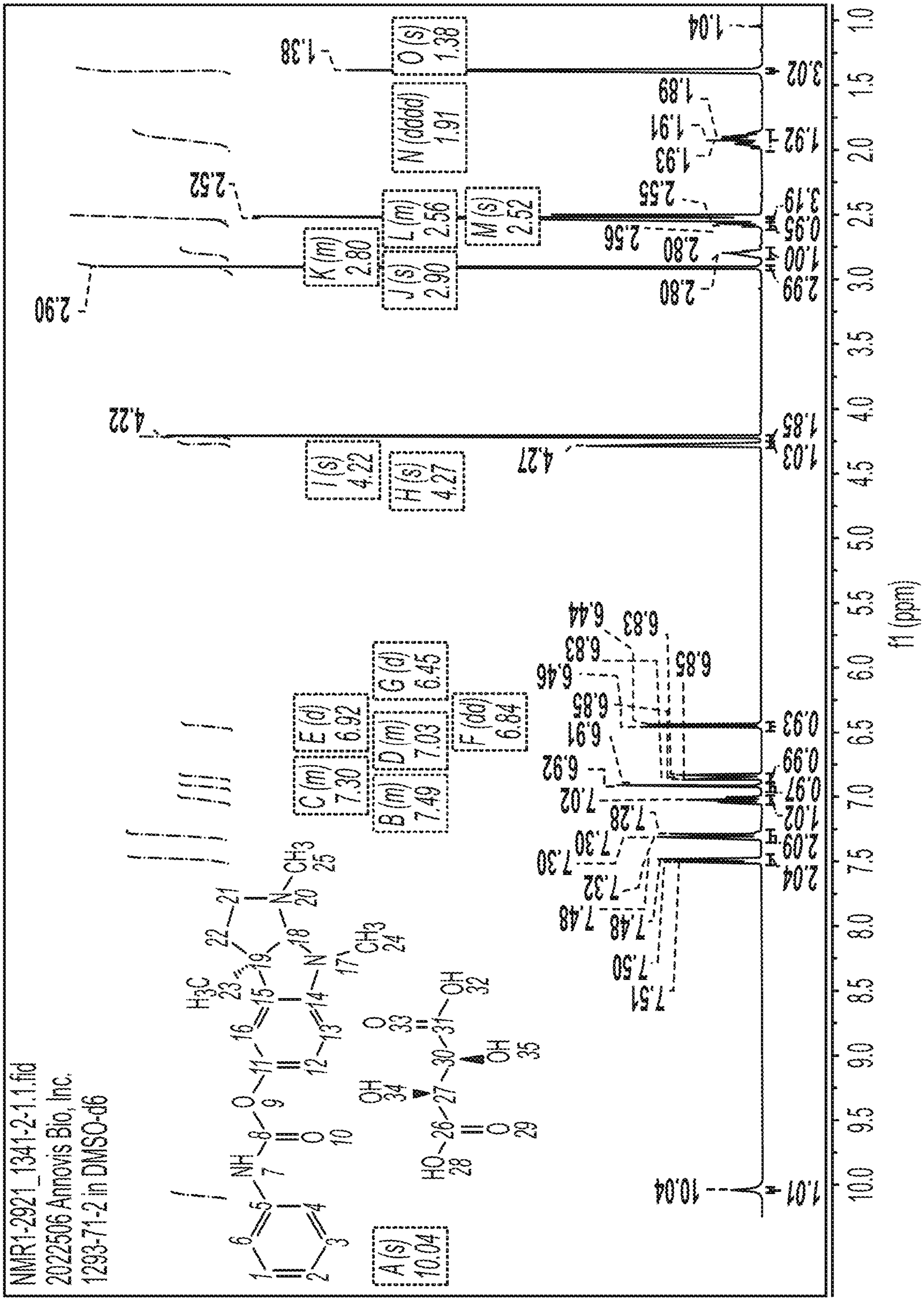
FIG. 28 shows a $^{1}$H-NMR spectrum of Form A having the peaks of Pattern C. The spectrum was acquired in DMSO-d6.
Figure 29A:
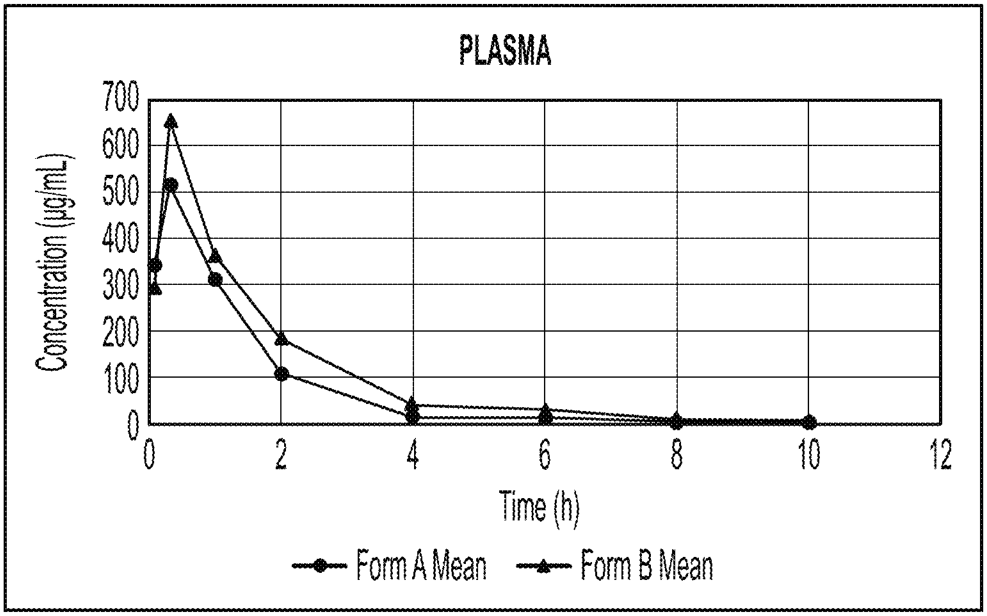
FIG. 29A shows pharmacokinetic data with respect to the concentration (μg/mL) of Form A and Form B in plasma.
Figure 29B:
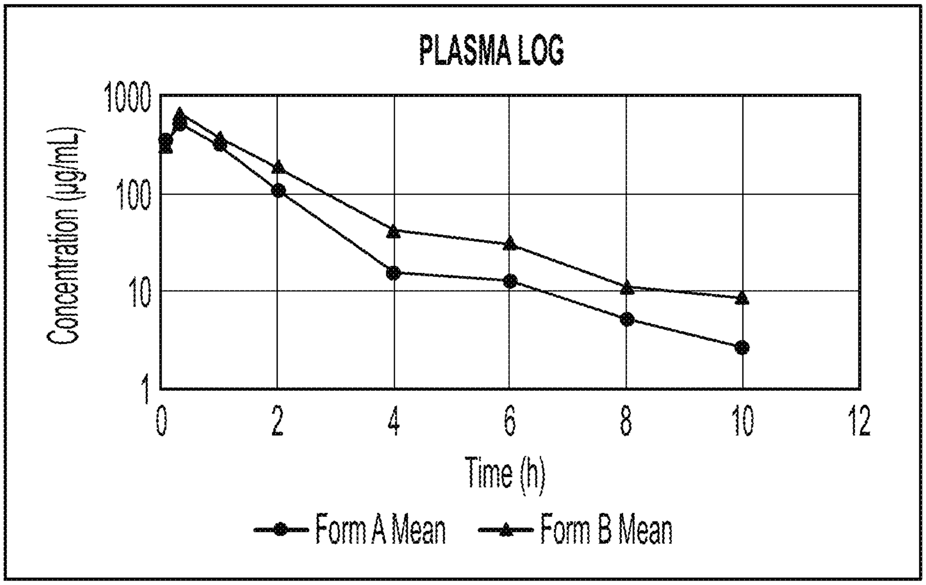
FIG. 29B shows the data of FIG. 29A in which the drug concentration (μg/mL) is presented in a base 10 logarithmic scale.
Figure 30:
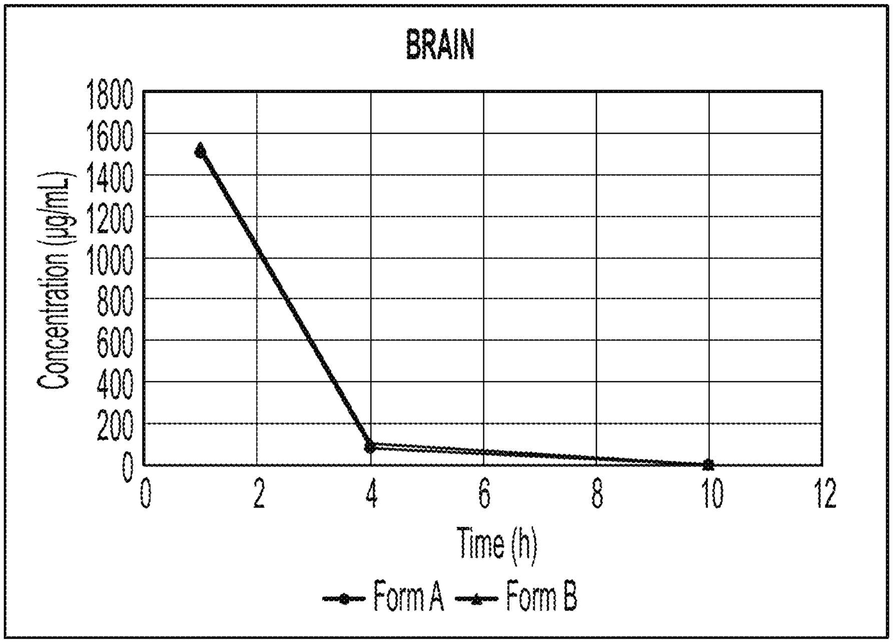
FIG. 30 shows pharmacokinetic data with respect to the concentration (μg/mL) of Form A and Form B in the brain.
Figure 31:
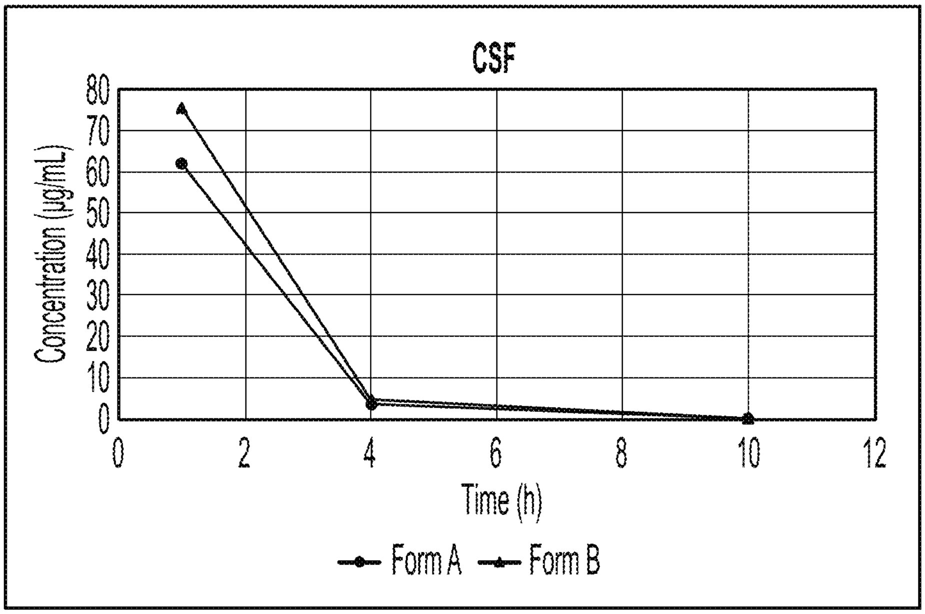
FIG. 31 shows pharmacokinetic data with respect to the concentration (μg/mL) of Form A and Form B in cerebrospinal fluid.

Pattern C was always obtained in combination with Form A. Form A+Pattern C was obtained exclusively from experiments conducted at elevated temperature (>50° C.) including several slurries, and was characterized using various techniques. $^{1}$H NMR analysis (FIG. 28) was consistent with the molecular structure of posiphen D-tartrate. DSC analysis revealed a trace very similar to Form A, with the same major endotherm at 150° C. but with a minor broad endotherm at 68° C. instead of 81° C. (FIG. 14). Similarly, its TGA trace showed the same negligible weight loss till 125° C., but with an onset of decomposition at 147° C. instead of 153° C. (FIG. 14). Analysis of the same sample by PXRD after ~10 weeks of storage under ambient conditions (and ~2 weeks after thermal analysis) revealed Pattern C had converted to Form A. This indicates that the phase of Pattern C is metastable in the solid state (FIG. 7). This could also mean that the thermal trace obtained likely corresponds to a pure phase of Form A rather than Form A+Pattern C.

In one embodiment, the crystalline (3aR)-1, 3a, 8-trimethyl-1, 2, 3, 3a, 8, 8a-hexahydropyrrolo (2, 3-b) indol-5-yl phenyl-carbamate tartrate Form A having the peaks of Pattern C is characterized by an X-ray powder diffraction pattern having characteristic peaks at 4.2, 7.8, 8.5, 10.8, 11.1, 11.6, 11.8, 12.0, 12.5, 12.8, 13.3, 13.4, 14.4, 14.6, 14.8, 15.0, 15.2, 15.4, 15.7, 15.9, 16.1, 16.4, 17.0, 17.3, 17.7, 17.9, 18.3, 18.6, 18.9, 19.1, 19.4, 19.6, 20.0, 20.4, 20.6, 21.1, 21.4, 21.8, 22.4, 22.6, 23.2, 23.5, 23.8, 24.3, 24.8, 25.0, 25.6, 25.8, 26.7, 27.3, 28.0, 29.0, 30.0, 30.7, 31.1, 31.6, 33.0, 33.6 in 2θ.

XRPD peaks, relative intensities, and d-spacing values of an embodiment of posiphen D-tartrate Form A having the peaks of Pattern C are shown in the following Table 6.

TABLE 6

XRPD Peaks and Relative Intensities of Posiphen D-tartrate Form A Having the Peaks of Pattern C

| Diffraction Angle 2θ | Relative Intensity % | d-spacing Value (Å) |
|---|---|---|
| 4.2 | 37 | 20.94 |
| 7.8 | 7 | 11.28 |
| 8.5 | 42 | 10.43 |
| 10.8 | 5 | 8.18 |
| 11.1 | 5 | 7.97 |
| 11.6 | 11 | 7.64 |
| 11.8 | 39 | 7.49 |
| 12.0 | 26 | 7.38 |
| 12.5 | 5 | 7.09 |
| 12.8 | 11 | 6.91 |
| 13.3 | 7 | 6.67 |
| 13.4 | 9 | 6.59 |
| 14.4 | 31 | 6.17 |
| 14.6 | 11 | 6.08 |
| 14.8 | 21 | 5.99 |
| 15.0 | 38 | 5.92 |
| 15.2 | 18 | 5.83 |
| 15.4 | 39 | 5.74 |
| 15.7 | 22 | 5.64 |
| 15.9 | 39 | 5.58 |
| 16.1 | 25 | 5.49 |
| 16.4 | 9 | 5.39 |
| 17.0 | 13 | 5.21 |
| 17.3 | 28 | 5.12 |
| 17.7 | 11 | 5.01 |
| 17.9 | 25 | 4.95 |
| 18.3 | 36 | 4.85 |
| 18.6 | 100 | 4.78 |
| 18.9 | 24 | 4.71 |
| 19.1 | 24 | 4.65 |
| 19.4 | 37 | 4.58 |
| 19.6 | 38 | 4.53 |
| 20.0 | 33 | 4.44 |
| 20.4 | 11 | 4.34 |
| 20.6 | 30 | 4.30 |
| 21.1 | 13 | 4.22 |
| 21.4 | 30 | 4.16 |
| 21.8 | 21 | 4.08 |
| 22.4 | 10 | 3.97 |
| 22.6 | 8 | 3.93 |
| 23.2 | 50 | 3.84 |
| 23.5 | 17 | 3.78 |
| 23.8 | 36 | 3.73 |
| 24.3 | 11 | 3.66 |
| 24.8 | 8 | 3.60 |
| 25.0 | 12 | 3.56 |
| 25.6 | 11 | 3.48 |
| 25.8 | 11 | 3.45 |
| 26.7 | 16 | 3.34 |
| 27.3 | 7 | 3.27 |
| 28.0 | 13 | 3.18 |
| 29.0 | 17 | 3.08 |
| 30.0 | 17 | 2.98 |
| 30.7 | 10 | 2.91 |
| 31.1 | 7 | 2.87 |
| 31.6 | 9 | 2.83 |
| 33.0 | 11 | 2.72 |
| 33.6 | 8 | 2.67 |

Example 5—Synthesis of Amorphous Posiphen D-Tartrate 306.8 mg of posiphen D-tartrate was dissolved in 10 mL DI water with vortexing. The solution was then filtered into a 50 mL round bottom (RB) flask and subsequently frozen in an acetone dry ice bath. The flask with its frozen contents was then placed on a Labconco FreeZone 1 lyophilizer pre-equilibrated to ~−52° C. and left overnight. A fluffy white residue remained after 24 hrs. The resulting compound was analyzed by XRPD and the resulting trace (FIG. 26) confirmed the amorphous character of the compound.

Figure 15:
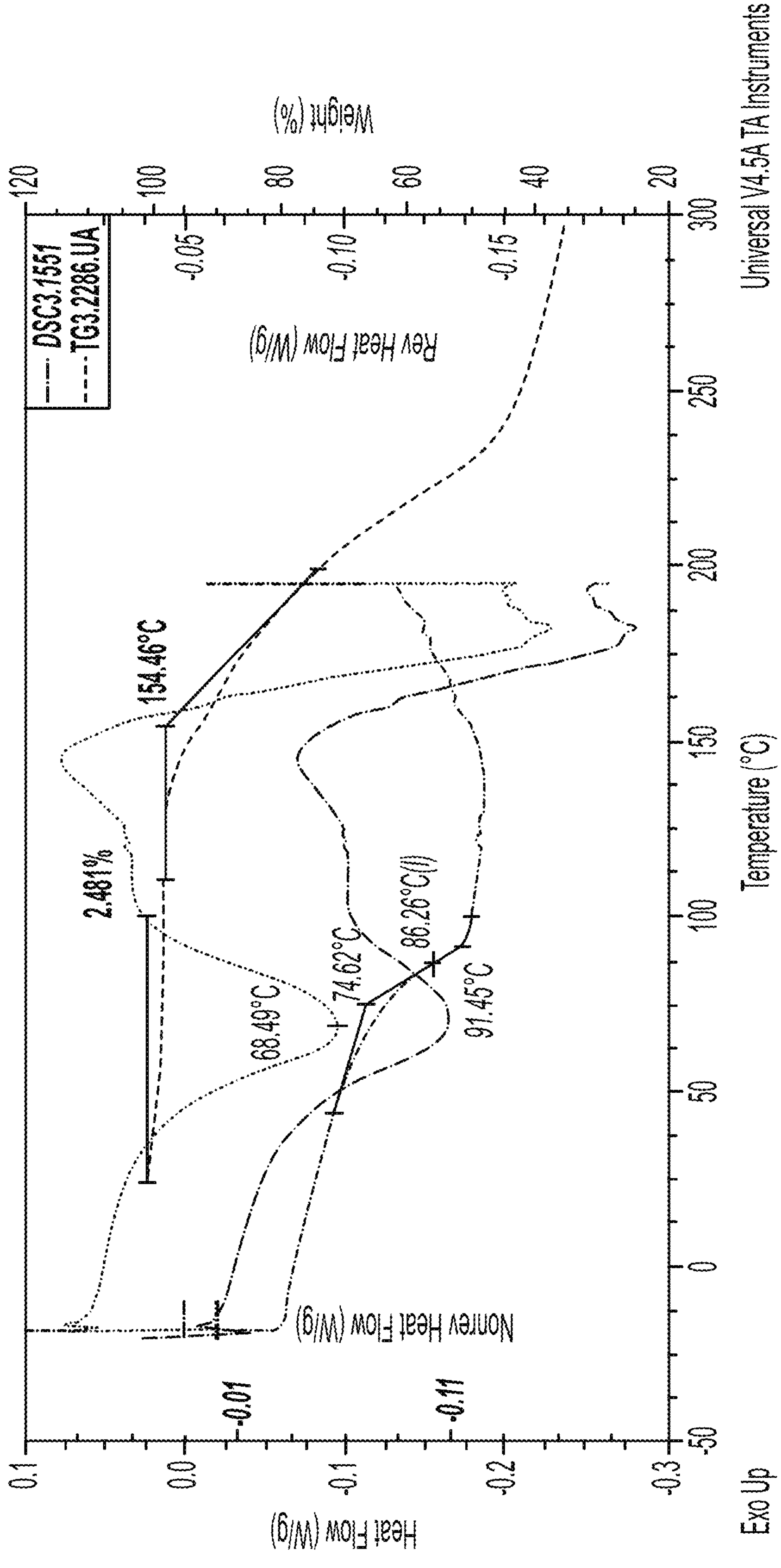
FIG. 15 shows a DSC and TGA (blue) trace of amorphous posiphen D-tartrate. The green trace shows the overall activity of the compound. The brown trace was obtained using reversible heat flow. The pink trace shows the results from non-reversible heat flow.

Modulated-DSC of the amorphous posiphen D-tartrate (FIG. 15) revealed an endotherm at 69° C., possibly originating from the dehydration of adsorbed moisture as observed by the 2.5% weight loss by 125° C. from its TGA trace (FIG. 15). A glass transition temperature ($T_g$) of 86° C. was also identified from the reversible heat flow. Given the 2.5% water adsorbed during ambient storage, amorphous posiphen D-tartrate appears to be hygroscopic in nature, and the dry $T_g$ would likely be higher than what is currently observed.

Example 6—XRPD Indexing of Crystalline Posiphen D-Tartrate Form A

Figure 16:
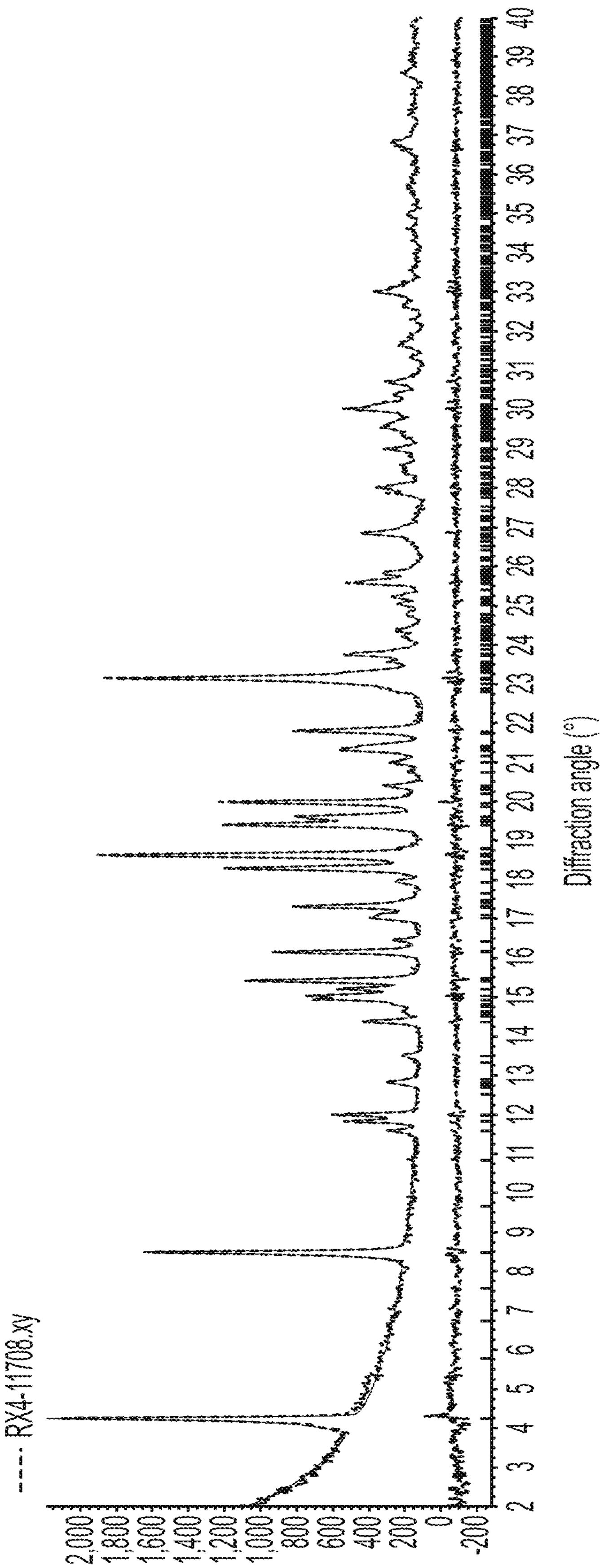
FIG. 16 shows the indexing of Form A. The blue trace is the obtained experimental data, the red trace is the fit, the grey trace is the fit residual, and the blue notches at the bottom show allowed peak positions.

The resulting trace from the XRPD indexing of posiphen D-tartrate Form A is shown in FIG. 16.

Indexing of an XRPD pattern is a computational approach that utilizes the XRPD data generated from the bulk powder and attempts to model the size/shape/geometry of a unit cell that would generate a powder pattern consistent with the XRPD data. The method searches a set of crystallographic space group and unit cell parameters to match the observed Bragg angles in a powder pattern (Coelho, A. A., "Indexing of Powder Diffraction Patterns by Iterative Use of Singular Value Decomposition", *J. Appl. Cryst.,* 2003, 36, 86-95). If successful and all observed Bragg peaks can be attributed to the indexing solution, it is highly likely the XRPD pattern represents a single crystalline phase.

The indexing solution can be used to perform whole-pattern Pawley refinement in order to accurately determine the unit cell volume and cell parameters and investigate the fit residual for crystalline phase impurities. (Pawley, G. S., "Unit Cell Refinement from Powder Diffraction Scans", *J. Appl. Cryst.,* 1981, 14, 357-361) TOPAS 6 (version 6.0.0.9, 2018, Bruker AXS GmbH, Karlsruhe, Germany) was used for Indexing and Pawley refinements. Refinements are performed on all parameters simultaneously to a convergence of 0.001 in $\chi 2$.

Refined unit cell parameters, space group and fit residual are provided in a table with the graphical representation of the Pawley refinement result. Further refinement parameters include, but may not be limited to the following. The background was modeled using a Chebychev polynomial function and a 1/x contribution to account for air scattering. If needed, further broad scattering features such as caused by amorphous content may be modeled by a broad first principle peak contribution.

Bragg peaks are fitted to a first principles peak function with Gaussian crystallite size broadening (τG), and Lorentzian strain broadening (εL). Peak asymmetry due to axial divergence was modeled using the simple axial model (SAM) with a start value of 10 mm. Sample displacement (dsamp)/Zero error (z0) correction was used to account for Bragg peak shifts and listed in the parameter table if used.

TABLE 7

| Space group | P1 | Cell Volume ($Å^3$) | 2435.7 |
|---|---|---|---|
| a (Å) | 7.5950851 | α (°) | 96.63367 |
| b (Å) | 15.8314532 | β (°) | 91.08384 |
| c (Å) | 21.0009697 | γ (°) | 103.5461 |

TABLE 7-continued

| Space group | P1 | Cell Volume (Å$^3$) | 2435.7 |
|---|---|---|---|
| $d_{samp}$ (mm) | −0.042 | | |
| $R_{wp}$ | 6.6% | | |

Stoichiometry Cell Content

Molecular volumes were predicted according to Hofmann (“Fast Estimation of Crystal Densities”, *Acta Cryst.*, 2002, B57, 489-493):

API, $C_{20}H_{23}N_3O_2$: 452.42 Å$^3$,

Tartaric acid, $C_4H_6O_6$: 154.3 Å$^3$,

API:tartaric acid, 1:1, P1 (m=1), Z=4 predicts a total volume of $$4\times(452.42+154.3)=2426.88\ Å^3.$$

Residual volume:

$$dV = 2435.7 - 2426.88 = 8.82\ Å^3.$$

Example 7—XRPD Indexing of Crystalline Posiphen D-Tartrate Form B

The resulting trace from the XRPD indexing of crystalline posiphen D-tartrate is shown in FIG. 17.

TABLE 8

| Space group | $P_{212121}$ | Cell Volume (Å$^3$) | 2677.8 |
|---|---|---|---|
| a (Å) | 7.1291832 | α (°) | 90 |
| b (Å) | 10.8795518 | β (°) | 90 |
| c (Å) | 34.5244343 | γ (°) | 90 |
| $d_{samp}$ (mm) | −0.147 | | |
| $R_{wp}$ | 9.2% | | |

A small impurity peak at 5.3° was observed. The marker at 19.7° in FIG. 17 marks a broad feature to account for amorphous scattering.

Stoichiometry Cell Content

Molecular volumes were predicted according to Hofmann (“Fast Estimation of Crystal Densities”, *Acta Cryst.*, 2002, B57, 489-493):

API, $C_{20}H_{23}N_3O_2$: 452.42 Å$^3$,

Tartaric acid, $C_4H_6O_6$: 154.3 Å$^3$,

Water, $H_2O$: 21.55 Å$^3$

API:tartaric acid:water, 1:1:2, $P2_12_12_1$ (m=4), predicts a total volume of $$4\times(452.42+154.3+2\times21.55)=2599.28\ Å^3.$$

Residual volume:

$$dV = 2677.8 - 2599.28 = 78.52\ Å^3.$$

API:tartaric acid:water, 1:1:3, $P2_12_12_1$ (m=4), predicts a total volume of $$4\times(452.42+154.3+3\times21.55)=2685.48\ Å^3.$$

Residual volume:

$$dV = 2677.8 - 2685.48 = -7.68\ Å^3.$$

Example 8—Plasma and Tissue Pharmacokinetics of Posiphen D-Tartrate Form A and Posiphen D-Tartrate Dihydrate (Form B) in Male CD-1 Mice Following Single Intravenous (IV) and Oral (PO) Administration The purpose of this study was to determine the pharmacokinetics of posiphen D-tartrate (Form A) Sample 1341-40-1 and posiphen D-tartrate dihydrate (Form B) Sample 1341-39-1 in plasma, CSF and brain, following single intravenous bolus and oral gavage administrations to male CD-1 mice.

Male CD-1 (ICR) mice were divided in to eight study groups (3 mice per group). Following acclimation to the study environment, Groups 01 and 02 received one single intravenous bolus injection of Form A in saline (2 mg/mL concentration, 10 mg/kg dose, 5 mL/kg dose volume). Groups 03, 04, and 05 received one single oral dosage of Form A (5 mg/mL concentration, 50 mg/kg dose, 10 mL/kg dose volume). Groups 06, 07, and 08 received one single oral dosage of Form B (5 mg/mL concentration, 50 mg/kg dose, 10 mL/kg dose volume).

The parameters of the study are shown in the following Tables 9-13.

TABLE 9

Study Design

| Group No. | Phase No. | Test Article | No. of animals | Sex | Dose Route | Dose (mg/kg) | Conc (mg/mL) | Dose Volume (mL/kg) | Is Cassette | Is Diff | Vehicle |
|---|---|---|---|---|---|---|---|---|---|---|---|
| 01 | NA | Posiphen D-tartrate (Form A) Sample 1341-40-1 | 3 | Male | IV bolus | 10 | 2 | 5 | False | False | Saline |
| 02 | NA | Posiphen D-tartrate (Form A) Sample 1341-40-1 | 3 | Male | IV bolus | 10 | 2 | 5 | False | False | Saline |
| 03 | NA | Posiphen D-tartrate (Form A) Sample 1341-40-1 | 3 | Male | PO | 50 | 5 | 10 | False | False | Corn oil |

TABLE 9-continued

Study Design

| Group No. | Phase No. | Test Article | No. of animals | Sex | Dose Route | Dose (mg/kg) | Conc (mg/mL) | Dose Volume (mL/kg) | Is Cassette | Is Diff | Vehicle |
|---|---|---|---|---|---|---|---|---|---|---|---|
| 04 | NA | Posiphen D-tartrate (Form A) Sample 1341-40-1 | 3 | Male | PO | 50 | 5 | 10 | False | False | Corn oil |
| 05 | NA | Posiphen D-tartrate (Form A) Sample 1341-40-1 | 3 | Male | PO | 50 | 5 | 10 | False | False | Corn oil |
| 06 | NA | Posiphen D-tartrate dihydrate (Form B) Sample 1341-39-1 | 3 | Male | PO | 50 | 5 | 10 | False | False | Corn oil |
| 07 | NA | Posiphen D-tartrate dihydrate (Form B) Sample 1341-39-1 | 3 | Male | PO | 50 | 5 | 10 | False | False | Corn oil |
| 08 | NA | Posiphen D-tartrate dihydrate (Form B) Sample 1341-39-1 | 3 | Male | PO | 50 | 5 | 10 | False | False | Corn oil |

Is cassette: True means cassette compounds dosing for this group. False means single compound dosing Is diff: True means cassette compounds dosing and dose level are different for each compound. False means dose level are same for each compound or single compound dosing

TABLE 10

Dose Schedule

| Group No. | Day | Time (h) | Dose Article |
|---|---|---|---|
| 01 | 1 | 0 | Posiphen D-tartrate (Form A) Sample 1341-40-1 |
| 02 | 1 | 0 | Posiphen D-tartrate (Form A) Sample 1341-40-1 |
| 03 | 1 | 0 | Posiphen D-tartrate (Form A) Sample 1341-40-1 |
| 04 | 1 | 0 | Posiphen D-tartrate (Form A) Sample 1341-40-1 |
| 05 | 1 | 0 | Posiphen D-tartrate (Form A) Sample 1341-40-1 |
| 06 | 1 | 0 | Posiphen D-tartrate dihydrate (Form B) Sample 1341-39-1 |
| 07 | 1 | 0 | Posiphen D-tartrate dihydrate (Form B) Sample 1341-39-1 |
| 08 | 1 | 0 | Posiphen D-tartrate dihydrate (Form B) Sample 1341-39-1 |

TABLE 11

Test Article Information

| Test Article | Lot or Batch No. | M.W. | F.W. | Formula | Exact mass | Storage condition | Analyte? |
|---|---|---|---|---|---|---|---|
| Posiphen D-tartrate (Form A) Sample 1341-40-1 | BPR-21-114-B1-19 | 337.41 | 487.5 | $C_{20}H_{23}N_3O_2•C_4H_6O_6$ | 337.2 | room temperature approx. 25° C. | True |
| Posiphen D-tartrate dihydrate (Form B) Sample 1341-39-1 | 1341-39-1 | 337.41 | 523.53 | $C_{20}H_{23}N_3O_2•C_4H_6O_6•2H_2O$ | 337.2 | room temperature approx. 25° C. | False |

Semi-quantitative determination of N1-Norposiphen and N8-Norposiphen ($C_{19}H_{21}N_3O_2$), which are metabolites of posiphen D-tartrate. $Q_1$ is [M + H](324.16).

TABLE 12

Sample Collection

| Group | Phase | Analyte | Dosage (mg/kg) | A1 | A2 | A3 | A4 | A5 | A6 | Day | Time Point (hr) | B | CSF | P |
|---|---|---|---|---|---|---|---|---|---|---|---|---|---|---|
| 01 | NA | Posiphen D-tartrate (Form A) Sample 1341-40-1 | 10 | M01 | M02 | M03 | | | | 1 | 0.083 | | | 1 |
| | | | | | | | | | | | 0.33 | 1 | 1 | 1 |
| 02 | NA | Posiphen D-tartrate (Form A) Sample 1341-40-1 | 10 | M04 | M05 | M06 | | | | 1 | 1 | | | 1 |
| | | | | | | | | | | | 2 | | | 1 |
| | | | | | | | | | | | 4 | | | 1 |
| | | | | | | | | | | | 6 | | | 1 |
| | | | | | | | | | | | 8 | | | 1 |
| | | | | | | | | | | | 10 | 1 | 1 | 1 |
| 03 | NA | Posiphen D-tartrate (Form A) Sample 1341-40-1 | 50 | M07 | M08 | M09 | | | | 1 | 0.083 | | | 1 |
| | | | | | | | | | | | 0.33 | | | 1 |
| | | | | | | | | | | | 1 | 1 | 1 | 1 |
| 04 | NA | Posiphen D-tartrate (Form A) Sample 1341-40-1 | 50 | M10 | M11 | M12 | | | | 1 | 2 | | | 1 |
| | | | | | | | | | | | 4 | 1 | 1 | 1 |
| 05 | NA | Posiphen D-tartrate (Form A) Sample 1341-40-1 | 50 | M13 | M14 | M15 | | | | 1 | 6 | | | 1 |
| | | | | | | | | | | | 8 | | | 1 |
| | | | | | | | | | | | 10 | 1 | 1 | 1 |
| 06 | NA | Posiphen D-tartrate (Form B) Sample 1341-39-1 | 50 | M16 | M17 | M18 | | | | 1 | 0.083 | | | 1 |
| | | | | | | | | | | | 0.33 | | | 1 |
| | | | | | | | | | | | 1 | 1 | 1 | 1 |
| 07 | NA | Posiphen D-tartrate (Form B) Sample 1341-39-1 | 50 | M19 | M20 | M21 | | | | 1 | 2 | | | 1 |
| | | | | | | | | | | | 4 | 1 | 1 | 1 |
| 08 | NA | Posiphen D-tartrate (Form B) Sample 1341-39-1 | 50 | M22 | M23 | M24 | | | | 1 | 6 | | | 1 |
| | | | | | | | | | | | 8 | | | 1 |
| | | | | | | | | | | | 10 | 1 | 1 | 1 |

TABLE 13

Animal Specifications

| | |
|---|---|
| Strain: | CD-1(ICR) |
| Species: | Mouse |
| Vender: | WTLH-BJ |
| Gender: | Male |
| Maximal Body Weight (g): | |
| Maximal Body Weight (kg): | |
| Minimal Body Weight (g): | |
| Minimal Body Weight (kg) | |
| Age: | 7-9 W |
| Total Number of Animals: | 24 |
| Overnight Fast of Animals: | true |
| Food Returned: | 4 hours post dosing |
| Surgery Type: | |
| Euthanasia: | $CO_2$ euthanasia |
| Animal No. of Non-surgery: | 24 |
| Animal No. of CAC: | |
| Animal No. of CAC + JVC: | |
| Animal No. of BDC: | |
| Animal No. of Others: | |
| Comments: | or other qualified vendors |
| Species Abbr: | M |
| Overnight Fast of animals comments | Fed for IV group , fasted for PO |

Acclimation/Quarantine

Before being placed in the study, animals were acclimated to the test facility for at least 3 days, and were checked for their general health by veterinary staff or other authorized personnel at the end of acclimation period.

Animal Husbandry

Animals were group-housed (up to four animals/sex/cage) in polysulfone cages with certified aspen wood bedding during the acclimation and study periods. Animals may be individually housed after surgery or when there is special requirement in protocol, as well as, for behavioral or health reasons, or due to cage mate death.

The bedding was routinely analyzed by the manufacturer for environmental contaminants, and the results are reviewed and assessed by veterinary staff, and archived at WuXi AppTec.

Environment controls will be set to maintain a temperature range of 20-26° C., a relative humidity range of 40 to 70%, and a 12-hour light/12-hour dark cycle. The light/dark cycle may be interrupted for study-related activities. The temperature and relative humidity will be continuous monitored by Vaisala ViewLinc Monitoring system.

Animal Fasting Detail Information

Certified rodent diet and water were provided to all animals ad libitum, unless fasting for study procedures.

Water was autoclaved before provided to the animals. Water samples were periodically analyzed by a certified laboratory for specified microorganisms and environment contaminants. The diet was routinely analyzed by the manufacturer for specified microorganisms, nutritional components and environmental contaminants. Results were reviewed and assessed by veterinary staff, and archived at WuXi AppTec.

Dose Formulation

Formulation for PO

Saline:

An appropriate amount of test article was weighed and mixed with appropriate volume of vehicle to get a clear solution or a uniform suspension. Vortexing or sonication in water bath were used as necessary to obtain the clear solution or uniform suspension. Animals were dosed within four hours following preparation of the formulation.

Formulation samples were removed from each of the formulation solutions or suspensions, transferred into 1.5 mL of polypropylene microcentrifuge tubes and run dose validation was performed using LC/UV or LC-MS/MS.

Formulation for IV

Corn Oil:

Formulation samples were removed from each of the formulation clear solutions, transferred into 1.5 mL of polypropylene microcentrifuge tubes and run dose validation by LC/UV or LC-MS/MS.

Dose Administration

For IV dosing, the dose formulation was bolus injected via tail vein following facility SOPs. The dose volume was determined by the animals' body weight collected on the morning of dosing day.

For PO dosing, the dose formulation was administered via oral gavage following facility SOPs. The dose volume was determined by the animals' body weight collected on the morning of dosing day.

Sample Collection

Blood Collection

Each blood collection (about 0.025 mL per time point) was performed from saphenous vein or other suitable site of each animal into pre-chilled commercial EDTA-K2 tubes and placed on wet ice until centrifugation and subsequent quick freezing.

Plasma Processing

Blood samples were processed for plasma by centrifugation at approximately 4° C., 3,200 g for 10 min. Plasma was collected respectively and transferred into pre-labeled 96 well plate or polypropylene tubes, quick frozen over dry ice and kept at −60° C. or lower until LC-MS/MS analysis.

CSF Collection

CSF samples were collected as per the sampling schedule. CSF volume was approximately 3 μL per time point. CSF samples were frozen on dry ice and stored at −60° C. or lower for analysis.

Tissue Collection and Homogenization

The animals were euthanized using $CO_2$ inhalation and the brain was collected from each animal, respectively. The whole brain was collected per facility SOP. After collection, the tissue was washed with cold saline, wiped dry, weighed, and homogenized immediately or kept at −70±10° C.

The tissue was homogenized using homogenizing buffer (MeOH/15 mM PBS (1:2, v:v)) at the ratio of 1:9 (1 g tissue with 9 mL buffer, the dilution ratio is 10). The tissue homogenate was kept at −70±10° C. until LC-MS/MS analysis.

Liquid chromatography was carried out using a High Performance Liquid Chromatography (HPLC) system (Agilent Technologies, model LC-1200, Englewood, USA) equipped by an auto sampler. The analytical column used was a $C_{18}$ column (ZORBAX-XDB-ODS, USA) (2.1 mm×30 mm, 3.5 μm) and was operated at 250° C. The mobile phase consisted of acetonitrile-water 60:40 (v/v) and 0.2% formic acid was set at a flow rate of 0.2 ml/min.

Mass Spectrometric (MS) detection was performed using a triple-quadruple mass spectrometer (Agilent Technologies, model LCMS-6410, Englewood, USA) with an Electrospray Ionization (ESI) interface. The ESI source was set at positive ionization mode. The MS operating conditions were optimized as follows: Ion spray voltage was set to 4000 V, temperature of the ion transfer capillary was 250° C., Nebulizer gas pressure was 40 psi and curtain gas pressure was 50 psi. The quantification was performed via peak-area. Data acquisition and processing were accomplished using Agilent LC/MS/MS solution Software for LC/MS/MS-6410 system.

Plasma concentration versus time data were plotted and analyzed by non-compartmental approaches using the Phoenix WinNonlin 6.3 software program. Related pharmacokinetic parameters were calculated according to dosing route, e.g. Cl, Vdss and $C_0$ for intravenous administration, $C_{max}$, $T_{max}$ or % F for extravascular administration, and $T_{1/2}$, $AUC_{(0-t)}$, $AUC_{(0-inf)}$, $MRT_{(0-t)}$, $MRT_{(0-inf)}$ for all routes.

The pharmacokinetic data from the study are shown in the following Tables 14-16 and are plotted in FIGS. 29A, 29B, and 30-31.

TABLE 14

Concentration of Posiphen D-Tartrate in Plasma

| Time (h) | Form A Mean (μg/mL) | Form B Mean (μg/mL) |
|---|---|---|
| 0.083 | 345 | 296 |
| 0.33 | 516 | 655 |
| 1 | 314 | 366 |
| 2 | 108 | 185 |
| 4 | 15.2 | 41.6 |
| 6 | 12.45 | 30 |
| 8 | 5.1 | 10.8 |
| 10 | 2.63 | 8.41 |

TABLE 15

Concentration of Posiphen D-Tartrate in the Brain

| Time (h) | Form A Mean (μg/mL) | Form B Mean (μg/mL) |
|---|---|---|
| 1 | 1507 | 1532 |
| 4 | 80.7 | 101 |
| 10 | ND | ND |

TABLE 16

Concentration of Posiphen D-Tartrate in Cerebrospinal Fluid

| Time (h) | Form A Mean (μg/mL) | Form B Mean (μg/mL) |
|---|---|---|
| 1 | 61.8 | 75.4 |
| 4 | 3.39 | 4.62 |
| 10 | ND | ND |

As shown in the above pharmacokinetic data and as plotted in FIGS. 66A, 66B, and 67-68, posiphen D-tartrate Form B, a polymorph of posiphen D-tartrate Form A is retained in the blood at higher concentrations for longer periods than Form A, showing that Form B has a longer half-life than Form A.

Form A and Form B are shown to be present in the brain, showing that the API can cross the blood brain barrier. At the first and second measurement points, Form B is present at a higher concentration than Form A, further showing that Form B has a longer drug half-life than Form A. This trend is also evident in the CSF samples taken from the animals in which Form B was shown to be retained at higher concentrations at the same measurement points.

Posiphen D-tartrate Form B, a polymorph of posiphen D-tartrate Form A has similar to or longer pharmacokinetic behavior as compared to Form A. As shown in the above pharmacokinetic experiments measuring the concentrations of the compound in plasma, the brain, and in cerebrospinal fluid over time following administration, is initially present at higher concentrations following administration of the compound and is retained for longer periods in the blood, brain, and cerebrospinal fluid as compared to Form A. Thus, Form B possesses the advantages of a faster delivery and a longer half-life than Form A. These advantages enable higher, initial effective dosages of the drug when utilizing the same amounts and concentrations during administration, wherein the drug persists and retains its efficiency over longer periods of time.

Example 9—Purity Analysis of Posiphen D-Tartrate Form B 116 g of posiphen D-tartrate Form B were synthesized utilizing the methods described previously and was analyzed for purity.

HPLC Analysis

A solution of posiphen D-tartrate Form B obtained utilizing the methods previously described was analyzed using high performance liquid chromatography (HPLC) system, gradient mobile phase programming, and a C-18 column. An ultraviolet HPLC detector was used to measure the peak responses at a wavelength of 280 nm. Mobile Phase A is 0.01 M ammonium acetate, 10% methanol/90% water, and 0.5% acetic acid. Mobile Phase B is 0.01 M ammonium acetate, 100% methanol; 0.5% acetic acid. The reference standard was a 0.5 mg/mL solution of posiphen D-tartrate Form B in methanol, diluted to a final concentration of 0.005 mg/mL in methanol, or 1% of the sample final theoretical concentration of 0.5 mg/mL of posiphen D-tartrate Form B prepared similarly. A high-performance liquid chromatography system capable of programmed gradient operation was used, with an HPLC UV/VIS detector and the ability to monitor 280 nm. Column: 3.9×150 mm Waters Symmetry C-18 column, 5 μm, (or equivalent) capable of at least 20,000 plates/column for fluorescein. Flow Rate: 0.6 mL/min. The gradient program was as follows as shown in Table 17:

TABLE 17

Gradient program for HPLC

| Time (min) | % Mobile Phase A | % Mobile Phase B |
|---|---|---|
| 0 | 80% | 20% |
| 60 | 20% | 80% |
| | Column wash | |
| 61 | 0% | 100% |
| 66 | 0% | 100% |
| | Equilibration | |
| 67 | 80% | 20% |

Using peak areas, the percent concentration of impurities equal to or greater than 0.025% were calculated, as shown in the calculation section below. Although the limit of quantitation for this method is 0.025%, impurities are generally reported at concentrations ≥0.05%.

The relative retention time was calculated by dividing the retention time of the impurity peak by the retention time of the peak corresponding to the product of interest.

Chiral HPLC to assess enantiomer content was performed utilizing the above method with a chiral stationary phase.

Gas Chromatography

Headspace gas chromatography was used to determine the concentration of residual solvents in the obtained posiphen D-tartrate Form B. Briefly, a gas chromatograph (Agilent technologies 6890N) equipped with a flame ionization detector, a headspace sampler (Agilent technologies G1888) was used to load the sample. An analytical balance (XS 205 from Mettler Toledo) and autopipette (100-1000 μL from Eppendorf) were used.

The conditions used in the headspace injector and gas chromatograph are shown in the following Table 18:

| Headspace injector | | Gas chromatograph | |
|---|---|---|---|
| Oven equilibration temperature | 80° C. | Column | SPB ™-624, Supelco, 30 m length, 0.25 mm internal diameter, and 1.4 μm film thickness |
| Loop temperature | 90° C. | Carrier gas | Nitrogen |
| Transfer line temperature | 100° C. | Flow rate | 1.0 mL per minute (linear velocity 26 cm/s) |
| GC cycle time | 45 min | Injector temperature | 170° C. |
| Oven/vial equilibration time | 30 min | Detector temperature | 250° C. |
| Pressurization time | 0.5 min | Split ratio | 1:10 |
| Loop fill time | 1.0 min | Oven temperature program | Initial 40° C., held for 12 min; Increase at 10° C. per minute to 220° C.; Held at 220° C. for 5 min |

-continued

| Headspace injector | | Gas chromatograph |
|---|---|---|
| Injection time | 0.5 min | |
| Loop equilibration time | 0.5 min | |
| Vial pressure | 14 psi | |

DMSO was utilized as the standard and sample diluent. A stock solution of posiphen D-tartrate Form B and its known residual solvents (ethanol, methyl tertiary butyl ether, N,N-dimethylacetamide, ethyl acetate, dichloromethane, n-heptane, and toluene) was preprepared such that the final concentrations of residual solvents were as follows: 5000 ppm ethanol, 5000 ppm methyl tert-butyl ether, 1090 ppm N,N-dimethylacetamide, 5000 ppm ethyl acetate, 600 ppm dichloromethane, 5000 ppm n-heptane, and 890 ppm toluene.

The standard vial was prepared with 1 mL of the standard solution and the sample vials were prepared with approximately 120 mg of sample with 1 mL DMSO as diluent.

Quantitative NMR (Q-NMR)

A known amount between 4-12 mg of posiphen D-tartrate Form B was weighed on a balance and dissolved in 600 μL of DMSO-d6 in a 5 mm NMR tube. A known amount of dimethylsulfone of a known purity was added as an internal calibrant. The sample was analyzed on a Bruker Avance NEO 400 spectrometer (400 MHz $^1$H) spectrometer.

The results from HPLC, chiral HPLC, Q-NMR, in addition to Karl Fischer and acid-base titrations to determine water and acid content, respectively, are shown in the following Table 19.

TABLE 19

Purity analysis results

| Test | Method | Results | |
|---|---|---|---|
| Appearance | Visual | White solid | |
| Identification | $^1$H-NMR | Consistent with structure of posiphen D-tartrate Form B | |
| | LCMS | Consistent with exact mass of posiphen D-tartrate Form B | |
| Purity (% area) | HPLC | 99.9% | |
| | | RRT | % area |
| Impurities (% area) | HPLC | 1.12 | 0.06 |
| Enantiomer Content (% area) | Chiral HPLC | 0.06% | |
| Residual solvent | Headspace gas chromatography | 130 ppm ethanol and 114 ppm methyl tert-butyl ether detected; N,N-dimethylacetamide, ethyl acetate, dichloromethane, n-heptane, and toluene not detected | |
| Assay (% w/w) (calculated on a $C_{20}H_{23}N_3O_2 \cdot C_4H_6O_6 \cdot 2H_2O$ basis) | Quantitative NMR | 100.4% | |
| Water content (% w/w) | Karl Fischer Titration | 7.0% | |
| D-Tartaric Acid Content (% w/w) | Titration | 28.7% | |
| Polymorph | XRPD | XRPD trace exhibited peaks of Form B | |

The 0.4% difference between the determined Q-NMR purity (100.4%) and the theoretical maximum of 100% is well within the accuracy of typical laboratory settings (NMR and balance validation). Other potential reasons for >100% purity values are differences in residual water content between the internal calibrant and the analyte, or the use of an internal calibrant that is significantly less pure than the target analyte.

Based on the above data, the present methods can be used to synthesize and isolate substantially pure posiphen D-tartrate Form B, or posiphen D-tartrate Form B that has little or no detectable impurities as shown in the above data, by the analyses reported herein (e.g., Q-NMR and/headspace gas chromatography and/or HPLC and/or chiral HPLC).

Additional Description of Embodiments

Additional embodiments of the invention are further described by the following numbered paragraphs:

1. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B).
2. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), characterized by an X-ray powder diffraction pattern having characteristic peaks at 5.16, 8.56, 10.3, 11.24, 13.14, 13.48, 14.66, 15.24, 15.44, 15.76, 16.18, 16.54, 17.48, 17.94, 18.08, 19.72, 20.62, 20.76, 21.22, 21.5, 22.2, 22.54, 23.46, 24.4, 24.72, 26.4, 26.86, 27.14, 27.48, 27.7, 28.52, 28.74, 29.14, 29.96, 30.68, 31.14, 32.3, 33.26, 35.44, 37.24, and 37.74 in 2θ.

3. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), characterized by an X-ray powder diffraction pattern having the following characteristic peaks, relative intensities, and d-spacing values:

| Diffraction Angle 2θ | Relative Intensity % | d-spacing Value (Å) |
|---|---|---|
| 5.16 | 100 | 17.13 |
| 8.56 | 10 | 10.33 |
| 10.3 | 13 | 8.59 |
| 11.24 | 14 | 7.87 |
| 13.14 | 17 | 6.74 |
| 13.48 | 6 | 6.57 |
| 14.66 | 11 | 6.04 |
| 15.24 | 28 | 5.81 |
| 15.44 | 12 | 5.74 |
| 15.76 | 14 | 5.62 |
| 16.18 | 29 | 5.48 |
| 16.54 | 9 | 5.36 |
| 17.48 | 24 | 5.07 |
| 17.94 | 9 | 4.94 |
| 18.08 | 63 | 4.91 |
| 19.72 | 51 | 4.50 |
| 20.62 | 19 | 4.31 |
| 20.76 | 9 | 4.28 |
| 21.22 | 9 | 4.19 |
| 21.5 | 17 | 4.13 |
| 22.2 | 8 | 4.00 |
| 22.54 | 19 | 3.94 |
| 23.46 | 17 | 3.79 |
| 24.4 | 9 | 3.65 |
| 24.72 | 5 | 3.60 |
| 26.4 | 15 | 3.38 |
| 26.86 | 10 | 3.32 |
| 27.14 | 10 | 3.29 |
| 27.48 | 6 | 3.25 |
| 27.7 | 15 | 3.22 |
| 28.52 | 10 | 3.13 |
| 28.74 | 5 | 3.11 |
| 29.14 | 6 | 3.06 |
| 29.96 | 14 | 2.98 |
| 30.68 | 6 | 2.91 |
| 31.14 | 9 | 2.87 |
| 32.3 | 5 | 2.77 |
| 33.26 | 5 | 2.69 |
| 35.44 | 7 | 2.53 |
| 37.24 | 5 | 2.41 |
| 37.74 | 5 | 2.38 |

4. The solid form of any one of paragraphs 1-3, wherein the solid form has the following unit cell information:

| Space group | $P_{212121}$ | Cell Volume ($Å^3$) | 2677.8 |
|---|---|---|---|
| a (Å) | 7.1291832 | α (°) | 90 |
| b (Å) | 10.8795518 | β (°) | 90 |
| c (Å) | 34.5244343 | γ (°) | 90. |
| $d_{samp}$ (mm) | −0.147 | | |
| $R_{wp}$ | 9.2% | | |

5. Substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate, or posiphen D-tartrate Form B that has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC).

6. Posiphen D-tartrate Form B of any of paragraphs 1-4, wherein the posiphen D-tartrate Form B is substantially pure or has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC).

7. A method of preparing a substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), or of preparing posiphen D-tartrate Form B of paragraph 5 or 6, comprising preparing crystalline (3aR)-1, 3a, 8-trimethyl-1, 2, 3, 3a, 8, 8a-hexahydropyrrolo (2, 3-b) indol-5-yl phenyl-carbamate tartrate (posiphen D-tartrate Form A) and converting the posiphen D-tartrate Form A to crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), wherein the substantially pure crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) the posiphen D-tartrate Form B is substantially pure or has little or no detectable impurities as shown in the data herein, by the analyses reported herein (e.g., Q-NMR and/headspace gas chromatography and/or HPLC and/or chiral HPLC), or posiphen D-tartrate Form B having a purity of greater than 99.5%, or having a purity of greater than 99.6%, or having a purity of greater than 99.7%, or having a purity of greater than 99.8%, advantageously as determined by one or more analyses reported herein (e.g., Q-NMR and/headspace gas chromatography and/or HPLC and/or chiral HPLC).

8. A method of preparing a solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate comprising preparing crystalline (3aR)-1, 3a, 8-trimethyl-1, 2, 3, 3a, 8, 8a-hexahydropyrrolo (2, 3-b) indol-5-yl phenyl-carbamate tartrate (posiphen D-tartrate Form A) and converting the posiphen D-tartrate Form A to crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B).

9. A method of paragraph 7 or 8, wherein converting posiphen D-tartrate Form A to posiphen D-tartrate Form B comprises dissolving posiphen D-tartrate Form A in deionized water to form a solution, sonicating the solution until a precipitate is observed, and collecting the precipitate, wherein the precipitate is posiphen D-tartrate Form B.

10. A pharmaceutical formulation comprising the solid form of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B) of any one of paragraphs 1-6, or having been prepared by the method of paragraph 7, 8, or 9 and a pharmaceutically acceptable carrier.

11. The pharmaceutical formulation of paragraph 10, wherein the solid form is a solid unit dosage form.

12. A method of treating a neurological disorder in a subject in need thereof, comprising administering to the subject an effective amount of a pharmaceutical composition comprising crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), posiphen D-tartrate Form B of any one of paragraphs 1-6 or as prepared by the method of paragraphs 7, 8, or 9, and a pharmaceutically acceptable carrier, or said method comprising administering to the subject an effective amount of a pharmaceutical composition of paragraph 10 or 11;

wherein the neurological disorder comprises:

a chronic neurodegeneration, comprising Alzheimer's disease, frontotemporal dementia, chronic traumatic encephalopathy, tauopathies, Parkinson's and alpha-synucleopathies, prion disease, transmissible spongiform encephalopathies (TSE), Down Syndrome, Huntington's disease, amyotrophic lateral sclerosis, multiple sclerosis, or other dementias and neurodegenerative disorders which present as misfolding, aggregation and accumulation of proteins in the brain, resulting in axonal transport impairment, inflammation, and eventual cell death; or an acute neurodegeneration, wherein the acute neurodegeneration comprises traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma; or a neuropsychiatric indication, wherein the neuropsychiatric indication comprises depression, schizophrenia, dementia, Alzheimer's disease, anxiety, or substance abuse disorder; or a mental illness comprising autism, attention deficit-hyperactivity disorder, bipolar disorder, depression and major depressive disorder, behavioral problems, post-traumatic stress disorder or schizophrenia.

13. The method of paragraph 12, wherein the dosage of posiphen D-tartrate Form B is from about 0.1 mg/kg to about 100 mg/kg of body weight; or wherein the dosage of posiphen D-tartrate Form B is from about 1 mg/kg to about 20 mg/kg of body weight.

14. The method of any one of paragraphs 12 or 13, wherein the pharmaceutical composition is administered daily to the subject; or wherein the pharmaceutical composition is administered once daily to the subject.

15. The method of any one of paragraphs 12-14, wherein the subject is human.

16. The method of any one of paragraphs 12-15, wherein the administrating is oral administration.

17. A method of achieving a drug concentration of posiphen D-tartrate in plasma of at least 350 μg/mL one hour after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-15.

18. The method of paragraph 17, wherein the effective amount is about 10 mg/kg to about 50 mg/kg of bodyweight.

19. The method of paragraph 17 or 18, wherein the administering is oral administration.

20. A method of achieving a drug concentration of posiphen D-tartrate in plasma of at least 175 μg/mL two hours after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-19.

21. The method of paragraph 20, wherein the effective amount is about 10 mg/kg to about 50 mg/kg of bodyweight.

22. The method of paragraph 20 or 21, wherein the administering is oral administration.

23. A method of achieving a drug concentration of posiphen D-tartrate in plasma of at least 40 μg/mL four hours after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-22.

24. The method of paragraph 24, wherein the effective amount is about 10 mg/kg to about 50 mg/kg of bodyweight.

25. The method of paragraph 23 or 24, wherein the administering is oral administration.

26. A method of achieving a drug concentration of posiphen D-tartrate in plasma of at least 5 μg/mL ten hours after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-25.

27. The method of paragraph 26, wherein the effective amount is about 10 mg/kg to about 50 mg/kg of bodyweight.

28. The method of paragraph 26 or 27, wherein the administering is oral administration.

29. A method of achieving a brain drug concentration of posiphen D-tartrate of at least 100 μg/mL four hours after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-28.

30. The method of paragraph 29, wherein the effective amount is about 10 mg/kg to about 50 mg/kg of bodyweight.

31. The method of paragraph 29 or 30, wherein the administering is oral administration.

32. A method of achieving a drug concentration of posiphen D-tartrate of at least 75 μg/mL in cerebrospinal fluid one hour after administration in a subject comprising the step of administering an effective amount of (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B); or the method comprises administering an effective amount of posiphen D-tartrate Form B of any one of paragraphs 1-6 or as prepared by the method of paragraph 7, 8, or 9; or the method comprises administering an effective amount of a pharmaceutical formulation of paragraph 10 or 11; or the method comprises performing a method of any one of paragraphs 12-31.

33. The method of paragraph 32, wherein the effective amount is about 10 mg/kg to about 50 mg/kg of bodyweight.

34. The method of paragraph 33, wherein the administering is oral administration.

35. Use of a solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate (posiphen D-tartrate Form B), or use of posiphen D-tartrate Form B of any one of paragraphs 1-6 or as prepared by the method of paragraph 7, 8, or 9, or use of a pharmaceutical formulation of any one of paragraphs 10 or 11, for:

performing a method of any one of paragraphs 12-34; or achieving a drug concentration of posiphen D-tartrate in plasma of at least 350 μg/mL one hour after administration in a subject; or achieving a drug concentration of posiphen D-tartrate in plasma of at least 175 μg/mL two hours after administration in a subject; or achieving a drug concentration of posiphen D-tartrate in plasma of at least 40 μg/mL four hours after administration in a subject; or achieving a drug concentration of posiphen D-tartrate in plasma of at least 5 μg/mL ten hours after administration in a subject; or achieving a brain drug concentration of posiphen D-tartrate of at least 100 μg/mL four hours after administration in a subject; or achieving a drug concentration of posiphen D-tartrate of at least 75 μg/mL in cerebrospinal fluid one hour after administration in a subject; or treatment of a neurological disorder comprising:

a chronic neurodegeneration, comprising Alzheimer's disease, frontotemporal dementia, chronic traumatic encephalopathy, tauopathies, Parkinson's and alpha-synucleopathies, prion disease, transmissible spongiform encephalopathies (TSE), Down Syndrome, Huntington's disease, amyotrophic lateral sclerosis, multiple sclerosis, or other dementias and neurodegenerative disorders which present as misfolding, aggregation and accumulation of proteins in the brain, resulting in axonal transport impairment, inflammation, and eventual cell death; or an acute neurodegeneration, wherein the acute neurodegeneration comprises traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma; or a neuropsychiatric indication, wherein the neuropsychiatric indication comprises depression, schizophrenia, dementia, Alzheimer's disease, anxiety, or substance abuse disorder; or a mental illness comprising autism, attention deficit-hyperactivity disorder, bipolar disorder, depression and major depressive disorder, behavioral problems, post-traumatic stress disorder or schizophrenia.

36. A pharmaceutical composition comprising the posiphen D-tartrate Form B of any one of paragraphs 1-6 or as prepared by the method of paragraph 7, 8, or 9, and a pharmaceutically acceptable carrier, the pharmaceutical formulation of any one of paragraphs 10 or 11, for use in:

performing a method of any one of paragraphs 12-34; or achieving a drug concentration of posiphen D-tartrate in plasma of at least 350 μg/mL one hour after administration in a subject; or achieving a drug concentration of posiphen D-tartrate in plasma of at least 175 μg/mL two hours after administration in a subject; or achieving a drug concentration of posiphen D-tartrate in plasma of at least 40 μg/mL four hours after administration in a subject; or achieving a drug concentration of posiphen D-tartrate in plasma of at least 5 μg/mL ten hours after administration in a subject; or achieving a brain drug concentration of posiphen D-tartrate of at least 100 μg/mL four hours after administration in a subject; or achieving a drug concentration of posiphen D-tartrate of at least 75 μg/mL in cerebrospinal fluid one hour after administration in a subject; or treatment of a neurological disorder comprising:

a chronic neurodegeneration, comprising Alzheimer's disease, frontotemporal dementia, chronic traumatic encephalopathy, tauopathies, Parkinson's and alpha-synucleopathies, prion disease, transmissible spongiform encephalopathies (TSE), Down Syndrome, Huntington's disease, amyotrophic lateral sclerosis, multiple sclerosis, or other dementias and neurodegenerative disorders which present as misfolding, aggregation and accumulation of proteins in the brain, resulting in axonal transport impairment, inflammation, and eventual cell death; or an acute neurodegeneration, wherein the acute neurodegeneration comprises traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma; or a neuropsychiatric indication, wherein the neuropsychiatric indication comprises depression, schizophrenia, dementia, Alzheimer's disease, anxiety, or substance abuse disorder; or a mental illness comprising autism, attention deficit-hyperactivity disorder, bipolar disorder, depression and major depressive disorder, behavioral problems, post-traumatic stress disorder or schizophrenia.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate, wherein the solid form is posiphen D-tartrate Form B.

2. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate, characterized by an X-ray powder diffraction pattern having characteristic peaks at 5.16, 8.56, 10.3, 11.24, 13.14, 13.48, 14.66, 15.24, 15.44, 15.76, 16.18, 16.54, 17.48, 17.94, 18.08, 19.72, 20.62, 20.76, 21.22, 21.5, 22.2, 22.54, 23.46, 24.4, 24.72, 26.4, 26.86, 27.14, 27.48, 27.7, 28.52, 28.74, 29.14, 29.96, 30.68, 31.14, 32.3, 33.26, 35.44, 37.24, and 37.74 in 2θ;

wherein the solid form is posiphen D-tartrate Form B and has a purity of 95% or more.

3. A solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate, characterized by an X-ray powder diffraction pattern having the following characteristic peaks, relative intensities, and d-spacing values:

| Diffraction Angle 2θ | Relative Intensity % | d-spacing Value (Å) |
|---|---|---|
| 5.16 | 100 | 17.13 |
| 8.56 | 10 | 10.33 |
| 10.3 | 13 | 8.59 |
| 11.24 | 14 | 7.87 |
| 13.14 | 17 | 6.74 |
| 13.48 | 6 | 6.57 |
| 14.66 | 11 | 6.04 |
| 15.24 | 28 | 5.81 |
| 15.44 | 12 | 5.74 |
| 15.76 | 14 | 5.62 |
| 16.18 | 29 | 5.48 |
| 16.54 | 9 | 5.36 |
| 17.48 | 24 | 5.07 |
| 17.94 | 9 | 4.94 |
| 18.08 | 63 | 4.91 |
| 19.72 | 51 | 4.50 |
| 20.62 | 19 | 4.31 |
| 20.76 | 9 | 4.28 |
| 21.22 | 9 | 4.19 |
| 21.5 | 17 | 4.13 |
| 22.2 | 8 | 4.00 |
| 22.54 | 19 | 3.94 |
| 23.46 | 17 | 3.79 |
| 24.4 | 9 | 3.65 |
| 24.72 | 5 | 3.60 |
| 26.4 | 15 | 3.38 |
| 26.86 | 10 | 3.32 |
| 27.14 | 10 | 3.29 |
| 27.48 | 6 | 3.25 |
| 27.7 | 15 | 3.22 |
| 28.52 | 10 | 3.13 |
| 28.74 | 5 | 3.11 |
| 29.14 | 6 | 3.06 |
| 29.96 | 14 | 2.98 |
| 30.68 | 6 | 2.91 |
| 31.14 | 9 | 2.87 |
| 32.3 | 5 | 2.77 |
| 33.26 | 5 | 2.69 |
| 35.44 | 7 | 2.53 |
| 37.24 | 5 | 2.41 |
| 37.74 | 5 | 2.38 |

wherein the solid form is posiphen D-tartrate Form B and has a purity of 98% or more.

4. The solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate of claim 1, wherein the solid form has the following unit cell information:

| Space group | $P_{212121}$ | Cell Volume (Å$^3$) | 2677.8 |
|---|---|---|---|
| a (Å) | 7.1291832 | α (°) | 90 |
| b (Å) | 10.8795518 | β (°) | 90 |
| c (Å) | 34.5244343 | γ (°) | 90. |
| $d_{samp}$ (mm) | −0.147 | | |
| $R_{wp}$ | 9.2% | | |

and wherein the solid form is posiphen D-tartrate Form B.

5. The solid form of crystalline (3aR)-1, 3a, 8-trimethyl-1, 2, 3, 3a, 8, 8a-hexahydropyrrolo (2, 3-b) indol-5-yl phenyl-carbamate tartrate dihydrate of claim 1, having a purity of greater than 99.5% as determined by HPLC, and wherein the solid form is posiphen D-tartrate Form B.

6. A method of preparing the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 1, comprising preparing crystalline (3aR)-1, 3a, 8-trimethyl-1, 2, 3, 3a, 8, 8a-hexahydropyrrolo (2, 3-b) indol-5-yl phenyl-carbamate tartrate and converting the crystalline (3aR)-1, 3a, 8-trimethyl-1, 2, 3, 3a, 8, 8a-hexahydropyrrolo (2, 3-b) indol-5-yl phenyl-carbamate tartrate to crystalline (3aR)-1, 3a, 8-trimethyl-1, 2, 3, 3a, 8, 8a-hexahydropyrrolo (2, 3-b) indol-5-yl phenyl-carbamate tartrate dihydrate, wherein the crystalline (3aR)-1, 3a, 8-trimethyl-1, 2, 3, 3a, 8, 8a-hexahydropyrrolo (2, 3-b) indol-5-yl phenyl-carbamate tartrate dihydrate has a purity of greater than 99.5% as determined by HPLC;

wherein the solid form of (3aR)-1, 3a, 8-trimethyl-1, 2, 3, 3a, 8, 8a-hexahydropyrrolo (2, 3-b) indol-5-yl phenyl-carbamate tartrate dihydrate prepared by the method is posiphen D-tartrate Form B; and wherein the crystalline (3aR)-1, 3a, 8-trimethyl-1, 2, 3, 3a, 8, 8a-hexahydropyrrolo (2, 3-b) indol-5-yl phenyl-carbamate tartrate is posiphen D-tartrate Form A.

7. A method of preparing the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 2, comprising preparing crystalline (3aR)-1, 3a, 8-trimethyl-1, 2, 3, 3a, 8, 8a-hexahydropyrrolo (2, 3-b) indol-5-yl phenyl-carbamate tartrate and converting the crystalline (3aR)-1, 3a, 8-trimethyl-1, 2, 3, 3a, 8, 8a-hexahydropyrrolo (2, 3-b) indol-5-yl phenyl-carbamate tartrate to crystalline (3aR)-1, 3a, 8-trimethyl-1, 2, 3, 3a, 8, 8a-hexahydropyrrolo (2, 3-b) indol-5-yl phenyl-carbamate tartrate dihydrate, wherein the crystalline (3aR)-1, 3a, 8-trimethyl-1, 2, 3, 3a, 8, 8a-hexahydropyrrolo (2, 3-b) indol-5-yl phenyl-carbamate tartrate dihydrate has a purity of greater than 99.5% as determined by HPLC;

wherein the solid form of (3aR)-1, 3a, 8-trimethyl-1, 2, 3, 3a, 8, 8a-hexahydropyrrolo (2, 3-b) indol-5-yl phenyl-carbamate tartrate dihydrate prepared by the method is posiphen D-tartrate Form B; and wherein the crystalline (3aR)-1, 3a, 8-trimethyl-1, 2, 3, 3a, 8, 8a-hexahydropyrrolo (2, 3-b) indol-5-yl phenyl-carbamate tartrate is posiphen D-tartrate Form A.

8. A method of preparing the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 3, comprising preparing crystalline (3aR)-1, 3a, 8-trimethyl-1, 2, 3, 3a, 8, 8a-hexahydropyrrolo (2, 3-b) indol-5-yl phenyl-carbamate tartrate and converting the crystalline (3aR)-1, 3a, 8-trimethyl-1, 2, 3, 3a, 8, 8a-hexahydropyrrolo (2, 3-b) indol-5-yl phenyl-carbamate tartrate to crystalline (3aR)-1, 3a, 8-trimethyl-1, 2, 3, 3a, 8, 8a-hexahydropyrrolo (2, 3-b) indol-5-yl phenyl-carbamate tartrate dihydrate, wherein the crystalline (3aR)-1, 3a, 8-trimethyl-1, 2, 3, 3a, 8, 8a-hexahydropyrrolo (2, 3-b) indol-5-yl phenyl-carbamate tartrate dihydrate has a purity of greater than 99.5% as determined by HPLC;

wherein the solid form of (3aR)-1, 3a, 8-trimethyl-1, 2, 3, 3a, 8, 8a-hexahydropyrrolo (2, 3-b) indol-5-yl phenyl-carbamate tartrate dihydrate prepared by the method is posiphen D-tartrate Form B; and wherein the crystalline (3aR)-1, 3a, 8-trimethyl-1, 2, 3, 3a, 8, 8a-hexahydropyrrolo (2, 3-b) indol-5-yl phenyl-carbamate tartrate is posiphen D-tartrate Form A.

9. A pharmaceutical composition comprising the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 1, and a pharmaceutically acceptable carrier;

wherein the solid form is posiphen D-tartrate Form B.

10. A pharmaceutical composition comprising the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 2, and a pharmaceutically acceptable carrier;

wherein the solid form is posiphen D-tartrate Form B.

11. A pharmaceutical composition comprising the solid form of (3aR)-1, 3a, 8-trimethyl-1, 2, 3, 3a, 8, 8a-hexahydropyrrolo (2, 3-b) indol-5-yl phenyl-carbamate tartrate dihydrate of claim 3, and a pharmaceutically acceptable carrier;

wherein the solid form is posiphen D-tartrate Form B.

* * * * *